(12) United States Patent
Skouta et al.

(10) Patent No.: US 11,932,599 B2
(45) Date of Patent: Mar. 19, 2024

(54) FERROPTOSIS INDUCING COMPOUND, COMPOSITIONS COMPRISING THE SAME, AND METHODS OF INDUCING FERROPTOSIS

(71) Applicant: UNIVERSITY OF MASSACHUSETTS, Boston, MA (US)

(72) Inventors: Rachid Skouta, Amherst, MA (US); Thomas K. Dawson, Amherst, MA (US); Rohit Bhadoria, Amherst, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 17/701,872

(22) Filed: Mar. 23, 2022

(65) Prior Publication Data
US 2022/0324798 A1    Oct. 13, 2022

Related U.S. Application Data

(60) Provisional application No. 63/164,694, filed on Mar. 23, 2021.

(51) Int. Cl.
  *C07C 311/16*  (2006.01)
  *C07C 311/20*  (2006.01)
  *C07D 205/12*  (2006.01)

(52) U.S. Cl.
  CPC .......... *C07D 205/12* (2013.01); *C07C 311/16* (2013.01); *C07C 311/20* (2013.01); *C07C 2603/18* (2017.05)

(58) Field of Classification Search
  CPC .................................................. C07C 311/16
  See application file for complete search history.

(56) References Cited

U.S. PATENT DOCUMENTS

2019/0315681 A1  10/2019  Stockwell et al.

OTHER PUBLICATIONS

American Chemical Society. Chemical Abstract Service. RN 321579-87-7. First entered into STN: Feb. 13, 2001. (Year: 2001).*
American Chemical Society. Chemical Abstract Service. RN 331275-54-8. First entered into STN on Apr. 13, 2001. (Year: 2001).*
Dixon, S., et al. "Ferroptosis: An Iron-Dependent Form of Non-Apoptotic Cell Death", Cell. May 25, 2012; 149(5): 1060-1072.
Shimada, K. "Global survey of cell death mechanisms reveals metabolic regulation of ferroptosis", Nature Chemical Biology, vol. 12, Jul. 2016, 497-506.
Skouta, R., "Ferrostatins Inhibit Oxidative Lipid Damage and Cell Death in Diverse Disease Models", J. Am. Chem. Soc. 2014, 136, 4551-4556.

* cited by examiner

*Primary Examiner* — John S Kenyon
(74) *Attorney, Agent, or Firm* — CANTOR COLBURN LLP

(57) ABSTRACT

Provided is a compound according to Formula 1

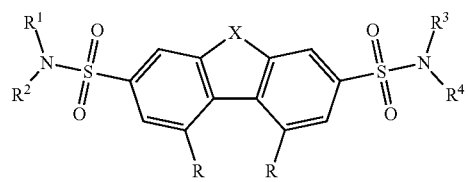

Formula 1 wherein X, R, $R^1$, $R^2$, $R^3$, and $R^4$ are as defined herein. The compound of Formula 1 can be useful in a composition and in a method for inducing ferroptosis in a cell.

8 Claims, 12 Drawing Sheets

FERROPTOSIS INDUCING COMPOUND, COMPOSITIONS COMPRISING THE SAME, AND METHODS OF INDUCING FERROPTOSIS

CROSS REFERENCE TO RELATED APPLICATION

This application claims priority to U.S. Provisional Patent Application No. 63/164,694, filed on Mar. 23, 2021, in the United States Patent and Trademark Office, and all the benefits accruing therefrom under 35 U.S.C. § 119, the content of which is incorporated herein in its entirety by reference.

BACKGROUND

Ferroptosis is a recently described cell death program that is distinct from the better known mechanisms of apoptosis, necrosis, and autophagy. Ferroptosis cell death is iron-dependent and acts in a selective fashion to eliminate tumor cells. This type of cell death has emerged as a forefront research area in recent years and may complement the known cell death pathways to maybe overcome drug resistance.

Ferroptosis inducer compounds may be viewed as a new class of highly specific chemotherapeutic agents that could provide a complementary mechanism to front-line cancer treatment, potentially overcoming some forms of drug resistance. Despite the large number of studies showing the involvement of ferroptosis in physiological and disease states, there are still fundamental gaps in understanding of this newly-discovered cell death mechanism.

Accordingly, there is a continuing need for development of small molecules capable of selectively targeting ferroptosis.

SUMMARY

Provided is a compound according to Formula 1

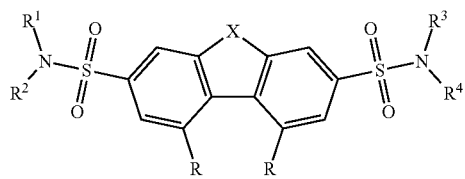

wherein X is —$CH_2$—, —(C=O)—, —(C=N—$NH_2$)—,

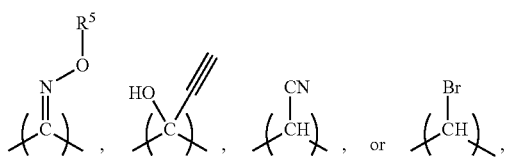

wherein $R^5$ is hydrogen, a $C_{1-6}$ alkyl group, a propargyl group, or a (meth)acrylate group; R is independently at each occurrence hydrogen, a $C_{1-6}$ alkyl group, —$NO_2$, —$NH_2$, —OH, a group of the formula

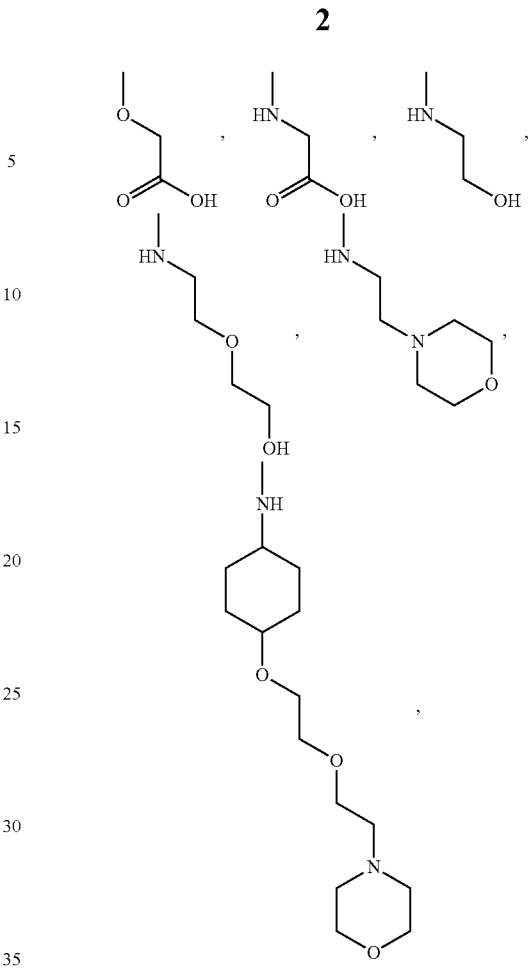

or a combination thereof; and $R^1$, $R^2$, $R^3$, and $R^4$ are independently at each occurrence hydrogen, $C_{1-12}$ alkyl, $C_{3-12}$ cycloalkyl, a $C_{3-12}$ cycloalkyl ether, $C_{5-12}$ bicycloalkyl, a $C_{6-12}$ tricycloalkyl, or a combination thereof, optionally wherein $R^1$ and $R^2$ can join together to form a $C_{3-12}$ azacycloalkyl group or $R^3$ and $R^4$ can join together to form a $C_{3-12}$ azacycloalkyl group, provided that at least one of $R^1$ and $R^2$ and at least one of $R^3$ and $R^4$ are not hydrogen; when any of $R^1$, $R^2$, $R^3$, or $R^4$ are $C_{3-12}$ cycloalkyl, X is not

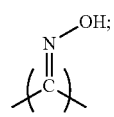

and when at least one of $R^1$ and $R^2$ is a $C_{3-12}$ cycloalkyl ether, $R^3$ and $R^4$ are not a $C_{3-12}$ cycloalkyl ether.

Also provided is a composition comprising the compound.

A method of inducing ferroptosis in a cell comprises contacting the cell with an effective amount of the compound or the composition.

The above described and other features are exemplified by the following figures and detailed description.

BRIEF DESCRIPTION OF THE DRAWINGS

The following figures are exemplary embodiments.

DETAILED DESCRIPTION

Figure 1:
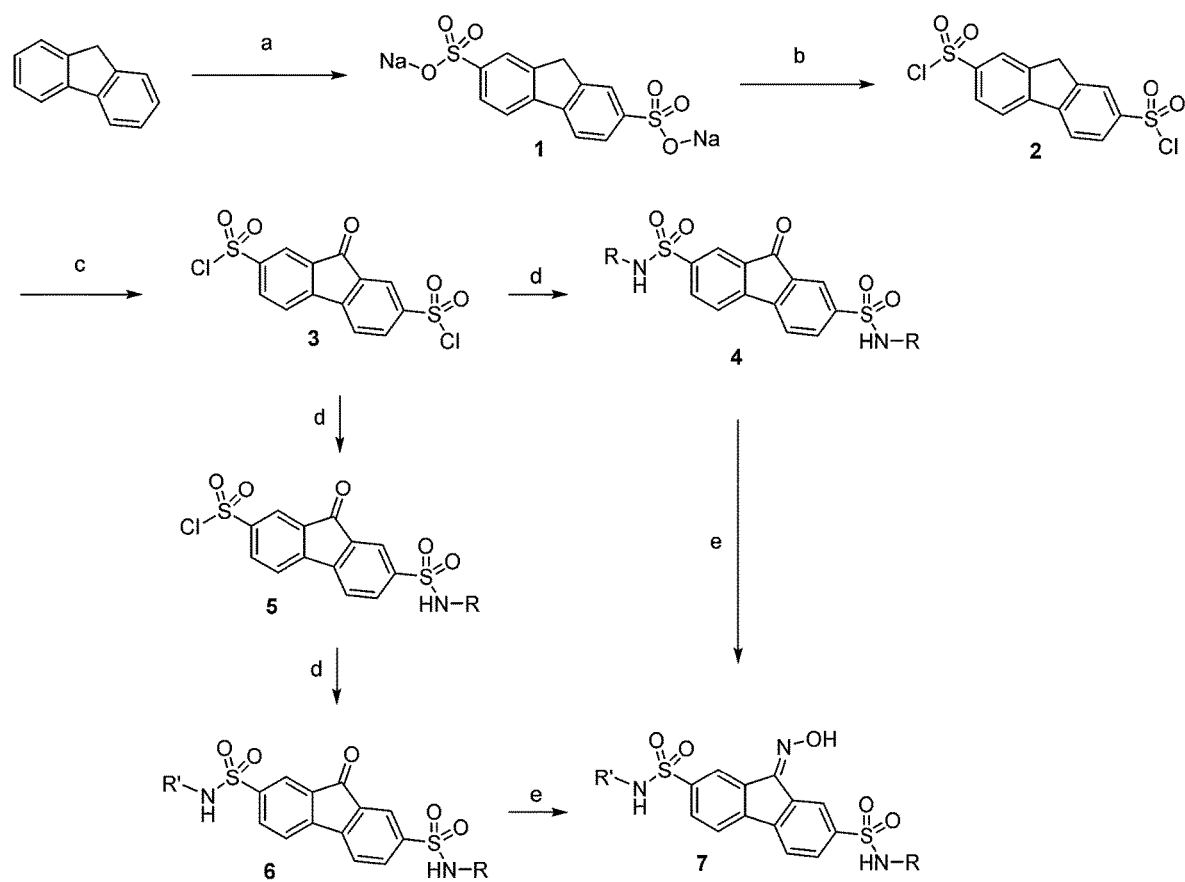
FIG. 1 shows a general scheme for the synthesis of exemplary compounds of the present disclosure. Exemplary reaction conditions for each step can include: (a) HSO₃Cl, AcOH, 140° C.; (b) PCl₅, POCl₃, 100° C.; (c) CrO₃, AcOH, r.t.; (d) 1° or 2° amine, DIPEA, DCM, 0° C. to r.t.; (e) NH₂OH·HCl, NaOH, EtOH, H₂O.

Provided herein are small molecule ferroptosis inducing compounds. The present inventors have unexpectedly discovered that certain compounds can advantageously induce ferroptosis. Accordingly, an aspect of the present disclosure is a compound according to Formula 1

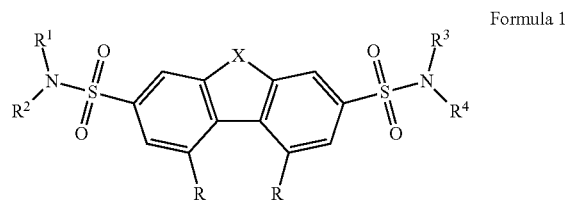

wherein, in Formula 1, X is —CH₂—, —(C=O)—, —(C=N—NH₂)—,

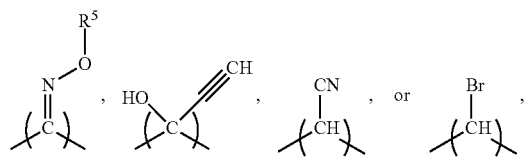

wherein $R^5$ is hydrogen, a $C_{1-6}$ alkyl group, a propargyl group, or a (meth)acrylate group. In an aspect, X is Formula 1 is preferably —CH₂—, —(C=O)—, or

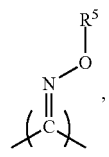

more preferably —(C=O)—, or

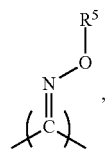

even more preferably

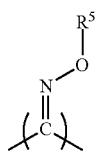

In some aspects, $R^5$ can preferably be a hydrogen.

R in Formula 1 is independently at each occurrence hydrogen, a $C_{1-6}$ alkyl group, $-NO_2$, $-NH_2$, $-OH$, a group of the formula

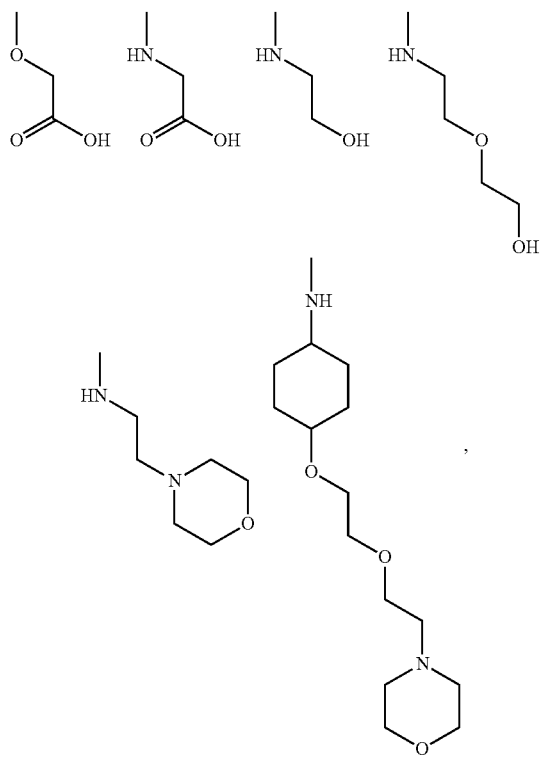

or a combination thereof. In an aspect, R can be hydrogen and the compound can be of Formula 2

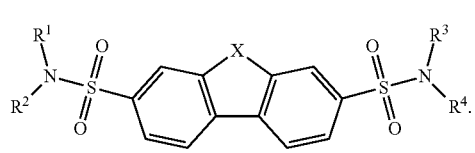

Formula 2

$R^1$, $R^2$, $R^3$, and $R^4$ in Formula 1 or 2 are independently at each occurrence hydrogen, $C_{1-12}$ alkyl, $C_{3-12}$ cycloalkyl, a $C_{3-12}$ cycloalkyl ether, $C_{5-12}$ bicycloalkyl, a $C_{6-12}$ tricycloalkyl (e.g., an adamantyl group), or a combination thereof. In an aspect, $R^1$ and $R^2$ can join together to form a $C_{3-12}$ azacycloalkyl group or $R^3$ and $R^4$ can join together to form a $C_{3-12}$ azacycloalkyl group. At least one of $R^1$ and $R^2$ and at least one of $R^3$ and $R^4$ are not hydrogen. Each of $R^1$, $R^2$, $R^3$, and $R^4$ can be selected such that the compound can be symmetrical (i.e., $R^1$ and $R^2$ are the same as $R^3$ and $R^4$) or asymmetrical (i.e., $R^1$ and $R^2$ are not the same as $R^3$ and $R^4$).

In an aspect, when any one or more of $R^1$, $R^2$, $R^3$, or $R^4$ are $C_{3-12}$ cycloalkyl (e.g., cyclohexyl), X is not

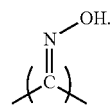

In an aspect, wherein at least one of $R^1$ and $R^2$ is a $C_{3-12}$ cycloalkyl ether, $R^3$ and $R^4$ are not a $C_{3-12}$ cycloalkyl ether.

In an aspect, X can be

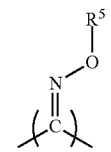

preferably wherein $R^5$ is hydrogen, a propargyl group, or a (meth)acrylate group. In an aspect, $R^5$ is hydrogen. In an aspect, X can be $-(C=O)-$. In an aspect, $R^1$ and $R^3$ are hydrogen and $R^2$ and $R^4$ are $C_{1-6}$ alkyl. In an aspect, $R^1$ and $R^3$ are hydrogen and $R^2$ and $R^4$ are $C_{5-8}$ bicycloalkyl, for example bicyclo[3.1.2.]heptane, bicyclo[1.1.1]pentane, or the like, or a combination thereof. In an aspect, $R^1$ and $R^3$ are hydrogen and $R^2$ and $R^4$ are $C_{8-10}$ tricycloalkyl, for example tricyclo[3.3.1.1]decane (also known as adamantyl), or the like.

In an aspect, one or both, preferably both, of $R^1$ and $R^3$ can be a $C_{4-8}$ cycloalkyl group, preferably a cyclohexyl group, and X is $-(C=O)-$,

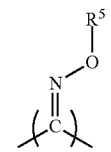

wherein $R^5$ is methyl or propargyl, a (meth)acrylate group,

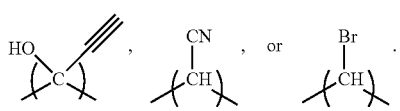

In a specific aspect, each occurrence of R is hydrogen, X is

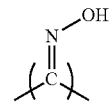

$R^1$ and $R^3$ are hydrogen, and $R^2$ and $R^4$ are bicyclo[3.1.2.]heptane, and the compound is of the formula

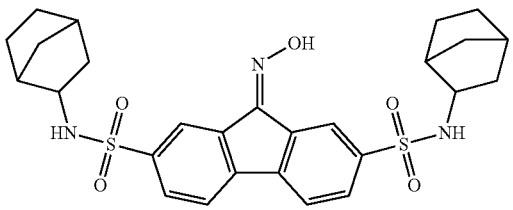

In another specific aspect, each occurrence of R is hydrogen, X is

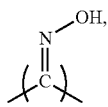

$R^1$ and $R^3$ are hydrogen, and $R^2$ and $R^4$ are bicyclo[1.1.1]pentane, and the compound is of the formula

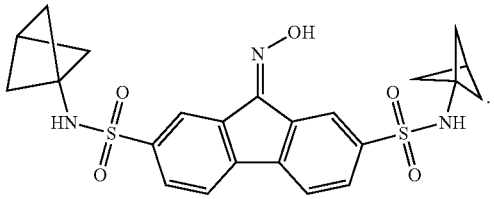 [SMILES: O=S(=O)(NC12CC(C1)C2)c1ccc2c(c1)C(=NO)c1cc(S(=O)(=O)NC34CC(C3)C4)ccc1-2]

In another specific aspect, each occurrence of R is hydrogen, X is

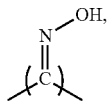

$R^1$ and $R^3$ are hydrogen, and $R^2$ and $R^4$ are 3-pentyl, and the compound is of the formula

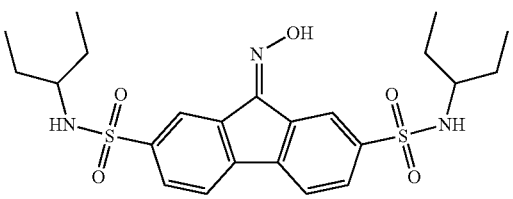

In another specific aspect, each occurrence of R is hydrogen, X is

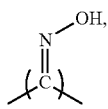

$R^1$ and $R^3$ are hydrogen, and $R^2$ and $R^4$ are spiro[3.3]heptane, and the compound is of the formula

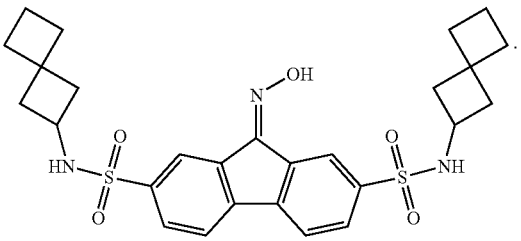 [SMILES: O=S(=O)(NC1CC2(CCC2)C1)c1ccc2c(c1)C(=NO)c1cc(S(=O)(=O)NC3CC4(CCC4)C3)ccc1-2]

In yet another specific aspect, each occurrence of R is hydrogen, X is

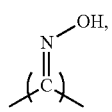

and $R^1$ and $R^2$ and $R^3$ and $R^4$ are joined together to form an azaspiro[3.3]heptane group, and the compound is of the formula

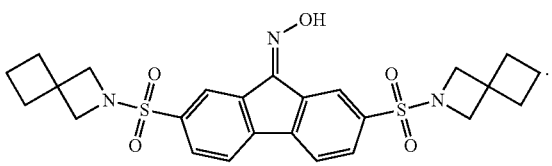 [SMILES: O=S(=O)(c1ccc2c(c1)C(=NO)c1cc(S(=O)(=O)N3CC4(CCC4)C3)ccc1-2)N1CC2(CCC2)C1]

In still another specific aspect, each occurrence of R is hydrogen, X is

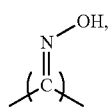

$R^1$ and $R^3$ are hydrogen, and $R^2$ and $R^4$ are each adamantyl groups, and the compound is of the formula

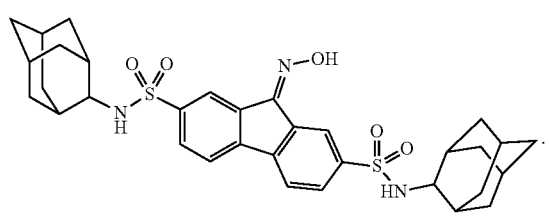 [SMILES: O=S(=O)(NC1C2CC3CC(C2)CC1C3)c1ccc2c(c1)C(=NO)c1cc(S(=O)(=O)NC3C4CC5CC(C4)CC3C5)ccc1-2]

The foregoing exemplary aspects of the present disclosure should not be construed as limiting. It will be understood that the present disclosure may cover other derivatives of the compound of Formula 1 that are not specifically identified (e.g., by structure or by name) herein. Additional compounds contemplated by the present disclosure can include, for example,
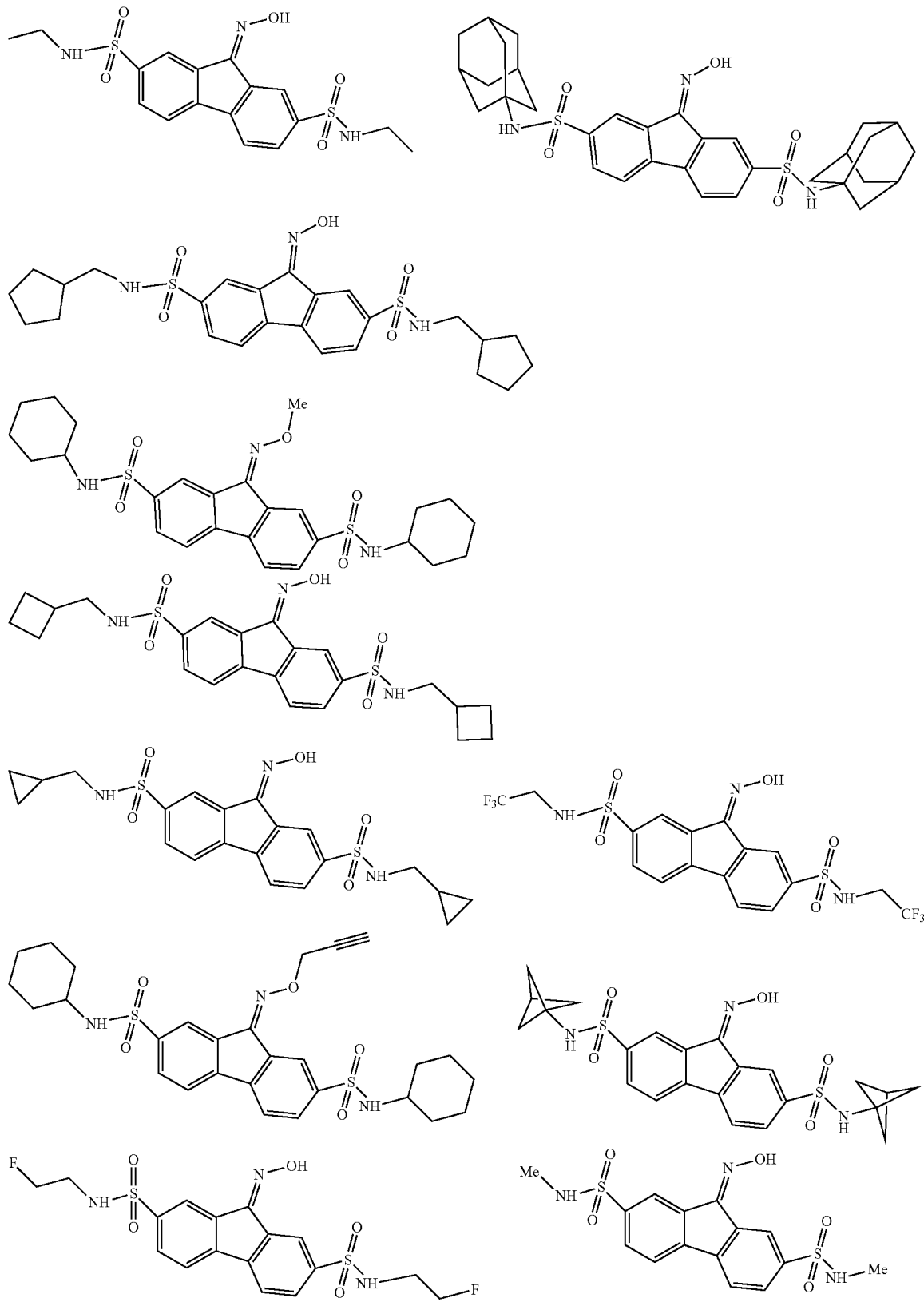

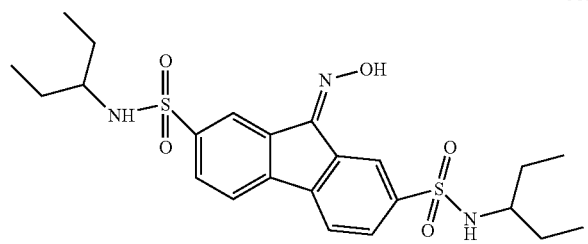
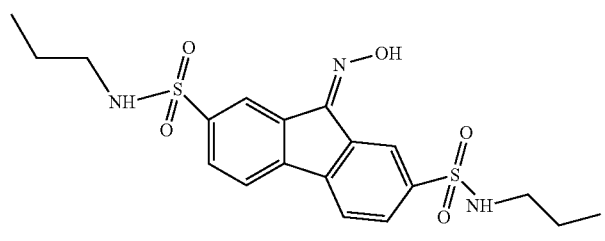
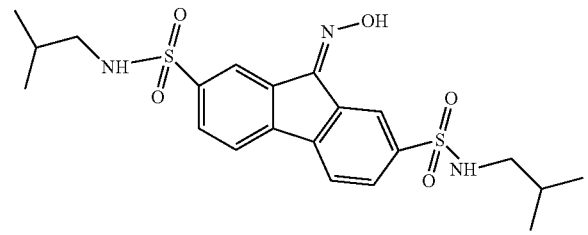
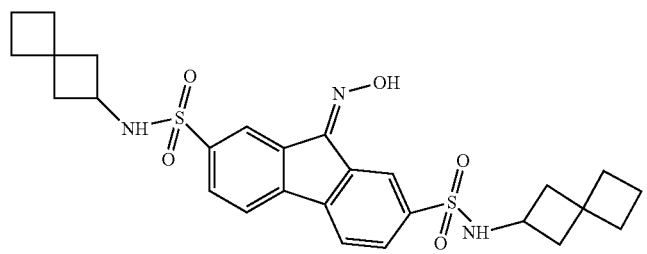
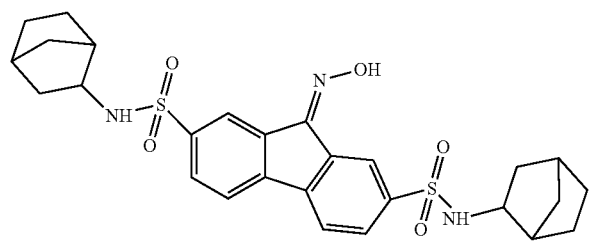
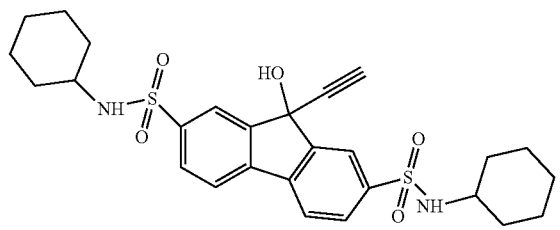
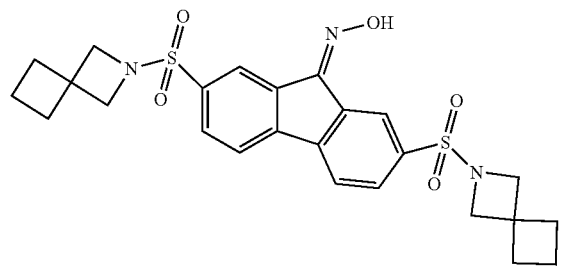
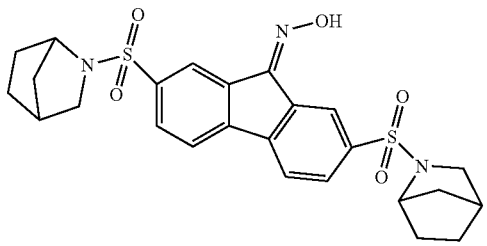
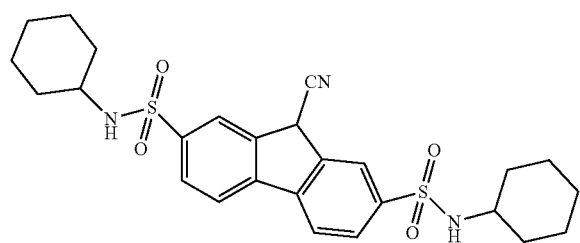

13
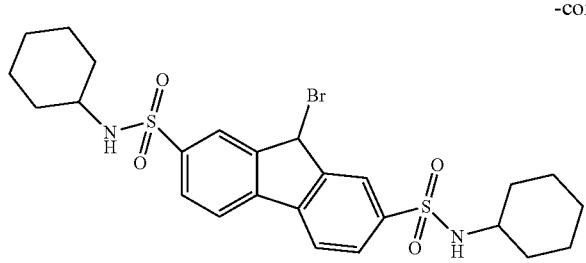
14
-continued
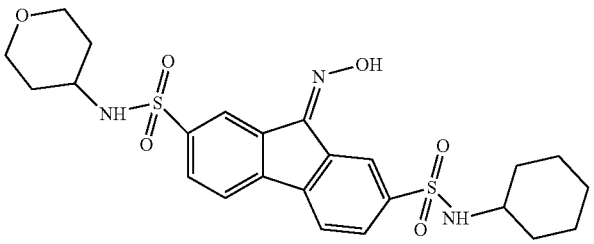
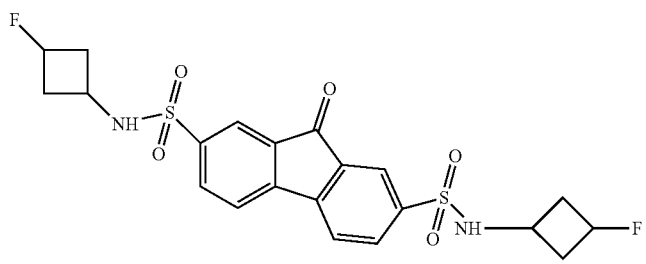
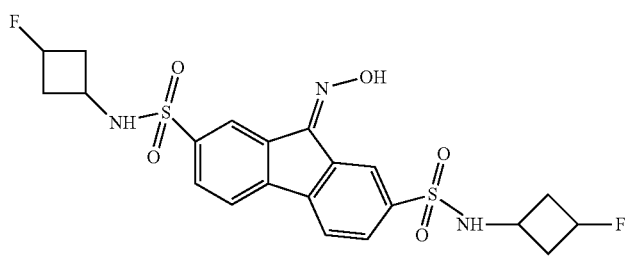
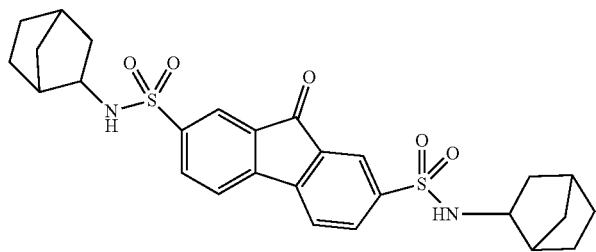
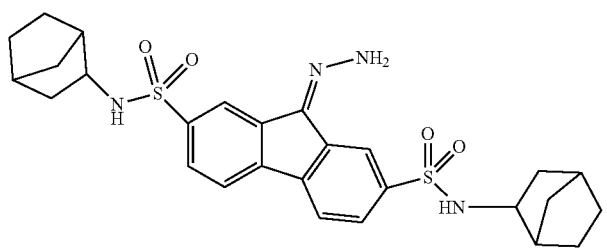
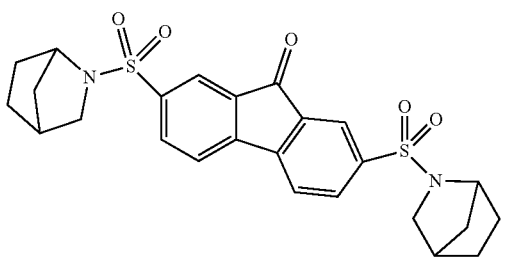
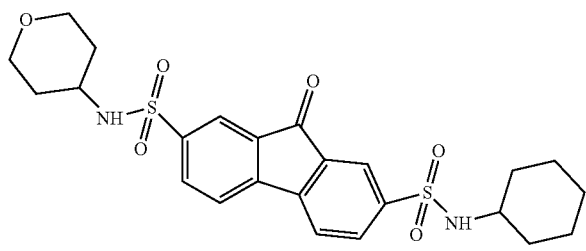

-continued
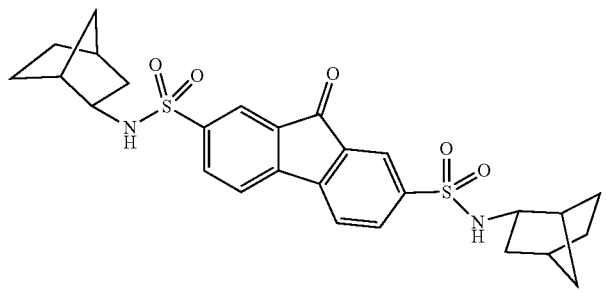
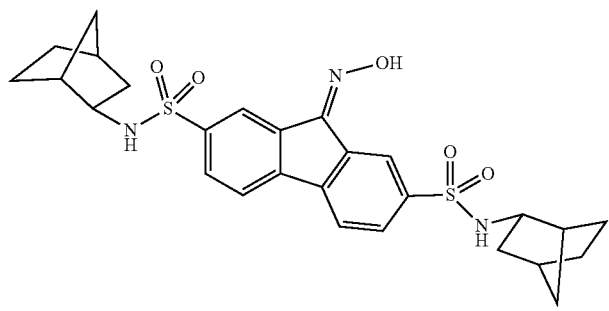
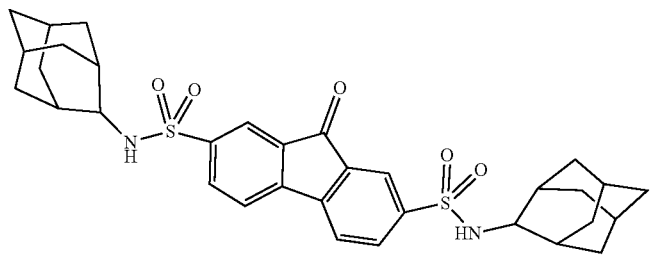
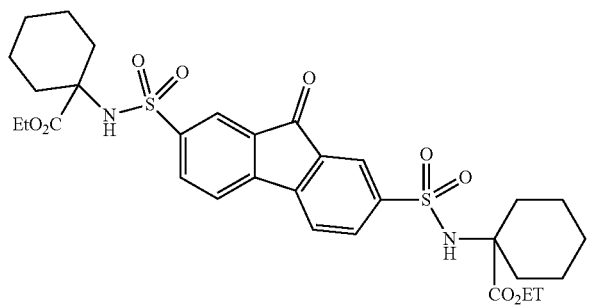
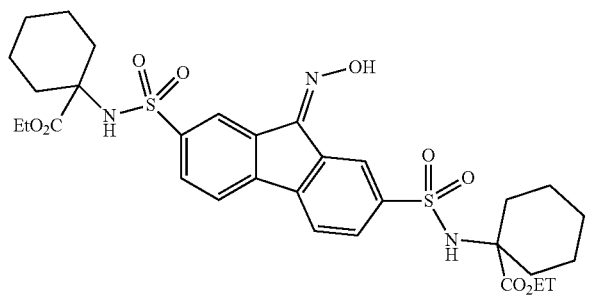
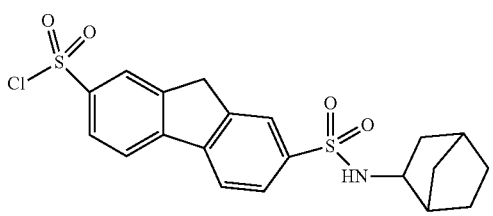
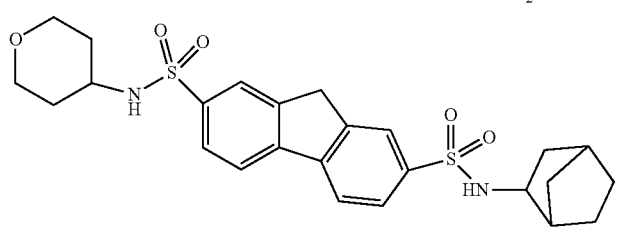

17
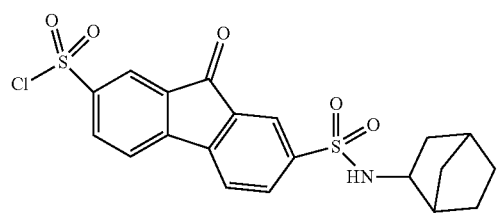
-continued
18
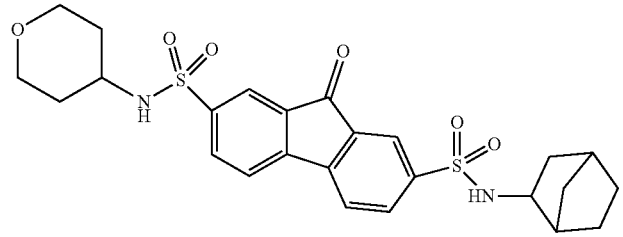
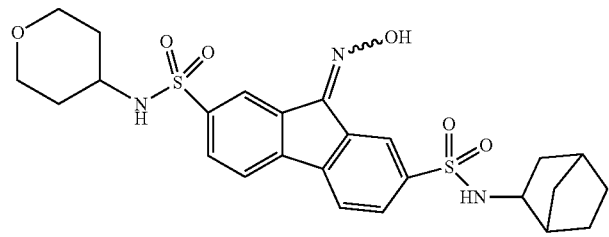
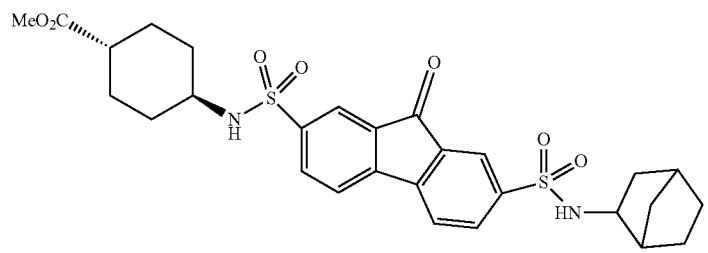
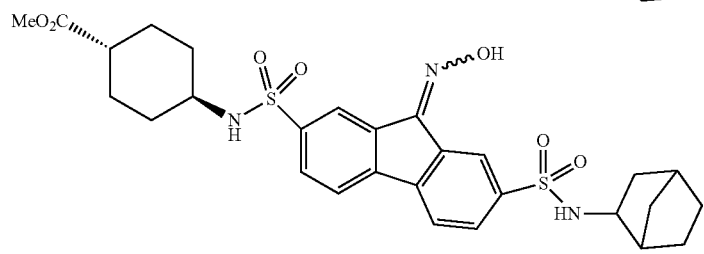
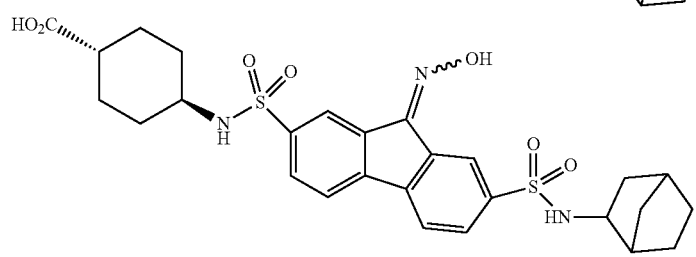
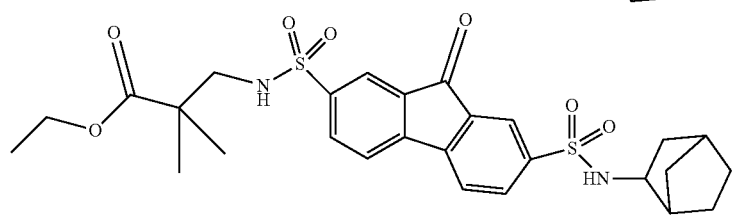
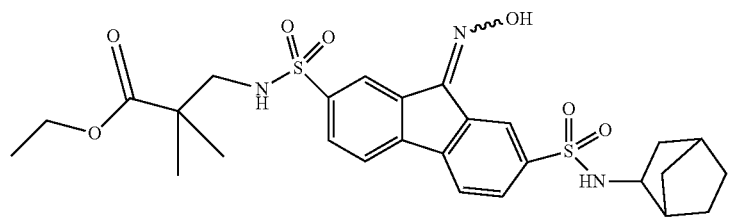

-continued
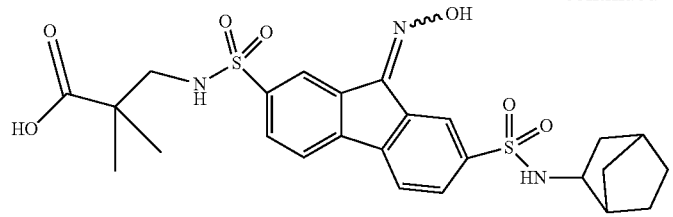
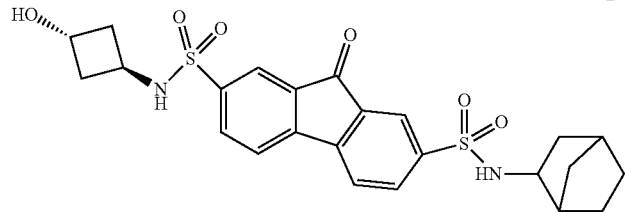
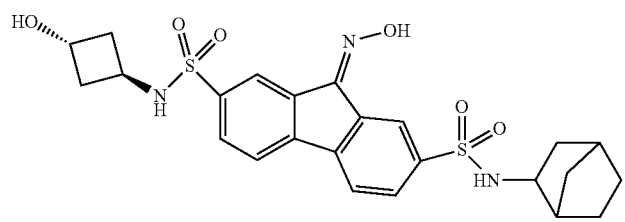
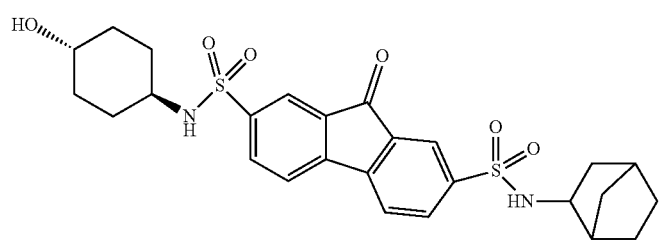
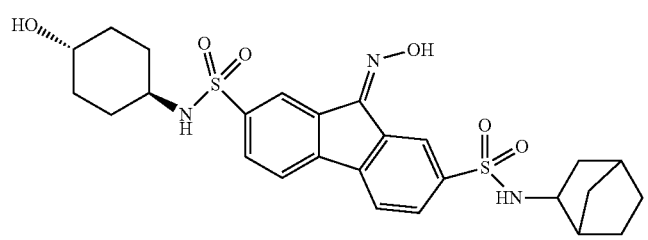
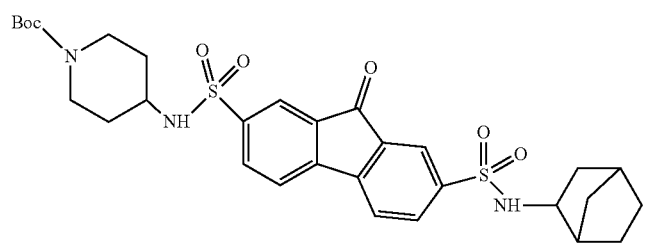
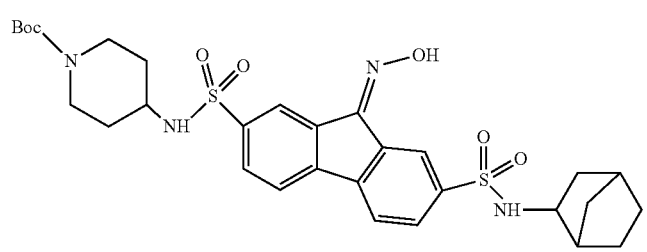

-continued
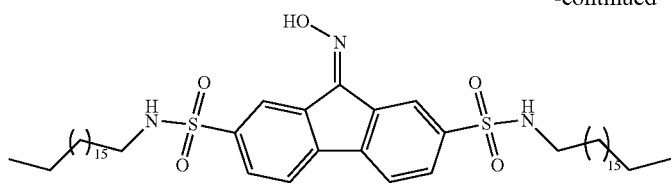
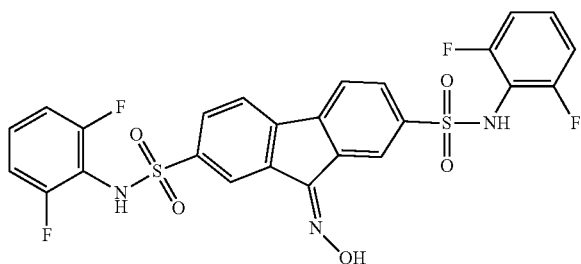
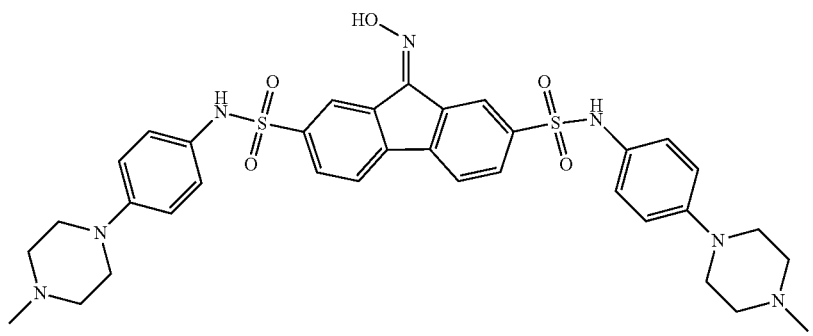
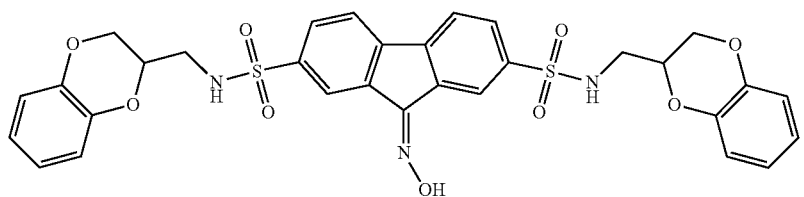
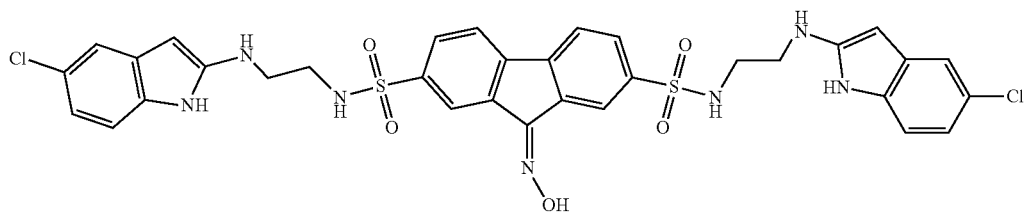
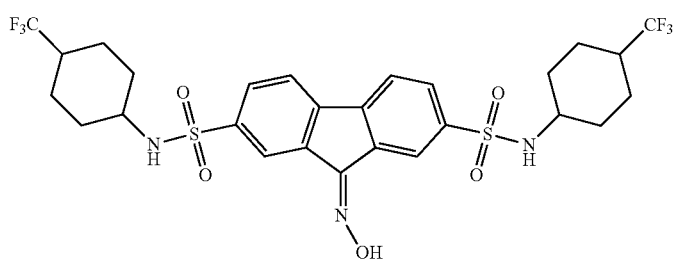

23
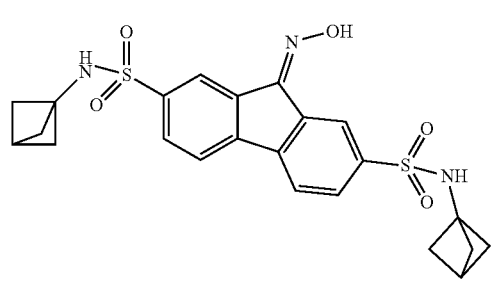
24
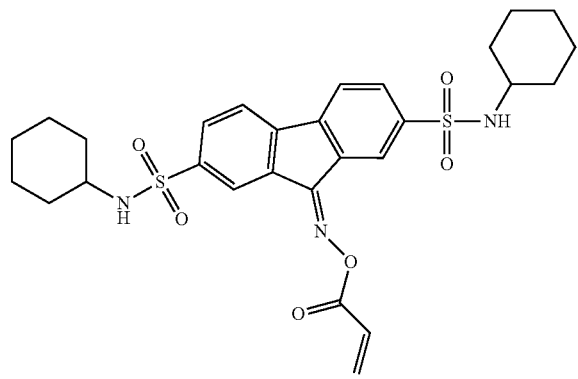
-continued
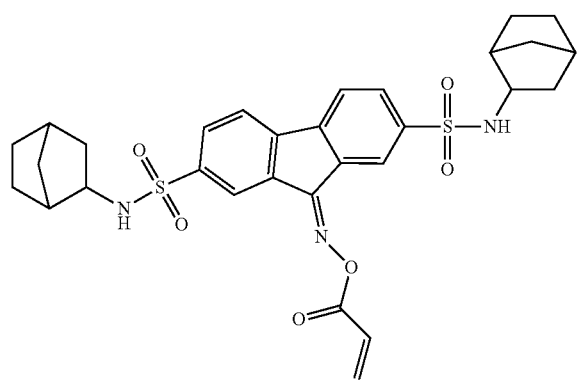
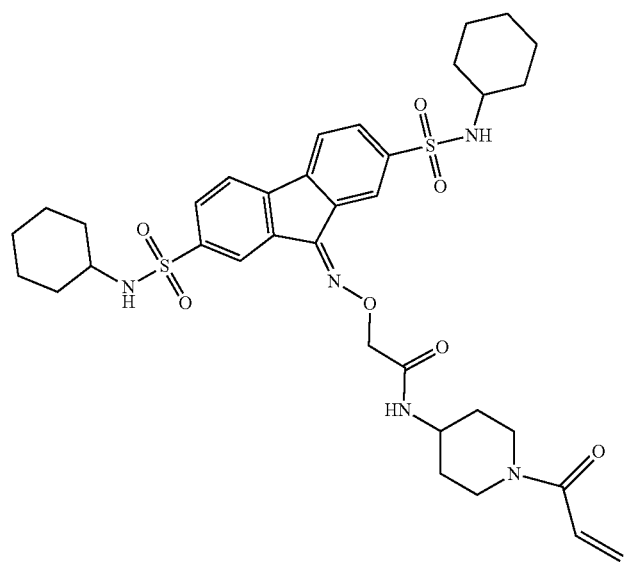
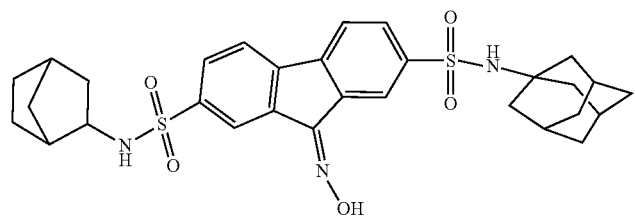

-continued
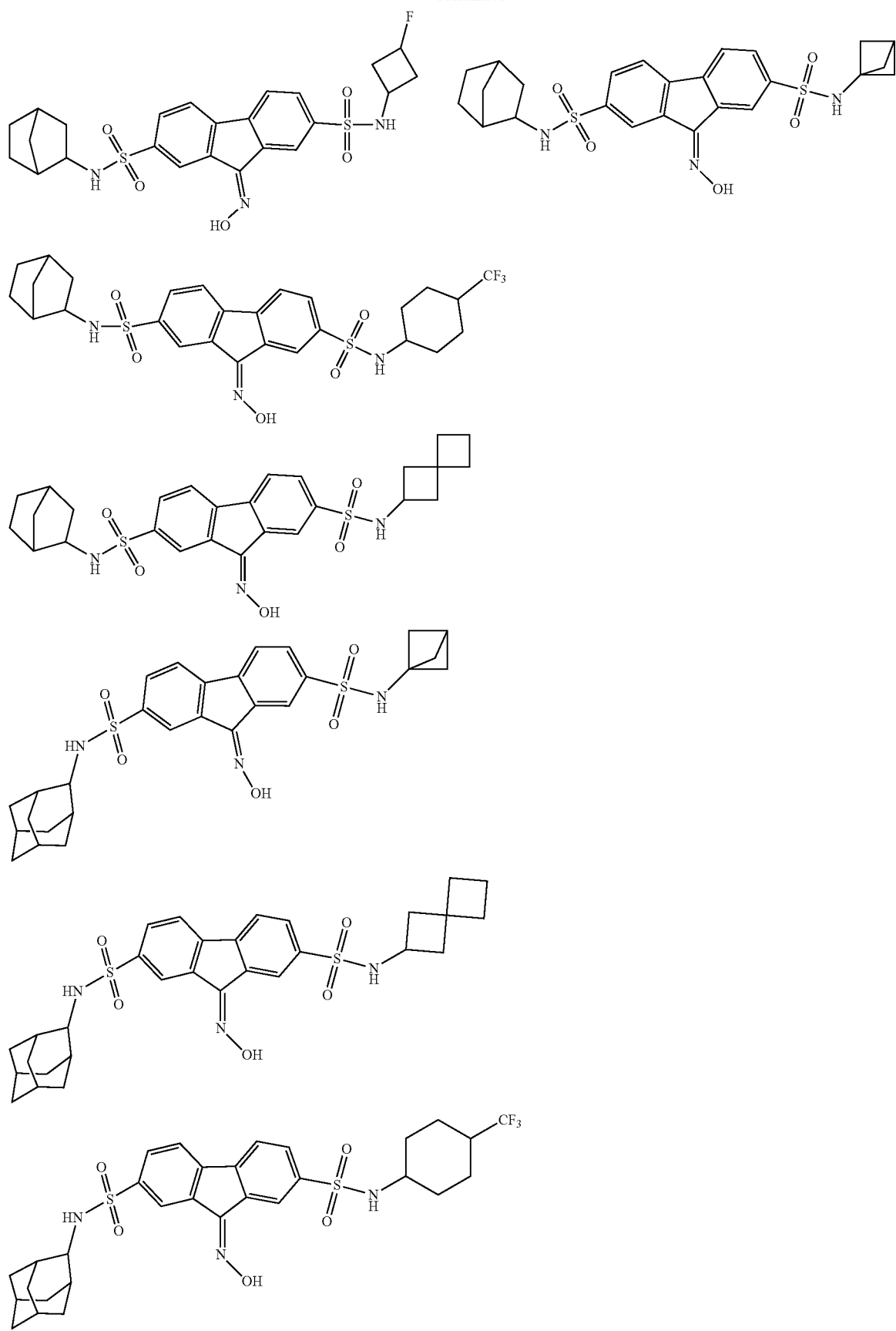

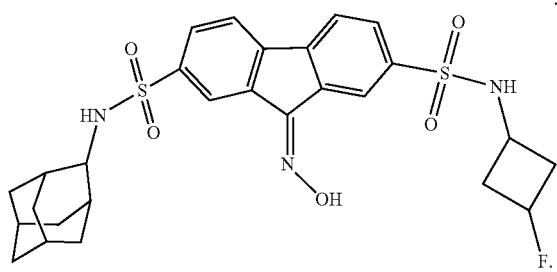

In some aspects, the compound can have a half maximal effective concentration ($EC_{50}$) of less than 2 µM, preferably 0.05 to 1.9 µM, more preferably 0.05 to 0.25 µM, for example, when incubated with HT-1080 cells.

The foregoing compounds can be as shown above or as an N-oxide, crystalline form, hydrate, or pharmaceutically acceptable salt.

As used herein, "N-oxide" refers to a compound containing an N—O bond with three additional hydrogen or side chains attached to the N, so that there is a positive charge on the nitrogen. The N-oxides of the present disclosure can be synthesized by oxidation procedures well known to those skilled in the art.

As used herein, the term "crystalline form" refers to the crystal structure of a compound. A compound can exist in one or more crystalline forms, which can have different structural, physical, pharmacological, or chemical properties. Different crystalline forms can be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

"Hydrate" as used herein refers to a compound that contains water molecules in a defined ratio and in which the water molecules form an integral part of the crystalline structure of the compound. Methods of making hydrates are known in the art. For example, some substances spontaneously absorb water from the air to form hydrates. Others can form hydrates upon contact with water. In other cases, hydrates can be made by changes in temperature or pressure. Additionally, the compounds of the present disclosure as their salts can contain, for example, when isolated in crystalline form, varying amounts of solvents, such as water. Accordingly, the present disclosure includes all hydrate of the compounds and all hydrates of the salts of the compounds disclosed herein, provided that the hydrates do not significantly adversely affect one or more desired property of the compound.

The term "pharmaceutically acceptable salt" refers to a salt of the compound which is pharmaceutically acceptable and which possesses the desired pharmacological activity. Such salts can include, for example, addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-napthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicyclic acid, stearic acid, muconic acid, and the like. Pharmaceutically acceptable salts can also include base addition salts which can be formed when acidic protons present are capable of reacting with inorganic or organic bases. Acceptable inorganic bases can include, for example, sodium hydroxide, sodium carbonate, potassium hydroxide, aluminum hydroxide and calcium hydroxide. Acceptable organic bases can include, for example, ethanolamine, diethanolamine, triethanolamine, tromethamine, N-methylglucamine and the like.

The compound according to the present disclosure is not

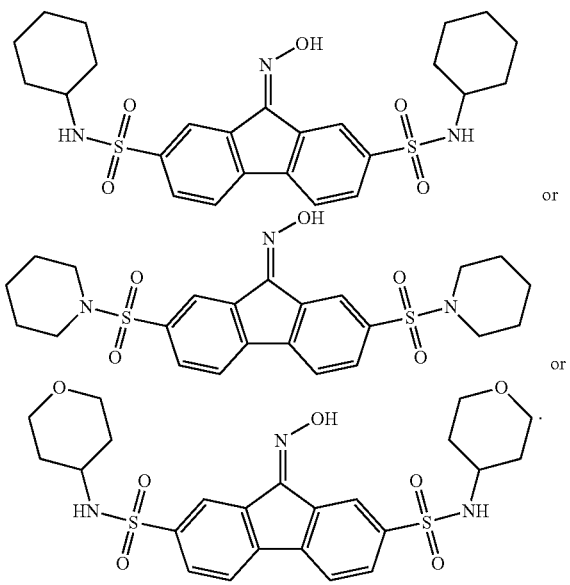

The compound can be used in a composition. The composition therefore includes one or more compounds of the present disclosure and a pharmaceutically acceptable carrier, adjuvant, or vehicle. Optionally, one or more other compounds, drugs, ingredients or other materials or additives can be included in the composition. Regardless of the route of administration selected (discussed further below) the compounds of the present disclosure are formulated into pharmaceutically-acceptable dosage forms by conventional methods. "Pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers are generally known and can be selected by the skilled person without undue experimentation. Pharmaceutically acceptable carriers can include, for example, sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradeable polymers (e.g., polylactide-polyglycolide, poly(orthoesters), and poly(anhdyrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, salicylate, and the like, or combinations thereof. Each pharmaceutically acceptable carrier used in the composition must be "acceptable" in the sense of being compatible with the other ingredients of the compositions and not injurious to the subject. Carriers suitable for a selected dosage form and intended route of administration are generally known in the art, and acceptable carriers for a chosen dosage form and method of administration can be determined using ordinary skill in the art.

The composition can be administered in any desired and effective manner. For example, the composition can be suitable for oral ingestion, or in the form of an ointment or a drop for local administration to the eyes. Also contemplated are compositions suitable for administration intraperitoneally, subcutaneously, topically, intradermally, by inhalation, intrapulmonary delivery, rectally, vaginally, sublingually, intramuscularly, intravenously, intraarterially, intrathecally, or intralymphatically. A composition of the present disclosure can also optionally be administered in conjunction with other treatments. The composition can optionally be encapsulated or otherwise protected against gastric or other secretions. The composition can also optionally contain one or more of inert diluents, fillers, extenders, binders, humectants, disintegrating agents, solution retarding agents, absorption accelerators, wetting agents, absorbents, lubricants, coloring agents, preservatives, sweetening, and perfuming.

Routes of administration of the composition and additives or adjuvants that can be present in the composition can be, for example, as described in U.S. Publication No. 2019/0315681, the contents of which are incorporated by reference herein in its entirety.

Another aspect of the present disclosure is a method for inducing ferroptosis in a cell. The method comprises contacting the cell with an effective amount of a compound of Formula 1, as described above.

As used herein, "ferroptosis" refers to regulated cell death that is iron-dependent. Ferroptosis is characterized by the overwhelming, iron-dependent accumulation of lethal lipid reactive oxygen species. Ferroptosis is distinct from apoptosis, necrosis, and autophagy. Assays for ferroptosis can be, for example, as described in Dixon, S. J., et al. Ferroptosis: An Iron-Dependent Form of Nonapoptotic Cell Death, Cell (2012) 149, 1060-1072. Preferred compounds that fall within the scope of Formula 1 are described above.

In an aspect, the cell is mammalian, preferably human. In an aspect, the cell can be from a laboratory animal. In addition to human, other mammals can include, for example, agricultural animals (e.g., cows, pigs, horses, goats), veterinary animals (e.g., dogs, cats), laboratory animals (e.g., mice, rats, rabbits, guinea pigs), and the like.

In an aspect, the method of inducing ferroptosis can be carried out in vitro. In an aspect, the method can be carried out in vivo. In vitro refers to a process performed in an artificial environment created outside a living multicellular organism (e.g., a test tube or a culture plate) used in experimental research to study a disease or process. In vitro processes can include those performed in intact cells growing in culture. In vivo refers to the method taking place inside an organism and more specifically to a process performed in or on the living tissue of a whole, living multicellular organism (e.g., an animal), as opposed to a partial or dead one. Ex vivo refers to a process performed in an artificial environment outside the organism on living cells or tissue which are removed from an organism and subsequently returned to an organism.

This disclosure is further illustrated by the following examples, which are non-limiting.

EXAMPLES

The following materials and methods were used in conducting the examples.

Biology. Deferoxamine mesylate, Trolox, alpha-tocopherol and sodium selenite were purchased from Sigma-Aldrich. Ebselen and TOFA were purchased from Cayman Chemical. Zvad was purchased from Tocris Bioscience. Fer-1 was created and purified in the laboratory based on Skouta et al., J. Am. Chem. Soc., 2014, 136, 4551-4556.

Cell lines and media. In the following example, HT-1080 (Human fibrosarcoma harboring NrasQ61K) cells (obtained from ATCC) were grown in DMEM high-glucose media with 1% non-essential amino acids (Life Technologies) and 10% FBS. 143B cells were grown in DMEM high-glucose media with 1% glutamine and 10% FBS. Calu-1 cells were grown in McCoy's 5A media (Life Technologies) supplemented with 10% FBS. All the cell lines were grown at 37° C. under 5% CO2. Cell lines were not tested for mycoplasma. In addition, the panel of four lung cancer (NCI-H23; SK-Mes-1; Calu6 and A549) were purchased from ATCC. They were cultured according to the ATCC protocol of each cell line. The non-malignant breast epithelial cells (MCF10A) were maintained in DMEM/F12 medium supplemented with 5% horse serum, epidermal growth factor (20 ng/ml), insulin (10 µg/ml), hydrocortisone (0.5 mg/ml), cholera toxin (100 ng/ml), and penicillin/streptomycin.

Cell viability assay. 9,000 cells per 100 µl were seeded in each well in 96-well plates. Lethal compounds were dissolved in DMSO. In the mother plates, DMSO stock of each compound was further diluted with media to create 20 µM or 10 µm as highest concentrations, respectively and a twofold, 9-point dilution series was prepared. Cells were seeded for 24 h and media were replaced by the mother plate drug-dilution media. When ferroptosis inhibitors (for example, 500 nM Ferrostatin-1, 100 μM α-tocopherol, 152 μM deferoxamine) were used in cotreatments with lethal inducers, they were supplemented to cell culture when the lethal compounds were added, and the cells were then incubated for 48 h. When other cell-death-modulating compounds (100 nM sodium selenite) were used in cotreatments, they were supplemented to cell culture for 24 h before lethal compounds were added to cell culture, after which cells were further incubated for 48 h at 37° C. under 5% CO2. On the day of the viability measurement, we added 25 μl per well of 50% Alamar Blue diluted in media (Life Technologies) and further incubated the cells at 37° C. for 6 h. Fluorescence intensity (excitation/emission: 540/590) was measured with a Victor 3 plate reader (PerkinElmer), and the normalized viability was calculated as VL=(IL−I0)/(IV−I0), where VL is the normalized viability, I0 is the raw fluorescence intensities from the wells containing media, IV is the cells treated with a vehicle (negative control), and IL is the cells cells with the lethal compound (L), respectively. The viability was typically measured in at least biological duplicate. A representative dose-response curve, the mean and standard error of normalized viability from one replicate were plotted.

Analysis of ROS Generation. 200,000 HT-1080 cells were seeded in six-well plates at 37° C. for 17 h. Cells were treated with TKD1079 compound, trypsinized, pelleted, and washed once with PBS. For lipophilic or aqueous ROS detection, cells were re-suspended in Hanks' Balanced Salt Solution (HBSS; Life Technologies) containing test compounds as well as C11-BODIPY(581/591) (2 μM) (Life Technologies), and incubated for 10 min at 37° C. Cells were then pelleted, re-suspended in 250 μL HBSS in a BD Falcon tube, and analyzed using a BD Accuri C6 flow cytometer (BD Biosciences). Both dyes were measured in the FL1 channel.

Statistical analysis and data visualization. Dose-response curve plotting and EC50 computation were performed with Prism 6.0c (GraphPad Software).

Synthesis. Building blocks for the creation of compounds according to the present disclosure were purchased from Enamine, Fisher, Matrix Scientific and Sigma-Aldrich. The purity of the purchased compounds was not assessed. The compounds were synthesized based on previously described synthetic route (Shimada et al., Nat. Chem. Biol. 2016, 12(7): 497-503)). The total synthesis of exemplary compounds and their $^1$H NMR data are described below.

FIG. 1 shows a general scheme for the synthesis of exemplary compounds of the present disclosure.

General Procedure A: Preparation of Ketone Compounds. 9-oxo-9H-fluorene-2,7-disulfonyl dichloride (3) or the appropriate disulfonyl chloride (1.0 eq.) was dissolved in DCM (0.016M) and this solution was cooled to 0° C. A primary or secondary amine (2.6 eq) was then added to this solution, followed by dropwise addition of diisopropylethylamine (4.8 eq.). The reaction mixture was then allowed to warm to room temperature and stirred for 30 min or until complete by TLC. Upon completion, the solvent was evaporated and the residue purified by column chromatography (DCM/MeOH) to afford the ketone products (4).

General Procedure B: Preparation of Oxime Products. A mixture of ketone product (4) from General Procedure A (1.0 eq.); hydroxylamine hydrochloride or an alkoxylamine hydrochloride (15-25 eq.); and sodium hydroxide (15-25 eq) were dissolved in an EtOH:H$_2$O solvent mixture (9:1, 0.016 M). The reaction mixture was heated at 78 0° C. for 72 h. Upon completion, the solvent was evaporated, and the residue purified by column chromatography (DCM/MeOH) to afford the oxime products (7).

General Procedure C: Preparation of Mono-Substituted Sulfonamides. 9-oxo-9H-fluorene-2,7-disulfonyl dichloride (3, 1.0 eq.) or 9H-fluorene-2,7-disulfonyl dichloride (1.0 eq.) was dissolved in DCM (0.032 M) and this solution was cooled to 0° C. A separate solution containing a secondary amine (1.0 eq) and diisopropylethylamine (2.5 eq) dissolved in DCM (0.032 M) was made; this solution was added dropwise to the first solution over 1 h. Upon completion, the solvent was evaporated and the residue purified by column chromatography (DCM/MeOH) to afford (5).

General Procedure D: Preparation of Non-Symmetrical Sulfonamides. Mono-substituted sulfonamides (5, 1.0 eq.) was dissolved in DCM (0.016M) and this solution was cooled to 0° C. A secondary amine (1.5-3.0 eq.) was then added to this solution, followed by dropwise addition of diisopropylethylamine (3.0-4.5 eq.). The reaction mixture was then allowed to warm to room temperature and stirred for 30 min or until complete by TLC. Upon completion, the solvent was evaporated and the residue purified by column chromatography (DCM/MeOH) to afford (6) (in which R≠R').

General Procedure E: Saponification of Esters to Carboxylic Acids. The ester-containing molecule (1.0 eq.) was dissolved in dioxane (0.010 M) and a solution of 2 M sodium hydroxide (80-100 eq.) was added. The reaction mixture stirred at r.t. for three days or until consumption of the starting material was evident by TLC. Upon completion, the reaction mixture was acidified to pH=3 using 1 M HCl, then evaporated and purified by column chromatography (DCM/MeOH) to afford the carboxylic acid products.

$N^2,N^7$-dicyclohexyl-9-oxo-9H-fluorene-2,7-disulfonamide (TKD1058). 9-oxo-9H-fluorene-2,7-disulfonyl dichloride (500 mg, 1.3 mmol) and cyclohexylamine (0.39 mL, 3.4 mmol) were coupled according to General Procedure A. Yield: 522 mg, 78%. $^1$H NMR (400 MHz, DMSO) δ 8.13; (t, J=5.8 Hz, 4H), 8.00; (s, 2H), 7.85; (d, J=7.2 Hz, 2H), 2.99; (s, 2H), 1.58; (d, J=10.1 Hz, 8H), 1.44; (d, J=12.0 Hz, 2H), 1.12; (d, J=9.8 Hz, 10H).

N2,$N^7$-dicyclohexyl-9-hydroxy-9H-fluorene-2,7-disulfonamide (TKD1011). TKD1058 (35 mg, 0.07 mmol) was dissolved in ethanol (5 mL) and the solution was cooled to 0° C. Sodium borohydride (28 mg, 0.72 mmol) was carefully added and the reaction stirred for 1 h. Upon completion, the solvent was evaporated and the residue purified by column chromatography (DCM/MeOH) to afford the title product. Yield: 110 mg, 82%. $^1$H NMR (400 MHz, DMSO) δ 8.08; (d, J=8.0 Hz, 2H), 8.03; (d, J=1.7 Hz, 2H), 7.89; (dd, J=7.9, 1.7 Hz, 2H), 7.73; (d, J=7.2 Hz, 2H), 6.26; (d, J=7.4 Hz, 1H), 5.69; (d, J=7.3 Hz, 1H), 2.96; (dq, J=11.1, 6.9, 5.5 Hz, 2H), 1.68-1.53; (m, 8H), 1.44; (d, J=12.0 Hz, 2H), 1.21-0.96; (m, 10H).

$N^2,N^7$-bis(cyclopentylmethyl)-9-oxo-9H-fluorene-2,7-disulfonamide (TKD1070). 9-oxo-9H-fluorene-2,7-disulfonyl dichloride (25 mg, 0.07 mmol) and cyclopentylmethylamine hydrochloride (23 mg, 0.17 mmol) were coupled according to General Procedure A. Yield: 17 mg, 25%. $^1$H NMR (400 MHz, DMSO) δ 8.15; (d, J=7.9 Hz, 2H), 8.09; (dd, J=7.9, 1.7 Hz, 2H), 7.98; (d, J=1.7 Hz, 2H), 7.82; (s, 2H), 2.69; (d, J=7.2 Hz, 4H), 1.92; (hept, J=7.5 Hz, 2H), 1.60; (ddd, J=11.8, 9.0, 4.7 Hz, 5H), 1.55-1.38; (m, 6H), 1.12; (dq, J=11.1, 7.1 Hz, 5H).

$N^2,N^7$-bis(cyclopentylmethyl)-9-(hydroxyimino)-9H-fluorene-2,7-disulfonamide (TKD1013). TKD1070 (17 mg, 0.03 mmol), hydroxylamine hydrochloride (35 mg, 0.51 mmol), and sodium hydroxide (20 mg, 0.51 mmol) reacted according to General Procedure B. Yield: 8 mg, 44%. $^1$H NMR (400 MHz, DMSO) δ 13.28 (s, 1H), 8.78; (d, J=1.7 Hz, 1H), 8.23; (d, J=8.0 Hz, 1H), 8.19; (d, J=8.0 Hz, 1H), 8.12; (d, J=1.6 Hz, 1H), 7.99; (dd, J=8.1, 1.8 Hz, 1H), 7.91; (dd, J=7.9, 1.7 Hz, 1H), 7.81; (t, J=5.9 Hz, 1H), 7.77; (t, J=6.0 Hz, 1H), 2.69; (t, J=6.6 Hz, 4H), 1.92; (hept, J=7.4 Hz, 2H), 1.60; (dq, J=12.0, 6.2, 5.3 Hz, 4H), 1.55-1.38; (m, 8H), 1.13; (p, J=6.1 Hz, 4H).

$N^2,N^7$-dicyclohexyl-9-((prop-2-yn-1-yloxy)imino)-9H-fluorene-2,7-disulfonamide (TKD1020). TKD1058 (40 mg, 0.08 mmol), O-(prop-2-yn-1-yl)hydroxylamine hydrochloride (128 mg, 1.2 mmol), and sodium hydroxide (48 mg, 1.2 mmol) reacted according to General Procedure B. Yield: 12 mg, 27%. $^1$H NMR (400 MHz, DMSO) δ 8.63; (d, J=1.7 Hz, 1H), 8.23; (d, J=8.0 Hz, 1H), 8.18; (d, J=8.0 Hz, 1H), 8.14; (d, J=1.6 Hz, 1H), 8.07; (dd, J=8.0, 1.7 Hz, 1H), 7.98; (dd, J=7.9, 1.7 Hz, 1H), 7.89; (d, J=7.4 Hz, 1H), 7.82; (d, J=7.3 Hz, 1H), 5.17; (d, J=2.4 Hz, 2H), 3.71; (t, J=2.4 Hz, 1H), 3.00; (s, 2H), 1.57; (d, J=8.0 Hz, 9H), 1.44; (d, J=12.1 Hz, 2H), 1.14; (q, J=9.0, 8.4 Hz, 9H).

$N^2,N^7$-di(bicyclo[1.1.1]pentan-1-yl)-9-oxo-9H-fluorene-2,7-disulfonamide (MM1006). 9-oxo-9H-fluorene-2,7-disulfonyl dichloride (30 mg, 0.08 mmol) and the bicyclo[1.1.1]pentan-1-amine hydrochloride (25 mg, 0.21 mmol) were coupled according to General Procedure A. Yield: 12 mg, 32%. $^1$H NMR (400 MHz, DMSO) δ 8.81; (s, 2H), 8.19-8.09; (m, 4H), 8.00; (d, J=1.6 Hz, 2H), 2.29; (s, 2H), 1.75; (s, 12H).

$N^2,N^7$-di(bicyclo[1.1.1]pentan-1-yl)-9-(hydroxyimino)-9H-fluorene-2,7-disulfonamide (TKD1026). MM1006 (12 mg, 0.03 mmol), hydroxylamine hydrochloride (27 mg, 0.38 mmol), and sodium hydroxide (16 mg, 0.38 mmol) reacted according to General Procedure B. Yield: 8 mg, 67%. $^1$H NMR (400 MHz, DMSO) δ 13.30; (s, 1H), 8.81; (d, J=1.8 Hz, 1H), 8.79; (s, 1H), 8.76; (s, 1H), 8.24; (d, J=8.0 Hz, 1H), 8.20; (d, J=8.0 Hz, 1H), 8.15; (d, J=1.7 Hz, 1H), 8.02; (dd, J=8.0, 1.8 Hz, 1H), 7.94; (dd, J=8.0, 1.7 Hz, 1H), 2.28; (d, J=2.0 Hz, 2H), 1.74; (d, J=3.8 Hz, 12H).

$N^2,N^7$-bis(2-fluoroethyl)-9-oxo-9H-fluorene-2,7-disulfonamide (TKD1023). 9-oxo-9H-fluorene-2,7-disulfonyl dichloride (50 mg, 0.13 mmol) and 2-fluoroethan-1-amine hydrochloride (34 mg, 0.35 mmol) were coupled according to General Procedure A. Yield: 26 mg, 46%. $^1$H NMR (400 MHz, DMSO) δ 8.22-8.14; (m, 4H), 8.11; (dd, J=7.9, 1.7 Hz, 2H), 8.00; (d, J=1.5 Hz, 2H), 4.46; (t, J=4.9 Hz, 2H), 4.34; (t, J=4.9 Hz, 2H), 3.17; (q, J=5.0 Hz, 2H), 3.10; (q, J=5.0 Hz, 2H).

$N^2,N^7$-bis(2-fluoroethyl)-9-(hydroxyimino)-9H-fluorene-2,7-disulfonamide (TKD1027). TKD1023 (26 mg, 0.06 mmol), hydroxylamine hydrochloride (61 mg, 0.88 mmol), and sodium hydroxide (35 mg, 0.88 mmol) reacted according to General Procedure B. Yield: 5 mg, 19%. $^1$H NMR (400 MHz, DMSO) δ 13.31; (s, 1H), 8.79; (d, J=1.7 Hz, 1H), 8.26; (d, J=8.0 Hz, 1H), 8.21; (d, J=8.0 Hz, 1H), 8.18-8.09; (m, 3H), 8.02; (dd, J=8.0, 1.7 Hz, 1H), 7.94; (dd, J=8.0, 1.6 Hz, 1H), 4.45; (td, J=4.9, 2.0 Hz, 2H), 4.33; (td, J=4.9, 2.0 Hz, 2H), 3.18-3.12; (m, 2H), 3.08; (q, J=5.3 Hz, 2H).

$N^2,N^7$-dimethyl-9-oxo-9H-fluorene-2,7-disulfonamide (TKD1032A). 9-oxo-9H-fluorene-2,7-disulfonyl dichloride (100 mg, 0.27 mmol) and methylamine (60 mL, 0.69 mmol) were coupled according to General Procedure A. Yield 29 mg, 30%. $^1$H NMR (400 MHz, DMSO) δ 8.19; (d, J=7.8 Hz, 2H), 8.09; (dd, J=7.8, 1.7 Hz, 2H), 7.97; (d, J=1.6 Hz, 2H), 7.67; (s, 2H), 2.46; (d, J=3.0 Hz, 6H).

9-(hydroxyimino)-$N^2,N^7$-dimethyl-9H-fluorene-2,7-disulfonamide (TKD1034A). TKD1032A (29 mg, 0.08 mmol), hydroxylamine hydrochloride (138 mg, 2.0 mmol), and sodium hydroxide (79 mg, 2.0 mmol) reacted according to General Procedure B. Yield: 11 mg, 37%. $^1$H NMR (400 MHz, DMSO) δ 13.33; (s, 1H), 8.77; (s, 1H), 8.27; (d, J=8.0 Hz, 1H), 8.22; (d, J=7.9 Hz, 1H), 8.11; (s, 1H), 7.98; (d, J=8.2 Hz, 1H), 7.91; (d, J=8.0 Hz, 1H), 7.63; (dt, J=13.8, 5.2 Hz, 2H), 2.45; (d, J=4.5 Hz, 6H).

9-oxo-$N^2,N^7$-di(pentan-3-yl)-9H-fluorene-2,7-disulfonamide (TKD1032D). 9-oxo-9H-fluorene-2,7-disulfonyl dichloride (100 mg, 0.27 mmol) and 3-aminopentane (80 mL, 0.69 mmol) were coupled according to General Procedure A. Yield: 110 mg, 87%. $^1$H NMR (400 MHz, DMSO) δ 8.11; (qd, J=7.9, 1.2 Hz, 4H), 7.98; (d, J=1.6 Hz, 2H), 7.72; (d, J=7.9 Hz, 2H), 3.01; (hept, J=6.1, 5.6 Hz, 2H), 1.37; (ddd, J=13.5, 7.5, 5.8 Hz, 4H), 1.26; (dt, J=14.1, 7.2 Hz, 4H), 0.68; (t, J=7.4 Hz, 12H).

9-(hydroxyimino)-$N^2,N^7$-di(pentan-3-yl)-9H-fluorene-2,7-disulfonamide (TKD1034D). TKD1032D (110 mg, 0.23 mmol), hydroxylamine hydrochloride (400 mg, 5.8 mmol), and sodium hydroxide (230 mg, 5.8 mmol) reacted according to General Procedure B. Yield: 78 mg, 69%. $^1$H NMR (400 MHz, DMSO) δ 13.26; (s, 1H), 8.79; (d, J=1.7 Hz, 1H), 8.20; (d, J=8.0 Hz, 1H), 8.16; (d, J=8.1 Hz, 1H), 8.12; (d, J=1.6 Hz, 1H), 8.00; (dd, J=7.9, 1.8 Hz, 1H), 7.92; (dd, J=8.1, 1.7 Hz, 1H), 7.69; (d, J=8.0 Hz, 1H), 7.65; (d, J=7.9 Hz, 1H), 3.00; (h, J =6.5 Hz, 2H), 1.36; (dp, J=14.4, 7.5 Hz, 4H), 1.25; (dt, J=14.1, 7.1 Hz, 4H), 0.67; (td, J=7.3, 1.4 Hz, 12H).

9-oxo-$N^2,N^7$-dipropyl-9H-fluorene-2,7-disulfonamide (DA1007). 9-oxo-9H-fluorene-2,7-disulfonyl dichloride (200 mg, 0.53 mmol) and propylamine (110 mL, 1.4 mmol) were coupled according to General Procedure A. Yield: 224 mg, 85%. $^1$H NMR (400 MHz, DMSO) δ 8.16; (d, J=7.9 Hz, 2H), 8.09; (dd, J=7.9, 1.7 Hz, 2H), 7.98; (d, J=1.7 Hz, 2H), 7.80; (t, J=5.9 Hz, 2H), 2.74; (td, J=7.1, 5.8 Hz, 4H), 1.39; (h, J=7.3 Hz, 4H), 0.80; (t, J=7.4 Hz, 6H).

9-(hydroxyimino)-$N^2,N^7$-dipropyl-9H-fluorene-2,7-disulfonamide (TKD1034E). DA1007 (100 mg, 0.24 mmol), hydroxylamine hydrochloride (411 mg, 5.9 mmol), and sodium hydroxide (240 mg, 6.0 mmol) reacted according to General Procedure B. Yield: 104 mg, 70%. $^1$H NMR (400 MHz, DMSO) δ 13.29; (s, 1H), 8.78; (d, J=1.7 Hz, 1H), 8.24; (d, J=8.0 Hz, 1H), 8.20; (d, J=8.0 Hz, 1H), 8.12; (d, J=1.6 Hz, 1H), 7.99; (dd, J=8.0, 1.8 Hz, 1H), 7.91; (dd, J=8.0, 1.7 Hz, 1H), 7.77; (t, J=5.9 Hz, 1H), 7.73; (t, J=5.9 Hz, 1H), 2.74; (q, J=6.7 Hz, 4H), 1.38; (hd, J=7.3, 2.1 Hz, 4H), 0.79; (td, J=7.4, 2.1 Hz, 6H).

$N^2,N^7$-diisobutyl-9-oxo-9H-fluorene-2,7-disulfonamide (TKD1038D). 9-oxo-9H-fluorene-2,7-disulfonyl dichloride (100 mg, 0.27 mmol) and isopropylamine (69 mL, 0.69 mmol) were coupled according to General Procedure A. Yield: 119 mg, 100%. $^1$H NMR (400 MHz, DMSO) δ 8.16; (d, J=7.9 Hz, 2H), 8.09; (dd, J=7.9, 1.7 Hz, 2H), 7.98; (d, J=1.5 Hz, 2H), 7.82; (t, J=6.1 Hz, 2H), 2.59; (t, J=6.4 Hz, 4H), 1.64; (hept, J=6.7 Hz, 2H), 0.82; (d, J=6.6 Hz, 12H).

9-(hydroxyimino)-$N^2,N^7$-diisobutyl-9H-fluorene-2,7-disulfonamide (TKD1041B). TKD1038D (119 mg, 0.26 mmol), hydroxylamine hydrochloride (495 mg, 7.1 mmol), and sodium hydroxide (290 mg, 7.3 mmol) reacted according to General Procedure B. 80 mg, Yield: 66%. $^1$H NMR (400 MHz, DMSO) δ 13.31; (s, 1H), 8.78; (d, J=1.6 Hz, 1H), 8.23; (d, J=8.0 Hz, 1H), 8.19; (d, J=8.1 Hz, 1H), 8.12; (s, 1H), 7.99; (dd, J=7.9, 1.7 Hz, 1H), 7.91; (dd, J=7.9, 1.6 Hz, 1H), 7.80; (t, J=6.1 Hz, 1H), 7.75; (t, J=6.1 Hz, 1H), 2.58; (t, J=6.4 Hz, 4H), 1.63; (hept, J=6.8 Hz, 2H), 0.81; (dd, J=6.9, 2.1 Hz, 12H).

2,7-bis((2-azaspiro[3.3]heptan-2-yl)sulfonyl)-9H-fluoren-9-one (TKD1073). 9-oxo-9H-fluorene-2,7-disulfonyl dichloride (100 mg, 0.27 mmol) and 2-azaspiro[3.3]heptane hydrochloride (92 mg, 0.69 mmol) were coupled according to General Procedure A. Yield: 82 mg, 62%. $^1$H NMR (400 MHz, DMSO) δ 8.31; (d, J=7.9 Hz, 2H), 8.14; (dd, J=7.8, 1.7 Hz, 2H), 7.90; (d, J=1.6 Hz, 2H), 3.73; (s, 8H), 1.91; (t, J=7.6 Hz, 8H), 1.64 (p, J=7.9 Hz, 4H).

2,7-bis((2-azaspiro[3.3]heptan-2-yl)sulfonyl)-9H-fluoren-9-one oxime (TKD1077). TKD1073 (82 mg, 0.16 mmol), hydroxylamine hydrochloride (289 mg, 4.1 mmol), and sodium hydroxide (160 mg, 4.1 mmol) reacted according to General Procedure B. Yield: 69 mg, 82%. $^1$H NMR (400 MHz, DMSO) δ 13.45; (s, 1H), 8.71; (d, J=0.9 Hz, 1H), 8.40; (d, J=8.0 Hz, 1H), 8.35; (d, J=8.0 Hz, 1H), 8.04; (m, 2H), 7.95; (q, 3.1 Hz, 1H), 3.71; (d, J=Hz, 8H), 1.89; (t, J=7.6 Hz, 8H), 1.64; (q, J=7.6 Hz, 4H).

9-oxo-N$^2$,N$^7$-di(spiro[3.3]heptan-2-yl)-9H-fluorene-2,7-disulfonamide (TKD1074). 9-oxo-9H-fluorene-2,7-disulfonyl dichloride (100 mg, 0.27 mmol) and spiro[3.3]heptan-2-amine hydrochloride (102 mg, 0.69 mmol) were coupled according to General Procedure A. Yield: 128 mg, 91%. $^1$H NMR (400 MHz, DMSO) δ 8.16; (d, J=7.8 Hz, 2H), 8.10; (t, J=1.7 Hz, 2H), 8.08; (d, J=2.5 Hz, 2H), 7.97; (d, J=1.5 Hz, 2H), 3.53; (m, 2H), 2.06; (m, 4H), 1.89; (t, 7.1 Hz, 4H), 1.77; (t, J=6.9 Hz, 4H), 1.70; (m, 8H).

9-(hydroxyimino)-N$^2$,N$^7$-di(spiro[3.3]heptan-2-yl)-9H-fluorene-2,7-disulfonamide (TKD1078). TKD1074 (128 mg, 0.24 mmol), hydroxylamine hydrochloride (422 mg, 6.1 mmol), and sodium hydroxide (240 mg, 6.1 mmol) reacted according to General Procedure B. Yield: 22 mg, 17%. $^1$H NMR (400 MHz, DMSO) δ 13.32; (s, 1H), 8.78; (s, 1H), 8.23; (d, J=8.0 Hz, 1H), 8.19; (d, J=8.1 Hz, 1H), 8.11; (s, 1H), 8.07; (d, J=8.6 Hz, 1H), 8.03; (d, J=8.5 Hz, 1H), 7.99; (dd, J=1.4, 8.0 Hz, 1H), 7.91; (dd, J=1.5, 8.2 Hz, 1H), 3.53; (dsxt, J=8.1, 2.8 Hz, 2H), 2.05; (m, 4H), 1.88; (t, J=7.2 Hz, 4H), 1.77; (t, 6.9 Hz, 4H), 1.69; (m, 8H).

N$^2$,N$^7$-di(bicyclo[2.2.1]heptan-2-yl)-9-oxo-9H-fluorene-2,7-disulfonamide (TKD1075). 9-oxo-9H-fluorene-2,7-disulfonyl dichloride (100 mg, 0.27 mmol) and 2-aminonorbornane hydrochloride (102 mg, 0.69 mmol) were coupled according to General Procedure A. Yield: 112 mg, 80%. $^1$H NMR (400 MHz, DMSO) δ 8.23-8.02; (m, 4H), 7.99; (d, J=1.5 Hz, 2H), 7.87; (d, J=7.0 Hz, 2H), 3.41; (tt, J=8.2, 4.8 Hz, 2H), 2.11-1.96; (m, 4H), 1.73-1.53; (m, 3H), 1.38; (ddq, J=10.8, 6.8, 4.0 Hz, 2H), 1.31-1.22; (m, 6H), 1.16; (qd, J=9.7, 8.1, 3.2 Hz, 3H), 0.81-0.72; (m, 2H).

N$^2$,N$^7$-di(bicyclo[2.2.1]heptan-2-yl)-9-(hydroxyimino)-9H-fluorene-2,7-disulfonamide (TKD1079). TKD1075 (112 mg, 0.21 mmol), hydroxylamine hydrochloride (369 mg, 5.3 mmol), and sodium hydroxide (212 mg, 5.3 mmol) reacted according to General Procedure B. Yield: 24 mg, 21%. $^1$H NMR (400 MHz, DMSO) δ 13.29; (s, 1H), 8.81; (d, J=1.0 Hz, 1H), 8.22; (d, J=8.0 Hz, 1H), 8.18; (d, J=8.0 Hz, 1H), 8.15; (s, 1H), 8.01; (dd, J=1.4, 8.0 Hz, 1H), 7.93; (dd, J=1.2, 8.0 Hz, 1H), 7.88; (d, J=7.0 Hz, 1H), 7.83; (d, J=7.0 Hz, 1H), 3.43; (m, 2H), 2.03; (m, 4H), 1.64; (m, 4H), 1.40; (m, 2H), 1.24; (d, J=9.5 Hz, 2H), 1.16; (q, J=8.7 Hz, 6H), 0.79; (dt, J=2.7, 12.8 Hz, 2H).

9-bromo-N2,N$^7$-dicyclohexyl-9H-fluorene-2,7-disulfonamide (TKD1100). TKD1011 (126 mg, 0.25 mmol) was dissolved in DCM (6.3 mL) and the solution was cooled to 0° C. Phosphorous tribromide (122 mL, 1.25 mmol) was added dropwise. The reaction was allowed to warm to room temperature over the course of 30 min. Then the solvent was evaporated and the residue purified by column chromatography (DCM/MeOH) to afford the title product. Yield: 112 mg, 79%. $^1$H NMR (400 MHz, DMSO) δ 8.19; (d, J=8.0 Hz, 2H), 8.09; (s, 2H), 7.96; (d, J=7.4 Hz, 2H), 7.83; (d, J=7.4 Hz, 2H), 6.73; (s, 1H), 2.99; (s, 2H), 1.59; (d, J=4.9 Hz, 8H), 1.44; (d, J=12.0 Hz, 2H), 1.10; (m, 10H).

9-cyano-N$^2$,N$^7$-dicyclohexyl-9H-fluorene-2,7-disulfonamide (MH1013). TKD1011 (91 mg, 0.18 mmol) was dissolved in DCM (2.7 mL). Trimethylsilylcyanide (48 mL, 0.36 mmol) was added, followed by indium trichloride. The reaction was stirred for 2 h, at which point the solvent was evaporated and the residue purified by column chromatography (DCM/MeOH) to afford the title product. Yield 59 mg, 63%. $^1$H NMR (400 MHz, DMSO) δ 8.11; (d, J=8.5 Hz, 2H), 7.92; (d, J=6.5 Hz, 4H), 7.82; (d, J=7.3 Hz, 2H), 6.00; (s, 1H), 2.96; (m, 2H), 1.60; (m, 8H), 1.44; (d, J=11.1 Hz, 2H), 1.11; (m, 10H).

N$^2$,N$^7$-dicyclohexyl-9-ethynyl-9-hydroxy-9H-fluorene-2,7-disulfonamide (TKD1066). TKD1058 (100 mg, 0.20 mmol) was suspended in THF (0.69 mL) in a sealed vial. Magnesium bromide (0.5 M sol. in THF, 2.4 mL) was added dropwise via syringe. After stirring 4 h, the reaction was quenched with 1 M HCl, extracted into ethyl acetate, washed twice with water and once with brine, and dried over sodium sulfate. The crude product was purified by column chromatography (DCM/MeOH) to afford the title product. Yield: 70 mg, 67%. $^1$H NMR (400 MHz, DMSO) δ 8.09; (d, J=5.4 Hz, 2H), 8.08; (s, 2H), 7.92; (dd, J=1.0, 3.1 Hz, 2H), 7.80; (d, J=7.4 Hz, 2H), 7.09; (s, 1H), 3.58; (s, 1H), 2.98; (m, 2H), 1.59; (d, J=4.1 Hz, 8H), 1.44; (d, J=11.5 Hz, 2H), 1.11; (m, 10H).

N$^2$,N$^7$-bis(3-fluorocyclobutyl)-9-oxo-9H-fluorene-2,7-disulfonamide, mixture of cis- and trans-isomers (TKD1036A). 9-oxo-9H-fluorene-2,7-disulfonyl dichloride (100 mg, 0.27 mmol) and 3-fluorocyclobutan-1-amine hydrochloride (87 mg, 0.69 mmol) were coupled according to General Procedure A. Yield: 128 mg, 76%. $^1$H NMR (400 MHz, DMSO) δ 8.26; (s, 2H), 8.17; (d, J=7.9 Hz, 2H), 8.09; (d, J=8.0 Hz, 2H), 7.97; (d, J=5.4 Hz, 2H), 5.10; (d, J=57.1 Hz, 1H), 4.67; (dt, J=56.1, 6.9 Hz, 2H), 3.89; (t, J=7.2 Hz, 1H), 3.29-3.24; (m, 1H; partially obscured by water peak), 2.39-2.23; (m, 2H), 2.23-2.08; (m, 2H), 1.93; (dd, J=24.3, 9.7 Hz, 3H). MS (ESI) predicted m/z 483.1 [M+H]$^+$.

N$^2$,N$^7$-bis(3-fluorocyclobutyl)-9-(hydroxyimino)-9H-fluorene-2,7-disulfonamide, mixture of cis- and trans- isomers (TKD1037A). TKD1036A (97 mg, 0.20 mmol), hydroxylamine hydrochloride (349 mg, 5.0 mmol), and sodium hydroxide (200 mg, 5.0 mmol) reacted according to General Procedure B. Yield: 36 mg, 36%. $^1$H NMR (400 MHz, DMSO) δ 13.35; (s, 1H), 8.77; (d, J=4.5 Hz, 1H), 8.25; (d, J=8.1 Hz, 2H), 8.21; (d, J=8.2 Hz, 2H), 8.1; (d, J=6.8 Hz, 1H), 8.00; (d, J=8.1 Hz, 1H), 7.91; (d, J=8.1 Hz, 1H), 5.09; (d, J=57.1 Hz, 1H), 4.66; (dp, J=56.6, 6.7 Hz, 2H), 3.89; (s, 1H), 3.26; (s, 1H; partially obscured by water peak), 2.35-2.22; (m, 2H), 2.22-2.07; (m, 2H), 1.93; (dq, J=26.2, 9.1 Hz, 3H). HRMS (ESI): predicted for [M+H]$^+$ C$_{21}$H$_{22}$F$_2$N$_3$O$_5$S$_2$ 498.0969.

N$^2$,N$^7$-di(bicyclo[2.2.1]heptan-2-yl)-9-hydrazineylidene-9H-fluorene-2,7-disulfonamide (TKD2100). TKD1075 (70 mg, 0.13 mmol), hydrazine sulfate (432 mg, 3.3 mmol), and diisopropylethylamine (1.2 mL, 6.6 mmol) were dissolved in a 9:1 solution of EtOH:H$_2$O (0.017 M). This solution was heated at 78° C. with stirring for 16 h. Upon completion, the mixture was evaporated and purified by column chromatography (DCM/MeOH) to afford the product. Yield: 36 mg, 50%. $^1$H NMR (400 MHz, DMSO-d$_6$) δ 8.71; (s, 2H), 8.64; (d, J=1.5 Hz, 1H), 8.22; (dd, J=22.0, 8.1 Hz, 1H), 8.16-8.12; (m, 1H), 8.12-8.08; (m, 1H), 7.92; (dd, J=8.0, 1.5 Hz, 1H), 7.78; (dd, J=8.0, 1.7 Hz, 1H), 7.72; (dd, J=7.0, 3.2 Hz, 1H), 7.57; (d, J=7.2 Hz, 1H), 3.47; (q, J=6.3 Hz, 1H), 3.38; (q, J=6.4, 5.8 Hz, 1H), 2.07-1.98; (m, 4H), 1.69-1.56; (m, 4H), 1.47-1.31; (m, 2H), 1.27-1.09; (m, 8H), 0.82-0.71; (m, 2H). HRMS (ESI): predicted for [M+H]$^+$ $C_{27}H_{33}N_4O_4S_2$ 541.1943.

2,7-bis((2-azabicyclo[2.2.1]heptan-2-yl)sulfonyl)-9H-fluoren-9-one (TKD1076). 9-oxo-9H-fluorene-2,7-disulfonyl dichloride (100 mg, 0.27 mmol) and 2-azabicyclo[2.2.1.]heptane (67 mg, 0.69 mmol) were coupled according to General Procedure A. Yield: 113 mg, 86%. $^1$H NMR (400 MHz, DMSO) δ 8.22; (d, J=7.9 Hz, 2H), 8.15; (dd, J=7.9, 1.7 Hz, 2H), 7.92; (d, J=1.6 Hz, 2H), 4.22; (s, 2H), 3.08-2.97; (m, 4H), 2.46; (s, 2H), 1.64-1.50; (m, 6H), 1.39-1.29; (m, 2H), 1.19; (d, J=9.9 Hz, 2H), 0.85; (dd, J=10.0, 2.5 Hz, 2H). MS (ESI) predicted m/z 499.1 [M+H]$^+$.

2,7-bis((2-azabicyclo[2.2.1]heptan-2-yl)sulfonyl)-9H-fluoren-9-one oxime (TKD1080). TKD1076 (113 mg, 0.23 mmol), hydroxylamine hydrochloride (393 mg, 5.7 mmol), and sodium hydroxide (228 mg, 5.7 mmol) reacted according to General Procedure B. Yield: 68 mg, 59%. $^1$H NMR (400 MHz, DMSO) δ 13.37; (s, 1H), 8.71 (d, J=1.3 Hz, 1H), 8.32; (d, J=8.0 Hz, 1H), 8.27; (d, J=8.0 Hz, 1H), 8.11-8.03; (m, 2H), 7.98; (dd, J=1.4, 8.0 Hz, 1H), 4.18; (d, J=10.5 Hz, 2H), 3.08-2.98; (m, 4H), 2.45; (s, 2H), 1.65-1.48; (m, 6H), 1.39-1.28; (m, 2H), 1.18; (d, J=9.9 Hz, 2H), 0.80; (d, J=9.6 Hz, 2H). HRMS (ESI): predicted for [M+H]$^+$ $C_{25}H_{28}N_3O_5S_2$ 514.1470.

N$^2$-cyclohexyl-9-oxo-N$^7$-(tetrahydro-2H-pyran-4-yl)-9H-fluorene-2,7-disulfonamide (TKD1048A). 9-oxo-9H-fluorene-2,7-disulfonyl dichloride (100 mg, 0.27 mmol), tetrahydro-2H-pyran-4-amine hydrochloride (95 mg, 0.69 mmol), and cyclohexylamine (79 μL, 0.69 mmol) were combined according to General Procedure A. A mixture of three coupled products was produced, and the title product was separated and purified by column chromatography. Yield: 32 mg, 23%. $^1$H NMR (400 MHz, DMSO) δ 8.18-8.10; (m, 4H), 8.02; (s, 3H), 7.86; (bs, 1H), 3.71; (dt, J=3.6, 12.1 Hz, 2H), 3.28-3.18; (m, 2H), 3.00; (bs, 1H), 1.66-1.50; (m, 6H), 1.40-1.31; (m, 3H), 1.14; (t, J=9.7 Hz, 4H), 1.09-0.99; (m, 1H). MS (ESI) predicted m/z 529.2 [M+H]$^+$.

N$^2$-cyclohexyl-9-(hydroxyimino)-N$^7$-(tetrahydro-2H-pyran-4-yl)-9H-fluorene-2,7-disulfonamide, mixture of E and Z isomers (TKD1051A). TKD1048A (26 mg, 0.05 mmol), hydroxylamine hydrochloride (90 mg, 1.3 mmol), and sodium hydroxide (52 mg, 1.3 mmol) reacted according to General Procedure B. Yield: 24 mg, 89%. $^1$H NMR (400 MHz, DMSO) δ 13.33; (s, 1H), 8.82; (d, J=2.6 Hz, 1H), 8.22; (t, J=9.0 Hz, 1H), 8.17; (d, J=5.2 Hz, 1H), 8.03; (q, J=6.7 Hz, 2H), 7.96; (t, 7.0 Hz, 1H), 7.84; (dd, J=7.3, 19.2 Hz, 1H), 3.71; (dt, J=3.5, 11.9 Hz, 2H), 3.23; (t, J=10.7 Hz, 3H), 2.99; (s, 1H), 1.64-1.50; (m, 6H), 1.48-1.31; (m, 3H), 1.13; (t, J=9.1 Hz, 4H), 1.07-0.97; (m, 1H). HRMS (ESI): predicted for [M+H]$^+$ $C_{24}H_{30}N_3O_6S_2$ 520.1576.

N2-((1R,2R,4S)-bicyclo[2.2.1]heptan-2-yl)-N7-((2S)-bicyclo[2.2.1]heptan-2-yl)-9-oxo-9H-fluorene-2,7-disulfonamide (TKD2032). 9-oxo-9H-fluorene-2,7-disulfonyl dichloride (100 mg, 0.27 mmol) and exo-2-aminobornane (77 mg, 0.69 mmol) were coupled according to General Procedure A. Yield: 140 mg, 87%. $^1$H NMR (400 MHz, DMSO) δ 8.16; (d, J=7.8 Hz, 2H), 8.11; (dd, J=1.7, 7.8 Hz, 2H), 7.99; (d, J=1.2 Hz, 2H), 7.75; (d, J=7.1 Hz, 2H), 3.03; (dt, J=3.5, 7.4 Hz, 2H), 2.12; (t, J=3.3 Hz, 2H), 1.99; (d, J=3.2 Hz, 2H), 1.49-1.41; (m, 3H), 1.37-1.30; (m, 3H), 1.27; (t, J=6.9 Hz, 3H), 1.25-1.18; (m, 2H), 1.04-0.93; (m, 5H). MS (ESI) predicted m/z 527.2 [M+H]$^+$.

(E)-N2-((1R,2R,4S)-bicyclo[2.2.1]heptan-2-yl)-N7-((2S)-bicyclo[2.2.1]heptan-2-yl)-9-(hydroxyimino)-9H-fluorene-2,7-disulfonamide (TKD2036). TKD1032 (122 mg, 0.23 mmol), hydroxylamine hydrochloride (395 mg, 5.7 mmol), and sodium hydroxide (225 mg, 5.7 mmol) reacted according to General Procedure B. Yield: 82 mg, 66%. $^1$H NMR (400 MHz, DMSO) δ 13.31; (s, 1H), 8.80; (d, J=1.4 Hz, 1H), 8.24; (d, J=8.0 Hz, 1H), 8.19; (d, J=8.0 Hz, 1H), 8.14; (d, J=1.3 Hz, 1H), 8.01; (dd, J=1.7, 8.0 Hz, 1H), 7.93; (dd, J=1.7, 8.0 Hz, 1H), 7.75; (d, J=7.2 Hz, 1H), 7.70; (d, J=7.1 Hz, 1H), 3.08-2.99; (m, 2H), 2.10; (s, 2H; partially obscured by acetone peak), 1.97; (s, 2H), 1.43; (t, J=10.5 Hz, 4H), 1.38-1.28; (m, 4H), 1.27 1.18; (m, 3H), 0.98; (t, J=9.6 Hz, 5H). HRMS (ESI): predicted for [M+H]$^+$ $C_{27}H_{32}N_3O_5S_2$ 542.1783.

N$^2$,N$^7$-di(adamantan-2-yl)-9-oxo-9H-fluorene-2,7-disulfonamide (TKD2033). 9-oxo-9H-fluorene-2,7-disulfonyl dichloride (100 mg, 0.27 mmol) and 2-adamantylamine (129 mg, 0.69 mmol) were coupled according to General Procedure A. Yield: 161 mg, 50%. $^1$H NMR (400 MHz, DMSO) δ 8.13; (d, J=1.2 Hz, 2H), 8.10-8.04; (m, 3H), 7.94-7.84; (m, 2H), 7.76; (d, J=6.5 Hz, 1H), 3.24; (bs, 2H), 1.99; (t, J=12.6 Hz, 4H), 1.69; (d, J=11.7 Hz, 12H), 1.64-1.53; (m, 8H), 1.40; (d, J=12.3 Hz, 4H). MS (ESI) predicted m/z 607.2 [M+H]$^+$.

N$^2$,N$^7$-di(adamantan-2-yl)-9-(hydroxyimino)-9H-fluorene-2,7-disulfonamide (TKD2043). TKD2033 (80 mg, 0.13 mmol), hydroxylamine hydrochloride (224 mg, 3.2 mmol), and sodium hydroxide (129 mg, 3.2 mmol) reacted according to General Procedure B. Yield: 29 mg, 35%. $^1$H NMR (400 MHz, DMSO) δ 13.26; (s, 1H), 8.83; (d, J=1.4 Hz, 1H), 8.23-8.18; (m, 2H), 8.16; (d, J=8.0 Hz, 1H), 8.04; (dd, J=1.7, 8.0 Hz, 1H), 7.96; (dd, J=1.7, 8.0 Hz, 1H), 7.89; (d, J=6.6 Hz, 1H), 7.83; (d, J=6.5 Hz, 1H), 3,26; (t, J=6.3 Hz, 2H), 1.99; (d, J=12.2 Hz, 4H), 1.74-1.65; (m, 12H), 1.63-1.53; (m, 8H), 1.39; (d, J=12.6 Hz, 4H). HRMS (ESI): predicted for [M+H]$^+$ $C_{33}H_{40}N_3O_5S_2$ 622.2409.

Diethyl 1,1'-((9-oxo-9H-fluorene-2,7-disulfonyl)bis(azanediyl))bis(cyclohexane-1-carboxylate) (TKD2038). 9-oxo-9H-fluorene-2,7-disulfonyl dichloride (100 mg, 0.27 mmol) and ethyl 1-aminocyclohexane-1-carboxylate hydrochloride (143 mg, 0.69 mmol) were coupled according to General Procedure A. Yield: 51 mg, 30%. $^1$H NMR (400 MHz, DMSO) δ 8.24; (s, 2H), 8.13; (d, J=7.9 Hz, 2H), 8.04; (dd, J=1.7, 7.9 Hz, 2H), 7.97; (d, J=1.3 Hz, 2H), 3.82; (q, J=7.1 Hz, 4H), 1.85-1.71; (m, 8H), 1.41-1.28; (m, 10H), 1.24-1.19; (m, 2H), 1.06; (t, J=7.1 Hz, 6H). MS (ESI) predicted m/z 647.2 [M+H]$^+$.

Diethyl 1,1'-((9-(hydroxyimino)-9H-fluorene-2,7-disulfonyl)bis(azanediyl))bis(cyclohexane-1-carboxylate) (TKD2044). TKD2038 (51 mg, 0.08 mmol), hydroxylamine hydrochloride (137 mg, 2.0 mmol), and sodium hydroxide (79 mg, 2.0 mmol) reacted according to General Procedure B. Yield: 20 mg, 38%. $^1$H NMR (400 MHz, DMSO) δ 13.26; (s, 1H), 8.78; (d, J=1.5 Hz, 1H), 8.20; (d, J=8.0 Hz, 2H), 8.16; (d, J=8.0 Hz, 2H), 8.11; (d, J=1.4 Hz, 1H), 7.95; (dd, J=1.7, 8.0 Hz, 1H), 7.87; (dd, J=1.7, 8.0 Hz, 1H), 3.78; (dq, J=2.6, 7.1 Hz, 4H), 1.87-1.68; (m, 8H), 1.43-1.25; (m, 10H), 1.22-1.15; (m, 2H), 1.04; (t, J=7.1 Hz, 6H). HRMS (ESI): predicted for [M+H]$^+$ $C_{31}H_{39}N_3O_9S_2$ 661.2128.

7-(N-(bicyclo[2.2.1]heptan-2-yl)sulfamoyl)-9H-fluorene-2-sulfonyl chloride (TKD2061). 9H-fluorene-2,7-disulfonyl dichloride (100 mg, 0.28 mmol) and 2-norbornylamine hydrochloride (41 mg, 0.28 mmol) were coupled according to General Procedure C. Yield: 54 mg, 45%. $^1$H NMR (400 MHz, DMSO-d$_6$) δ 8.08; (d, J=8.1 Hz, 1H), 7.99; (d, J=1.6 Hz, 1H), 7.94; (d, J=7.9 Hz, 1H), 7.85; (d, J=1.4 Hz, 1H), 7.82; (dd, J=8.0, 1.7 Hz, 1H), 7.69; (dd, J=7.9, 1.5 Hz, 1H), 7.66; (d, J=7.2 Hz, 1H), 4.05; (s, 2H), 3.38; (dd, J=11.2, 5.1

Hz, 1H), 2.06-1.97; (m, 2H), 1.70-1.58; (m, 2H), 1.37; (dtd, J=9.7, 6.8, 5.5, 2.7 Hz, 1H), 1.27-1.09; (m, 4H), 0.78; (ddd, J=12.7, 4.7, 3.0 Hz, 1H). MS (ESI) predicted m/z 438.1 [M+H]+.

$N^2$-(bicyclo [2.2.1] heptan-2-yl)-$N^7$-(tetrahydro-2H-pyran-4-yl)-9H-fluorene-2,7-disulfonamide (TKD2063). TKD2061 (9.4 mg, 0.02 mmol), and tetrahydro-2H-pyran-4-amine hydrochloride (5.9 mg, 0.04 mmol) were coupled according to General Procedure D. Yield: 9 mg, 88%. $^1$H NMR (400 MHz, DMSO-$d_6$) δ 8.20; (dd, J=8.1, 2.8 Hz, 2H), 8.06; (dd, J=10.8, 1.6 Hz, 2H), 7.89; (ddd, J=11.8, 8.1, 1.7 Hz, 2H), 7.84; (d, J=7.2 Hz, 1H), 7.72; (d, J=7.0 Hz, 1H), 4.17; (s, 2H), 3.70; (dt, J=11.7, 3.6 Hz, 2H), 3.44-3.35; (m, 1H), 3.27-3.16; (m, 3H), 2.02; (dt, J=9.2, 4.2 Hz, 2H), 1.69-1.58; (m, 2H), 1.57-1.48; (m, 2H), 1.42-1.29; (m, 3H), 1.27-1.09; (m, 4H), 0.77; (ddd, J=12.7, 4.7, 2.9 Hz, 1H). MS (ESI) predicted m/z 503.2 [M+H]+.

7-(N-(bicyclo[2.2.1]heptan-2-yl)sulfamoyl)-9-oxo-9H-fluorene-2-sulfonyl chloride (TKD2064). 9-oxo-9H-fluorene-2,7-disulfonyl dichloride (100 mg, 0.27 mmol) and 2-norbornylamine hydrochloride (39 mg, 0.27 mmol) reacted according to General Procedure C. Yield: 45 mg, 37%. $^1$H NMR (400 MHz, DMSO-$d_6$) δ 8.05-7.97; (m, 2H), 7.93; (t, J=1.2 Hz, 1H), 7.89; (d, J=1.2 Hz, 2H), 7.84-7.77; (m, 2H), 3.45-3.36; (m, 1H), 2.07-2.00; (m, 2H), 1.72-1.55; (m, 2H), 1.38; (qt, J=12.0, 5.9 Hz, 1H), 1.28-1.11; (m, 4H), 0.77; (ddd, J=12.6, 4.7, 3.0 Hz, 1H). MS (ESI) predicted m/z 452.0 [M+H]+.

$N^2$-(bicyclo[2.2.1]heptan-2-yl)-9-oxo-$N^7$-(tetrahydro-2H-pyran-4-yl)-9H-fluorene-2,7-disulfonamide (TKD2067). TKD2064 (10 mg, 0.02 mmol) and tetrahydro-2H-pyran-4-amine hydrochloride (8 mg, 0.06 mmol) were coupled according to General Procedure D. Yield: 10 mg, 89%. $^1$H NMR (400 MHz, DMSO-$d_6$) δ 8.17-8.12; (m, 3H), 8.09; (dd, J=7.9, 1.7 Hz, 1H), 8.04-7.97; (m, 3H), 7.91-7.81; (m, 1H), 3.70; (dt, J=11.7, 3.6 Hz, 2H), 3.41; (d, J=10.9 Hz, 1H), 3.29-3.17; (m, 3H), 2.03; (dt, J=12.7, 4.3 Hz, 2H), 1.66; (dddd, J=12.8, 11.5, 4.9, 3.1 Hz, 1H), 1.61-1.50; (m, 2H), 1.36; (dtd, J=12.9, 10.7, 4.5 Hz, 3H), 1.27-1.20; (m, 2H), 1.20-1.11; (m, 3H), 0.76; (ddd, J=12.6, 4.7, 3.0 Hz, 1H). MS (ESI) predicted m/z 517.1 [M+H]+.

$N^2$-(bicyclo [2.2.1] heptan-2-yl)-9-(hydroxyimino)-$N^7$-(tetrahydro-2H-pyran-4-yl)-9H-fluorene-2,7-disulfonamide (TKD2088). TKD2067 (48 mg, 0.09 mmol), hydroxylamine hydrochloride (161 mg, 2.3 mmol), and sodium hydroxide (93 mg, 2.3 mmol) reacted according to General Procedure B. Yield: 30 mg, 61%. $^1$H NMR (400 MHz, DMSO-$d_6$) δ 13.28; (d, J=3.8 Hz, 1H), 8.80; (dd, J=4.6, 1.8 Hz, 1H), 8.22 (dd, J=8.0, 3.5 Hz, 1H), 8.18; (dd, J=8.0, 2.9 Hz, 1H), 8.14; (dd, J=6.4, 1.7 Hz, 1H), 7.98; (dddd, J=32.0, 12.0, 8.0, 1.7 Hz, 3H), 7.85; (dd, J=20.9, 7.1 Hz, 1H), 3.70; (dt, J=11.6, 3.7 Hz, 2H), 3.46-3.37; (m, 1H), 3.22; (td, J=11.6, 2.4 Hz, 3H), 2.02; (d, J=5.1 Hz, 2H), 1.71-1.57; (m, 2H), 1.53; (d, J=12.6 Hz, 2H), 1.36; (qd, J=12.4, 11.7, 4.3 Hz, 3H), 1.24; (d, J=6.1 Hz, 2H), 1.15; (q, J=10.1, 9.6 Hz, 3H), 0.77; (d, J=12.8 Hz, 1H). HRMS (ESI): predicted for [M+H]+ $C_{25}H_{30}N_3O_6S_2$ 532.1576.

Methyl (1r,4r)-4-((7-(N-(bicyclo[2.2.1]heptan-2-yl)sulfamoyl)-9-oxo-9H-fluorene)-2-sulfonamido)cyclohexane-1-carboxylate (TKD2068). TKD2064 (10 mg, 0.02 mmol) and methyl (1r,4r)-4-aminocyclohexane-1-carboxylate hydrochloride (11 mg, 0.057 mmol) were coupled according to General Procedure D. Yield: 8 mg, 63%. $^1$H NMR (400 MHz, DMSO-$d_6$) δ 8.15-8.11; (m, 2H), 8.09; (d, J=7.9 Hz, 1H), 8.01-7.97; (m, 2H), 7.88; (s, 2H), 3.53; (s, 3H), 3.42; (dtd, J=10.8, 4.5, 1.5 Hz, 1H), 2.98; (tt, J=10.8, 4.0 Hz, 1H), 2.17; (tt, J=11.7, 3.6 Hz, 1H), 2.04; (dt, J=12.1, 4.3 Hz, 2H), 1.85-1.75; (m, 2H), 1.72-1.53; (m, 3H), 1.46-1.34; (m, 1H), 1.34-1.10; (m, 9H), 0.76; (ddd, J=12.7, 4.7, 3.0 Hz, 1H). MS (ESI) predicted m/z 573.2 [M+H]+.

Methyl (1r,4r)-4-((7-(N-(bicyclo[2.2.1]heptan-2-yl)sulfamoyl)-9-(hydroxyimino)-9H-fluorene)-2-sulfonamido)cyclohexane-1-carboxylate (TKD2089). TKD2068 (55 mg, 0.10 mmol), hydroxylamine hydrochloride (167 mg, 2.4 mmol), and sodium hydroxide (96 mg, 2.4 mmol) reacted according to General Procedure B. Yield: 43 mg, 77%. $^1$H NMR (400 MHz, DMSO-$d_6$) δ 13.27; (s, 1H), 8.80; (t, J=1.3 Hz, 1H), 8.22; (d, J=8.0 Hz, 1H), 8.19; (s, 1H), 8.14; (t, J=1.6 Hz, 1H), 8.01; (td, J=8.4, 1.8 Hz, 1H), 7.93; (td, J=7.8, 1.7 Hz, 1H), 7.88; (t, J=7.6 Hz, 1H), 7.83; (dd, J=10.0, 7.2 Hz, 1H), 3.53; (s, 3H), 3.42; (dd, J=9.3, 5.3 Hz, 1H), 3.04-2.91; (m, 1H), 2.22-2.12; (m, 1H), 2.02; (q, J=5.1, 4.5 Hz, 2H), 1.79; (t, J=7.3 Hz, 3H), 1.71-1.56; (m, 4H), 1.44-1.32; (m, 1H), 1.32-1.21 (m, 3H), 1.21-1.09; (m, 4H), 0.78; (dp, J=12.7, 2.3 Hz, 1H). HRMS (ESI): predicted for [M+H]+ $C_{28}H_{34}N_3O_7S_2$ 588.1838.

(1r,4r)-4-((7-(N-(bicyclo[2.2.1]heptan-2-yl)sulfamoyl)-9-(hydroxyimino)-9H-fluorene)-2-sulfonamido)cyclohexane-1-carboxylic acid (TKD2092). TKD2089 (22 mg, 0.04 mmol) was saponified according to General Procedure E. Yield: 16 mg, 76%. $^1$H NMR (400 MHz, DMSO-$d_6$) δ 13.28; (s, 1H), 12.05; (s, 1H), 8.80; (d, J=1.7 Hz, 1H), 8.22; (d, J=8.0 Hz, 1H), 8.17; (d, J=8.0 Hz, 1H), 8.14; (d, J=1.8 Hz, 1H), 8.01; (td, J=8.3, 1.7 Hz, 1H), 7.93; (td, J=7.9, 1.7 Hz, 1H), 7.88; (t, J=5.1 Hz, 1H), 7.83; (t, J=6.4 Hz, 1H), 3.40; (d, J=11.6 Hz, 1H), 2.96; (s, 1H), 2.02; (d, J=5.6 Hz, 4H), 1.79; (d, J=11.6 Hz, 2H), 1.72-1.56; (m, 4H), 1.38; (s, 1H), 1.19; (ddd, J=25.5, 14.4, 8.4 Hz, 7H), 0.82-0.73; (m, 1H). HRMS (ESI): predicted for [M+H]+ $C_{27}H_{32}N_3O_7S_2$ 574.1682.

Ethyl 3-(7-(N-(bicyclo[2.2.1]heptan-2-yl)sulfamoyl)-9-oxo-9H-fluorene)-2-sulfonamido)-2,2-dimethylpropanoate (TKD2084). TKD2064 (56 mg, 0.12 mmol) and ethyl 3-amino-2,2-dimethylpropanoate hydrochloride (34 mg, 0.19 mmol) were coupled according to General Procedure D. Yield 62 mg, 90%. $^1$H NMR (400 MHz, DMSO-$d_6$) δ 8.15; (ddd, J=7.9, 3.6, 0.7 Hz, 2H), 8.10; (dt, J=7.8, 1.4 Hz, 2H), 8.01; (ddd, J=6.4, 1.7, 0.6 Hz, 2H), 7.87; (d, J=5.6 Hz, 2H), 4.02; (q, J=7.1 Hz, 2H), 3.43; (s, 1H), 2.88; (s, 2H), 2.04; (d, J=9.8, 4.7 Hz, 2H), 1.67; (tdd, J=12.4, 4.7, 3.0 Hz, 1H), 1.63-1.54; (m, 1H), 1.39; (td, J=11.6, 9.4, 4.4 Hz, 1H), 1.25; (d, J=10.1 Hz, 1H), 1.16; (t, J=7.1 Hz, 5H), 1.08; (s, 6H), 1.04; (d, J=6.1 Hz, 1H), 0.76; (ddd, J=12.6, 4.7, 2.9 Hz, 1H). MS (ESI) predicted m/z 561.1 [M+H]+.

Ethyl 3-((7-(N-(bicyclo[2.2.1]heptan-2-yl)sulfamoyl)-9-(hydroxyimino)-9H-fluorene)-2-sulfonamido)-2,2-dimethylpropanoate (TKD2090). TKD2084 (62 mg, 0.11 mmol), hydroxylamine hydrochloride (192 mg, 2.8 mmol), and sodium hydroxide (111 mg, 2.8 mmol) reacted according to General Procedure B. Yield: 43 mg, 67%. $^1$H NMR (400 MHz, DMSO-$d_6$) δ 13.28; (s, 1H), 8.79; (dd, J=7.4, 1.7 Hz, 1H), 8.23; (dd, J=8.0, 5.4 Hz, 1H), 8.19; (dd, J=8.0, 4.3 Hz, 1H), 8.14; (s, 1H), 8.01; (d, J=8.0 Hz, 1H), 7.93; (dd, J=7.9, 1.9 Hz, 1H), 7.87; (d, J=7.0 Hz, 1H), 7.82; (d, J=7.0 Hz, 1H), 4.01; (qd, J=7.1, 2.9 Hz, 2H), 3.48-3.38; (m, 1H), 2.88; (d, J=5.7 Hz, 2H), 2.02; (q, J=4.8 Hz, 2H), 1.75; (d, J=13.6 Hz, 1H), 1.64; (dq, J=18.3, 10.4, 9.5 Hz, 2H), 1.37; (s, 1H), 1.24; (d, J=8.8 Hz, 1H), 1.14; (td, J=7.1, 2.0 Hz, 5H), 1.08; (d, J=2.1 Hz, 6H), 0.78; (d, J=13.0 Hz, 1H). HRMS (ESI): predicted for [M+H]+ $C_{27}H_{34}N_3O_7S_2$ 576.1838.

3-((7-(N-(bicyclo[2.2.1]heptan-2-yl)sulfamoyl)-9-(hydroxyimino)-9H-fluorene)-2-sulfonamido)-2,2-dimethylpropanoic acid (TKD2093). TKD2090 (27 mg, 0.05 mmol)

was saponified according to General Procedure E. Yield: 14 mg, 54%. HRMS (ESI): predicted for [M+H]$^+$ C$_{25}$H$_{30}$N$_3$O$_7$S$_2$ 548.1525.

N$^2$-(bicyclo[2.2.1]heptan-2-yl)-N$^7$-((1r,3r)-3-hydroxycyclobutyl)-9-oxo-9H-fluorene-2,7-disulfonamide (TKD20-98A). TKD2064 (57 mg, 0.13 mmol) and (1r,3r)-3-aminocyclobutan-1-ol hydrochloride (31 mg, 0.25 mmol) were coupled according to General Procedure D. Yield: 12 mg, 19%. $^1$H NMR (400 MHz, DMSO-d$_6$) δ 8.17-8.12; (m, 2H), 8.11; (d, J=1.6 Hz, 1H), 8.10-8.04; (m, 2H), 8.00; (dd, J=1.7, 0.7 Hz, 1H), 7.95; (dd, J=1.8, 0.6 Hz, 1H), 7.87; (d, J=7.0 Hz, 1H), 4.94; (d, J=5.1 Hz, 1H), 4.13; (q, J=5.6, 4.2 Hz, 1H), 3.78 (h, J=6.9 Hz, 1H), 3.42; (dd, J=11.3, 6.0 Hz, 1H), 2.09-1.85; (m, 4H), 1.73-1.54; (m, 2H), 1.48-1.33; (m, 1H), 1.30-1.21; (m, 4H), 1.17; (td, J=10.5, 9.6, 6.8 Hz, 2H), 0.77; (dt, J=12.6, 3.9 Hz, 1H). MS (ESI) predicted m/z 503.1 [M+H]$^+$.

(Z)-N$^2$-(bicyclo[2.2.1]heptan-2-yl)-N$^7$-((1r,3r)-3-hydroxycyclobutyl)-9-(hydroxyimino)-9H-fluorene-2,7-disulfonamide (TKD3003). TKD2098A (10 mg, 0.02 mmol), hydroxylamine hydrochloride (35 mg, 0.5 mmol), and sodium hydroxide (12 mg, 0.5 mmol) reacted according to General Procedure B. Yield: 7 mg, 70%. $^1$H NMR (400 MHz, DMSO-d$_6$) δ 13.25; (s, 1H), 8.78; (dd, J=17.6, 1.8 Hz, 1H), 8.26-8.20 (m, 1H), 8.18; (dd, J=8.0, 2.8 Hz, 1H), 8.12; (dd, J=18.8, 1.7 Hz, 1H), 8.01; (dd, J=8.0, 1.8 Hz, 1H), 7.94; (ddd, J=15.6, 8.0, 1.8 Hz, 1H), 7.91-7.80; (m, 2H), 4.92; (d, J=5.0 Hz, 1H), 4.11; (t, J=5.8 Hz, 1H), 3.78; (d, J=7.9 Hz, 1H), 3.41; (d, J=5.2 Hz, 1H), 2.06-1.84; (m, 5H), 1.71-1.56; (m, 2H), 1.38; (s, 1H), 1.24; (d, J=6.6 Hz, 2H), 1.21-1.10; (m, 3H), 0.78; (d, J=13.3 Hz, 1H). HRMS (ESI): predicted for [M+H]$^+$ C$_{24}$H$_{28}$N$_3$O$_6$S$_2$ 518.1420.

N$^2$-(bicyclo[2.2.1]heptan-2-yl)-N$^7$-((1r,4r)-4-hydroxycyclohexyl)-9-oxo-9H-fluorene-2,7-disulfonamide (TKD30-07). TKD2064 (58 mg, 0.13 mmol) and (1r,4r)-4-aminocyclohexan-1-ol (22 mg, 0.19 mmol) were coupled according to General Procedure D. Yield: 41 mg, 60%. $^1$H NMR (400 MHz, DMSO-d$_6$) δ 8.16-8.08; (m, 4H), 7.99; (td, J=1.6, 0.7 Hz, 2H), 7.85; (dd, J=13.8, 7.0 Hz, 2H), 4.48; (d, J=4.3 Hz, 1H), 3.47-3.37; (m, 1H), 3.27; (dt, J=10.0, 5.1 Hz, 1H), 2.94; (d, J=8.8 Hz, 1H), 2.04; (d, J=12.1 Hz, 2H), 1.69; (dd, J=8.9, 4.0 Hz, 3H), 1.65-1.55; (m, 3H), 1.40; (ddd, J=12.6, 9.0, 4.1 Hz, 1H), 1.27-1.00; (m, 8H), 0.81-0.72; (m, 1H). MS (ESI) predicted m/z 531.7 [M+H]$^+$.

(Z)-N$^2$-(bicyclo[2.2.1]heptan-2-yl)-N$^7$-((1r,4r)-4-hydroxycyclohexyl)-9-(hydroxyimino)-9H-fluorene-2,7-disulfonamide (TKD3014). TKD3007 (38 mg, 0.07 mmol), hydroxylamine hydrochloride (124 mg, 1.8 mmol), and sodium hydroxide (72 mg, 1.8 mmol) reacted according to General Procedure B. Yield: 33 mg, 85%. $^1$H NMR (400 MHz, DMSO-d$_6$) δ 12.72; (s, 1H), 8.79; (dd, J=3.1, 1.7 Hz, 1H), 8.21; (dd, J=8.0, 1.4 Hz, 1H), 8.17; (d, J=8.0 Hz, 1H), 8.14; (d, J=1.6 Hz, 1H), 8.01; (ddd, J=8.0, 5.0, 1.8 Hz, 1H), 7.93; (ddd, J=8.0, 4.3, 1.7 Hz, 1H), 7.85; (d, J=22.7 Hz, 2H), 4.47; (d, J=4.2 Hz, 1H), 3.40; (s, 1H), 3.24; (s, 1H), 2.99-2.89; (m, 1H), 2.02; (dt, J=9.2, 4.3 Hz, 1H), 1.69; (dd, J=11.9, 5.3 Hz, 3H), 1.64; (s, 3H), 1.48-1.27; (m, 1H), 1.26-0.93; (m, 8H), 0.78; (ddt, J=12.7, 4.8, 2.3 Hz, 1H). HRMS (ESI): predicted for [M+H]$^+$ C$_{26}$H$_{32}$N$_3$O$_6$S$_2$ 546.1733.

Tert-butyl 4-((7-(N-(bicyclo[2.2.1]heptan-2-yl)sulfamoyl)-9-oxo-9H-fluorene)-2-sulfonamido)piperidine-1-carboxylate (TKD3017). TKD2064 (58 mg, 0.13 mmol) and tent-butyl 4-aminopiperidine-1-carboxylate (51 mg, 0.26 mmol) were coupled according to General Procedure D. Yield: 53 mg, 67%. $^1$H NMR (400 MHz, DMSO-d$_6$) δ 8.18-8.07; (m, 4H), 8.00; (ddd, J=3.8, 1.7, 0.7 Hz, 2H), 7.76; (s, 2H), 3.70; (d, J=13.3 Hz, 2H), 3.47-3.38; (m, 1H), 3.23; (dq, J=9.9, 5.1, 4.2 Hz, 1H), 2.76; (s, 2H), 2.09-2.00; (m, 2H), 1.73-1.61; (m, 1H), 1.62-1.51; (m, 3H), 1.45-1.37; (m, 1H), 1.35; (s, 8H; Boc hydrogens, 1 missing), 1.24; (d, J=10.6 Hz, 2H), 1.20-1.12; (m, 4H), 0.76 ;(ddd, J=12.6, 4.7, 3.0 Hz, 1H). MS (ESI) predicted m/z 616.2 [M+H]$^+$.

Tert-butyl (Z)-4-((7-(N-(bicyclo[2.2.1]heptan-2-yl)sulfamoyl)-9-(hydroxyimino)-9H-fluorene)-2-sulfonamido)piperidine-1-carboxylate (TKD3021). TKD3017 (50 mg, 0.08 mmol), hydroxylamine hydrochloride (141 mg, 2.0 mmol), and sodium hydroxide (81 mg, 2.0 mmol) reacted according to General Procedure B. Yield: 42 mg, 82%. $^1$H NMR (400 MHz, DMSO-d$_6$) δ 13.29; (d, J=4.3 Hz, 1H), 8.80; (d, J=1.8 Hz, 1H), 8.22; (dd, J=8.0, 2.8 Hz, 1H), 8.18; (dd, J=8.1, 2.4 Hz, 1H), 8.14; (dd, J=2.7, 1.8 Hz, 1H), 8.06-7.91; (m, 3H), 7.85; (dd, J=20.9, 7.1 Hz, 1H), 3.70; (d, J=13.1 Hz, 2H), 3.41; (s, 1H, partially obscured by water peak), 3.21; (ddt, J=13.7, 9.8, 4.9 Hz, 1H), 2.76; (s, 2H), 2.02; (d, J=5.3 Hz, 2H), 1.60; (dd, J=34.0, 13.0 Hz, 4H), 1.34; (s, 10H), 1.28-1.10; (m, 6H), 0.77; (d, J=12.5 Hz, 1H). MS (ESI) predicted m/z 631.8 [M+H]$^+$.

EK-006: 9-(hydroxyimino)-N2, N7-dioctadecyl-9H-fluorene-2,7-disulfonamide: 9-oxo-9H-fluorene-2,7-disulfonyl dichloride (68 mg, 0.180 mmol) and octadecan-1 -amine (126 mg, 0.469 mmol) were coupled according to general procedure A to synthesize EK-006A, followed by hydroxylamine hydrochloride (313 mg, 4.507 mmol), and sodium hydroxide (180 mg, 4.507 mmol) reacted according to General Procedure B. Yield: 30 mg, 19%. $^1$H NMR (400 MHz, DMSO-d$_6$) δ 13.27; (s, 1H), 8.78; (d, J=1.8 Hz, 1H), 8.24; (d, J=8.0 Hz, 1H), 8.19; (d, J=8.1 Hz, 1H), 8.12; (d, J=1.7 Hz, 1H), 7.99; (dd, J=8.0, 1.7 Hz, 1H), 7.91; (dd, J=8.0, 1.7 Hz, 1H), 7.74; (dt, J=16.0, 5.7 Hz, 2H), 2.78; (q, J=6.6 Hz, 4H), 1.30; (d, J=15.1 Hz, 5H), 1.23; (s, 33H), 1.11; (d, J=26.3 Hz, 26H), 0.88-0.82; (m, 6H). Calculated MS (Maldi, m/z) [M$^-$H]$^{-H}$=886.592.

RB-054B: N$^2$,N$^7$-bis(2,6-difluorophenyl)-9-(hydroxyimino)-9H-fluorene-2,7-disulfonamide: 9-oxo-9H-fluorene-2,7-disulfonyl dichloride (64 mg, 0.169 mmol) and 2,6-difluoroaniline (43 μL, 0.42 mmol) and pyridine (95 μL, 1.18 mmol) were coupled according to general procedure A to synthesize RB-054A, followed by hydroxylamine hydrochloride (37 mg, 0.533 mmol), and sodium hydroxide (21 mg, 0.533 mmol) reacted according to General Procedure B. Yield: 8 mg, 8%. $^1$H NMR (400 MHz, DMSO-d$_6$) δ 13.30; (s, 1H), 10.21; (s, 2H), 8.75; (s, 1H), 8.20; (dd, J=15.6, 8.2 Hz, 2H), 8.06; (s, 1H), 7.86; (dd, J=22.4, 8.0 Hz, 2H), 7.38; (s, 2H), 7.13; (s, 4H). Calculated MS (Maldi, m/z) [M$^-$H]$^-$$_H$=576.032.

RB-055B: 9-(hydroxyimino)-N$^2$,N$^7$-bis(4-(4-methylpiperazin-1-yl)phenyl)-9H-fluorene-2,7-disulfonamide: 9-oxo-9H-fluorene-2,7-disulfonyl dichloride (69 mg, 0.183 mmol) and 4-(4-methylpiperazin-1-yl)aniline (87 mg, 0.457 mmol), pyridine (103 μL, 1.28 mmol) were coupled according to general procedure A to synthesize RB-055A, followed by hydroxylamine hydrochloride (151 mg, 2.18 mmol), and sodium hydroxide (87 mg, 2.18 mmol) reacted according to General Procedure B. Yield: 28 mg, 46%. $^1$H NMR (400 MHz, DMSO-d$_6$) δ 13.40; (s, 1H), 8.71; (d, J=1.7 Hz, 1H), 8.10; (dd, J=16.3, 8.0 Hz, 2H), 8.03 (d, J=1.6 Hz, 1H), 7.82; (dd, J=8.0, 1.7 Hz, 1H), 7.75; (dd, J=8.1, 1.7 Hz, 1H), 6.93; (dd, J=9.1, 3.2 Hz, 4H), 6.85-6.77; (m, 4H), 3.14; (s, 9H), 2.79-2.59; (m, 6H), 2.39; (s, 6H). Calculated MS (Maldi, m/z) [M$^-$H] $^{-H}$=700.238.

RB-062B: N$^2$,N$^7$-bis((2,3-dihydrobenzo[b][1,4]dioxin-2-yl)methyl)-9-(hydroxyimino)-9H-fluorene-2,7-disulfonamide: 9-oxo-9H-fluorene-2,7-disulfonyl dichloride (69 mg, 0.175 mmol) and 2-Aminomethyl-1,4-benzodioxane (75 mg, 0.454 mmol) were coupled according to general procedure A to synthesize RB-62A, followed by hydroxylamine hydrochloride (304 mg, 4.375 mmol), and sodium hydroxide (174 mg, 4.375 mmol) reacted according to General Procedure B. Yield: 64 mg, 56%. $^1$H NMR (400 MHz, DMSO-d$_6$) δ 13.32; (s, 1H), 8.81; (s, 1H), 8.28-8.13; (m, 5H), 8.04; (dd, J=8.1, 1.8 Hz, 1H), 7.96; (dd, J=8.0, 1.7 Hz, 1H), 6.85-6.80; (m, 2H), 6.75; (dtd, J=10.6, 4.9, 2.4 Hz, 6H), 4.26; (dt, J=11.5, 2.2 Hz, 2H), 4.18; (t, J=6.0 Hz, 2H), 3.94; (ddd, J=11.4, 7.0, 2.5 Hz, 2H), 3.20-3.07; (m, 4H). Calculated MS (Maldi, m/z) [M$^-$H]$^{-H}$=648.112.

RB-66B: (Z)-N$^2$-(2-(5-chloro-1H-indol-1-yl)ethyl)-N$^7$-(2-(5-chloro-1H-indol-2-yl)ethyl)-9-(hydroxyimino)-9H-fluorene-2,7-disulfonamide: 9-oxo-9H-fluorene-2,7-disulfonyl dichloride (66 mg, 0.175 mmol) and 2-(5-chloro-1H-indol-1-yl)ethan-1-amine hydrochloride (104 mg, 0.454 mmol) were coupled according to general procedure A to synthesize RB-66A, followed by hydroxylamine hydrochloride (304 mg, 4.375 mmol), and sodium hydroxide (174 mg, 4.375 mmol) reacted according to General Procedure B. Yield: 80 mg, 64%. $^1$H NMR (400 MHz, DMSO-d$_6$) δ 13.22; (s, 1H), 10.99; (s, 2H), 8.78-8.73; (m, 1H), 8.17-8.06; (m, 3H), 7.94; (dd, J=8.0, 1.8 Hz, 1H), 7.92-7.82; (m, 3H), 7.37-7.33; (m, 2H), 7.25; (dd, J=8.6, 4.9 Hz, 2H), 7.20; (t, J=2.0 Hz, 2H), 6.94; (ddd, J=8.6, 4.0, 2.1 Hz, 2H), 3.05; (d, J=6.6 Hz, 4H), 2.78; (td, J=7.4, 2.4 Hz, 4H). Calculated MS (Maldi, m/z) [M$^-$H]$^{-H}$=706.076.

RB-134B: 9-(hydroxyimino)-N$^2$,N$^7$-bis(4-(trifluoromethyl)cyclohexyl)-9H-fluorene-2,7-disulfonamide: 9-oxo-9H-fluorene-2,7-disulfonyl dichloride (50 mg, 0.132 mmol) and 4-(trifluoromethyl)cyclohexan-1-amine (51 μL, 0.345 mmol) were coupled according to general procedure A to synthesize RB-134A, followed by hydroxylamine hydrochloride (183 mg, 2.64 mmol), and sodium hydroxide (105.6 mg, 2.64 mmol) reacted according to General Procedure B. Yield: 24 mg, 28%. $^1$H NMR (400 MHz, DMSO-d$_6$) δ 13.31; (s, 1H), 8.82; (dd, J=7.3, 1.7 Hz, 1H), 8.27-8.15; (m, 3H), 8.04; (dd, J=8.1, 1.7 Hz, 1H), 7.99-7.93; (m, 2H), 7.90; (d, J=5.3 Hz, 1H), 2.27-2.14; (m, 2H), 1.74; (dd, J=12.0, 8.4 Hz, 4H), 1.60; (t, J=11.9 Hz, 6H), 1.47; (d, J=13.0 Hz, 2H), 1.22; (s, 2H). Calculated MS (Maldi, m/z) [M$^-$H]$^{-H}$=652.138.

RSU-82B: N$^2$,N$^7$-di(bicyclo[1.1.1]pentan-1-yl)-9-(hydroxyimino)-9H-fluorene-2,7-disulfonamide: RSU_82A synthesized by general procedure A, followed by hydroxylamine hydrochloride (1 equivalent), and sodium hydroxide (10 equivalents) reacted according to General Procedure B. Yield: 65%. $^1$H NMR (400 MHz, DMSO-d$_6$) δ 13.35; (s, 1H), 8.88-8.72; (m, 1H), 8.25; (d, J=8.0 Hz, 1H), 8.21; (d, J=8.0 Hz, 1H), 8.16 (d, J=1.7 Hz, 1H), 8.02; (dd, J=8.1, 1.7 Hz, 1H), 7.94; (dd, J=8.0, 1.7 Hz, 1H), 2.29; (d, J=1.9 Hz, 2H), 1.75; (d, J=3.6 Hz, 12H). Calculated MS (Maldi, m/z) [M$^-$H]$^-$H=484.101.

RB-102: 9-((acryloyloxy)imino)-N$^2$,N$^7$-dicyclohexyl-9H-fluorene-2,7-disulfonamide: Fin56 (32 mg, 0.062 mmol), TEA (26 μL, 0.185 mmol) was dissolved in THF followed by Acroyl Chloride (25 μL, 0.309 mmol) and stirred until complete by TLC, then evaporated and purified by column chromatography (DCM/MeOH) to afford the product. Yield: 22 mg, 62%. $^1$H NMR (400 MHz, DMSO-d$_6$) δ 8.67; (d, J=1.6 Hz, 1H), 8.30-8.24; (m, 2H), 8.21; (dd, J=8.0, 0.6 Hz, 1H), 8.13; (dd, J=8.1, 1.7 Hz, 1H), 8.05; (dd, J=8.0, 1.7 Hz, 1H), 7.99; (d, J=7.4 Hz, 1H), 7.88; (d, J=7.3 Hz, 1H), 6.73-6.60; (m, 2H), 6.34; (dd, J=9.4, 2.2 Hz, 1H), 3.02; (s, 2H), 1.61; (dd, J=22.7, 8.9 Hz, 8H), 1.44; (d, J=12.2 Hz, 2H), 1.15; (q, J=10.0 Hz, 10H). Calculated MS (Maldi, m/z) [M$^+$H]$^{+H}$=572.188.

RB-122: 9-((acryloyloxy)imino)-N$^2$,N$^7$-di(bicyclo[2.2.1]heptan-2-yl)-9H-fluorene-2,7-disulfonamide: TKD1079 (35 mg, 0.065 mmol), TEA (27 μL, 0.195 mmol) was dissolved in THF followed by Acroyl Chloride (26 μL, 0.32 mmol) and stirred until complete by TLC, then evaporated and purified by column chromatography (DCM/MeOH) to afford the product. Yield: 18 mg, 47%. $^1$H NMR (400 MHz, DMSO-d$_6$) δ 8.66; (d, J=1.7 Hz, 1H), 8.27 -8.20; (m, 3H), 8.14-8.11; (m, 1H), 8.05-8.01; (m, 2H), 7.89; (d, J=7.1 Hz, 1H), 6.72-6.61; (m, 2H), 6.34; (dd, J=9.2, 2.3 Hz, 1H), 3.44; (s, 2H), 2.08-2.03; (m, 4H), 1.72-1.62; (m, 4H), 1.43-1.37; (m, 2H), 1.26-1.16; (m, 8H), 0.79; (d, J=3.6 Hz, 2H). Calculated MS (Maldi, m/z) [M$^+$H]$^{+H}$=596.188.

EK-030: N-(1-acryloylpiperidin-4-yl)-2-(((2,7-bis(N-cyclohexylsulfamoyl)-9H-fluoren-9-ylidene)amino)oxy)acetamide: FIN56 (40.4 mg, 0.078 mmol), N-(1-acryloylpiperidin-4-yl)-2-chloroacetamide (27 mg, 0.117 mmol), NaI (12 mg, 0.078 mmol) and K$_2$CO$_3$ (27 mg, 0.195 mmol) were mixed together in DMF/Acetonitrile and stirred at 50° C. until complete by TLC, then evaporated and purified by column chromatography (DCM/MeOH) to afford the product. Yield: 28 mg, 50%. $^1$H NMR (400 MHz, DMSO-d$_6$) δ 8.69; (s, 1H), 8.24; (d, J=8.0 Hz, 1H), 8.18; (d, J=8.0 Hz, 1H), 8.11-8.02; (m, 3H), 7.98; (dd, J=8.1, 1.6 Hz, 1H), 7.88; (d, J=7.3 Hz, 1H), 7.83; (d, J=7.3 Hz, 1H), 6.79; (dd, J=16.8, 10.6 Hz, 1H), 6.06; (dd, J=16.7, 2.4 Hz, 1H), 5.64; (dd, J=10.4, 2.4 Hz, 1H), 4.90; (s, 2H), 4.30; (d, J=13.2 Hz, 1H), 3.99; (d, J=14.7 Hz, 2H), 3.17; (t, J=12.9 Hz, 1H), 2.99; (s, 2H), 2.81; (t, J=12.4 Hz, 1H), 1.79; (s, 2H), 1.59; (t, J=10.9 Hz, 8H), 1.48-1.30; (m, 4H), 1.21-1.00; (m, 10H). Calculated MS (Maldi, m/z) [M$^+$H]$^{+H}$=712.283.

RB-132B: (Z)-N$^2$-((3s,5s,7s)-adamantan-1-yl)-N$^7$-(bicyclo[2.2.1]heptan-2-yl)-9-(hydroxyimino)-9H-fluorene-2,7-disulfonamide: 7-(N-(bicyclo[2.2.1]heptan-2-yl)sulfamoyl)-9-oxo-9H-fluorene-2-sulfonyl chloride (25 mg, 0.057 mmol) and adamantan-2-amine hydrochloride (21.4 mg, 0.114 mmol) were coupled by general procedure D to give RB-132A, followed by hydroxylamine hydrochloride (79 mg, 1.14 mmol), and sodium hydroxide (46 mg, 1.14 mmol) reacted according to General Procedure B. Yield: 21 mg, 63%. $^1$H NMR (400 MHz, DMSO-d$_6$) δ 13.29; (s, 1H), 8.82; (dd, J=14.6, 1.7 Hz, 1H), 8.25-8.12; (m, 3H), 8.07-7.87; (m, 3H), 7.83; (dd, J=6.8, 4.8 Hz, 1H), 3.42; (s, 1H), 3.27; (s, 1H), 2.00; (d, J=15.2 Hz, 4H), 1.74-1.58; (m, 12H), 1.40; (d, J=12.4 Hz, 2H), 1.27-1.13 (m, 4H), 1.01 - 0.76 (m, 2H). Calculated MS (Maldi, m/z) [M$^-$H]$^{-H}$=580.195.

RB-133B: (Z)-N$^2$-(bicyclo[2.2.1]heptan-2-yl)-N$^7$-(3-fluorocyclobutyl)-9-(hydroxyimino)-9H-fluorene-2,7-disulfonamide: 7-(N-(bicyclo[2.2.1]heptan-2-yl)sulfamoyl)-9-oxo-9H-fluorene-2-sulfonyl chloride (28 mg, 0.064 mmol) and 3-fluorocyclobutan-1-amine hydrochloride (16 mg, 0.127 mmol) were coupled by general procedure D to give RB-133A, followed by hydroxylamine hydrochloride (89 mg, 1.28 mmol), and sodium hydroxide (51 mg, 1.28 mmol) reacted according to General Procedure B. Yield: 15 mg, 45%. $^1$H NMR (400 MHz, DMSO-d$_6$) δ 13.33; (s, 1H), 8.80; (d, J=11.3 Hz, 1H), 8.22; (ddd, J=17.8, 7.8, 2.8 Hz, 3H), 8.17-8.09; (m, 1H), 8.01; (t, J=7.7 Hz, 1H), 7.97-7.79; (m, 2H), 4.75-4.59; (m, 1H), 3.90; (s, 1H), 2.47-2.42; (m, 1H), 2.31-2.1;1 (m, 2H), 2.06-1.89; (m, 3H), 1.65; (d, J=16.4 Hz, 2H), 1.49-1.29; (m, 2H), 1.27-1.11; (m, 4H), 0.79; (d, J=12.9 Hz, 1H). Calculated MS (Maldi, m/z) [M$^-$H]$^{-H}$=518.123.

RB-156B: (Z)-N$^2$-(bicyclo[1.1.1]pentan-1-yl)-N$^7$-(bicyclo[2.2.1]heptan-2-yl)-9-(hydroxyimino)-9H-fluorene-2,7- disulfonamide: 7-(N-(bicyclo[2.2.1]heptan-2-yl)sulfamoyl)-9-oxo-9H-fluorene-2-sulfonyl chloride (28 mg, 0.064 mmol) and bicyclo[1.1.1]pentan-1-amine hydrochloride (15.3 mg, 0.128 mmol) were coupled by general procedure D to give RB-156A, followed by hydroxylamine hydrochloride (89 mg, 1.28 mmol), and sodium hydroxide (51 mg, 1.28 mmol) reacted according to General Procedure B. Yield: 17 mg, 52%. $^1$H NMR (400 MHz, DMSO-$d_6$) δ 13.32; (s, 1H), 8.87-8.72; (m, 2H), 8.26-8.17; (m, 2H), 8.15; (d, J=1.7 Hz, 1H), 8.02; (dt, J=8.0, 1.5 Hz, 1H), 7.94; (dt, J=8.0, 1.9 Hz, 1H), 7.86; (dd, J=20.8, 7.0 Hz, 1H), 3.48-3.38; (m, 1H), 2.03; (dd, J=9.0, 4.4 Hz, 2H), 1.75; (d, J=3.7 Hz, 6H), 1.68-1.61; (m, 1H), 1.39; (s, 2H), 1.25-1.12; (m, 4H), 0.84-0.74; (m, 1H). Calculated MS (Maldi, m/z) [M$^-$H]$^{-H}$=512.132.

RB-157B: (E)-N$^2$-(bicyclo[2.2.1]heptan-2-yl)-9-(hydroxyimino)-N$^7$-(4-(trifluoromethyl)cyclohexyl)-9H-fluorene-2,7-disulfonamide: 7-(N-(bicyclo[2.2.1]heptan-2-yl)sulfamoyl)-9-oxo-9H-fluorene-2-sulfonyl chloride (30 mg, 0.068 mmol) and 4-(trifluoromethyl)cyclohexan-1-amine (31 µL 1.1,0.137 mmol) were coupled by general procedure D to give RB-157A, followed by hydroxylamine hydrochloride (94.5 mg, 1.36 mmol), and sodium hydroxide (54 mg, 1.36 mmol) reacted according to General Procedure B. Yield: 21 mg, 52%. $^1$H NMR (400 MHz, DMSO-$d_6$) δ 13.29; (s, 1H), 8.84-8.80; (m, 1H), 8.26-8.15; (m, 3H), 8.06-7.91; (m, 3H), 7.86; (dd, J=20.9, 7.1 Hz, 1H), 3.42; (dd, J=10.3, 5.1 Hz, 1H), 3.32; (s, 1H), 2.25-1.96; (m, 4H), 1.75; (s, 1H), 1.66-1.57; (m, 5H), 1.49-1.39; (m, 2H), 1.25-1.14; (m, 6H), 0.82-0.75; (m, 1H). Calculated MS (Maldi, m/z) [M$^-$H]$^{-H}$=596.151.

RB-158B: (E)-N$^2$-(bicyclo[2.2.1]heptan-2-yl)-9-(hydroxyimino)-N7-(spiro[3.3]heptan-2-yl)-9H-fluorene-2,7-disulfonamide: 7-(N-(bicyclo[2.2.1]heptan-2-yl)sulfamoyl)-9-oxo-9H-fluorene-2-sulfonyl chloride (32 mg, 0.073 mmol) and spiro[3.3]heptan-2-amine hydrochloride (22 mg, 0.146 mmol) were coupled by general procedure D to give RB-158A, followed by hydroxylamine hydrochloride (101.5 mg, 1.46 mmol), and sodium hydroxide (58.4 mg, 1.46 mmol) reacted according to General Procedure B. Yield: 25 mg, 63%. $^1$H NMR (400 MHz, DMSO-$d_6$) δ 13.20; (s, 1H), 8.79; (dd, J=18.1, 1.8 Hz, 1H), 8.25-8.10; (m, 3H), 8.08-7.98; (m, 2H), 7.96-7.80; (m, 2H), 3.52; (q, J=8.0 Hz, 1H), 3.42; (d, J=9.2 Hz, 1H), 2.12-1.99; (m, 4H), 1.90-1.85; (m, 2H), 1.79-1.60; (m, 8H), 1.43-1.33; (m, 1H), 1.31-1.13; (m, 4H), 0.79; (d, J=12.0 Hz, 1H). Calculated MS (Maldi, m/z) [M$^-$H]$^{-H}$=540.163.

RB-160B: (Z)-N$^2$-((1r,3r,5r,7r-adamantan-2-yl)-N$^7$-(bicyclo[1.1.1]pentan-1-yl)-9-(hydroxyimino)-9H-fluorene-2,7-disulfonamide: 7-(N-((1r,3r,5r,7r-adamantan-2-yl)sulfamoyl)-9-oxo-9H-fluorene-2-sulfonylchloride (24 mg, 0.049 mmol) and bicyclo[1.1.1]pentan-1-amine hydrochloride (11.6 mg, 0.098 mmol) were coupled by general procedure D to give RB-160A, followed by hydroxylamine hydrochloride (68.0 mg, 0.98 mmol), and sodium hydroxide (39 mg, 0.98 mmol) reacted according to General Procedure B. Yield: 15 mg, 55%. $^1$H NMR (400 MHz, DMSO-$d_6$) δ 13.31; (s, 1H), 8.83; (dd, J=13.9, 1.7 Hz, 2H), 8.25-8.14; (m, 3H), 8.07-7.83; (m, 3H), 3.27; (s, 1H), 2.00; (d, J=12.4 Hz, 2H), 1.75; (d, J=3.8 Hz, 6H), 1.73-1.54; (m, 10H), 1.40; (d, J=12.6 Hz, 2H). Calculated MS (Maldi, m/z) [M$^-$H]$^{-H}$=552.163.

RB-161B: (E)-N$^2$-((1r,3r,5r,7r-adamantan-2-yl)-9-(hydroxyimino)-N$^7$-(spiro[3.3]heptan-2-yl)-9H-fluorene-2,7-disulfonamide: 7-(N-((1r,3r,5r,7r-adamantan-2-yl)sulfamoyl)-9-oxo-9H-fluorene-2-sulfonyl chloride (24 mg, 0.049 mmol) and spiro[3.3]heptan-2-amine hydrochloride (14.4 mg, 0.098 mmol) were coupled by general procedure D to give RB-161A, followed by hydroxylamine hydrochloride (68.0 mg, 0.98 mmol), and sodium hydroxide (39 mg, 0.98 mmol) reacted according to General Procedure B. Yield: 20 mg, 70%. $^1$H NMR (400 MHz, DMSO-$d_6$) δ 13.30; (s, 1H), 8.81; (dd, J=32.9, 1.7 Hz, 1H), 8.25-8.17; (m, 2H), 8.13-7.96; (m, 3H), 7.97-7.79; (m, 2H), 3.58-3.47; (m, 1H), 3.26; (d, J=9.4 Hz, 1H), 2.09-1.96; (m, 4H), 1.88; (t, J=7.3 Hz, 2H), 1.79-1.57; (m, 15H), 1.40; (d, J=12.6 Hz, 2H), 0.86; (dd, J=6.6, 5.1 Hz, 1H). Calculated MS (Maldi, m/z) [M$^-$H]$^-$= 580.195.

RB-162B: (E)-N$^2$-((1r,3r,5r,7r-adamantan-2-yl)-9-(hydroxyimino)-N$^7$-(4-(trifluoromethyl)cyclohexyl)-9H-fluorene-2,7-disulfonamide: 7-(N-((1r,3r,5r,7r)-adamantan-2-yl)sulfamoyl)-9-oxo-9H-fluorene-2-sulfonyl chloride (24 mg, 0.049 mmol) and 4-(trifluoromethyl)cyclohexan-1-amine (14.4 µL, 0.098 mmol) were coupled by general procedure D to give RB-162A, followed by hydroxylamine hydrochloride (68.1 mg, 0.98 mmol), and sodium hydroxide (39 mg, 0.98 mmol) reacted according to General Procedure B. Yield: 15 mg, 48%. $^1$H NMR (400 MHz, DMSO-$d_6$) δ 13.30; (s, 1H), 8.87-8.78; (m, 1H), 8.26-8.14; (m, 3H), 8.08-8.02; (m, 1H), 7.99-7.83; (m, 3H), 3.29; (d, J=15.7 Hz, 2H), 2.18; (d, J=14.8 Hz, 1H), 2.00; (d, J=12.8 Hz, 2H), 1.79-1.65; (m, 8H), 1.64-1.56; (m, 7H), 1.40; (d, J=13.0 Hz, 3H), 1.31-1.16; (m, 2H). Calculated MS (Maldi, m/z) [M$^-$H]$^-$=636.182.

RB-163B: (E)-N$^2$-((1r,3r,5r,7r)-adamantan-2-yl)-N$^7$-(3-fluorocyclobutyl)-9-(hydroxyimino)-9H-fluorene-2,7-disulfonamide: 7-(N-((1r,3r,5r,7r)-adamantan-2-yl)sulfamoyl)-9-oxo-9H-fluorene-2-sulfonyl chloride (27 mg, 0.055 mmol) and 3-fluorocyclobutan-1-amine hydrochloride (14 mg, 0.110 mmol) were coupled by general procedure D to give RB-163A, followed by hydroxylamine hydrochloride (76.45 mg, 1.1 mmol), and sodium hydroxide (44 mg, 1.1 mmol) reacted according to General Procedure B. Yield: 20 mg, 65%. $^1$H NMR (400 MHz, DMSO-$d_6$) δ 13.31; (s, 1H), 8.81; (dd, J=26.9, 1.7 Hz, 1H), 8.26-8.18; (m, 3H), 8.13-8.04; (m, 1H), 7.99; (ddd, J=9.5, 8.0, 1.7 Hz, 1H), 7.94-7.89; (m, 1H), 7.85; (d, J=6.5 Hz, 1H), 4.80-4.52; (m, 1H), 3.27; (t, J=8.6 Hz, 2H), 2.45; (dd, J=6.5, 3.2 Hz, 1H), 2.37-2.03; (m, 2H), 2.02-1.90; (m, 3H), 1.74-1.55; (m, 10H), 1.40; (d, J=12.7 Hz, 2H). Calculated MS (Maldi, m/z) [M$^-$H]$^{-H}$=558.154.

Figure 2:
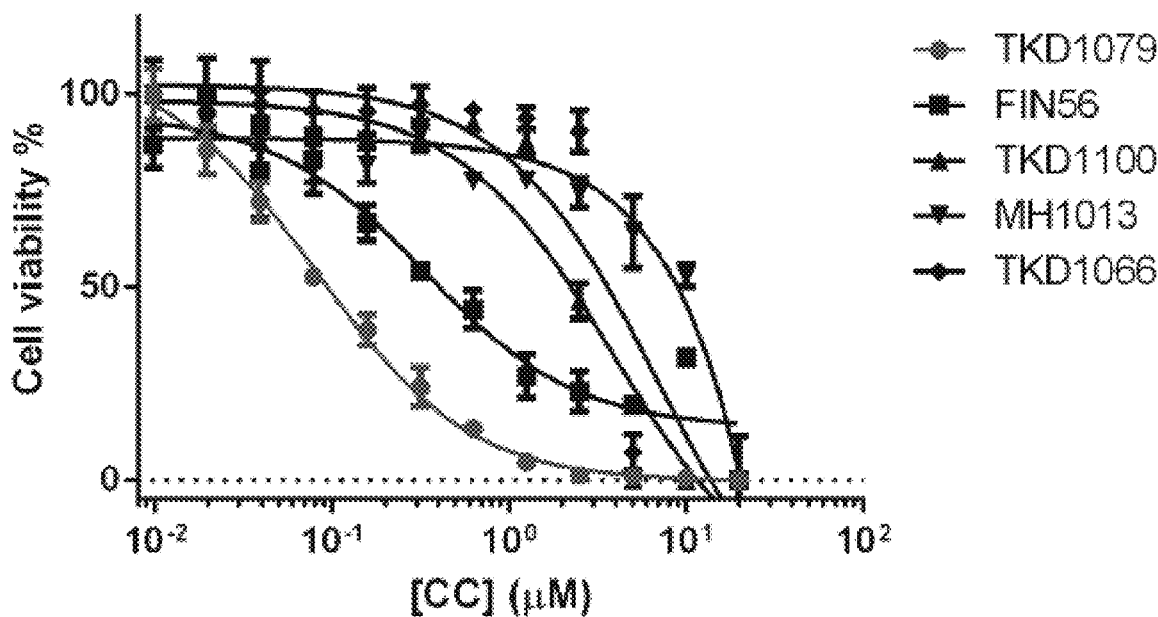
FIG. 2 shows the cell viability as a function of concentration for exemplary compounds.

Various compounds were selected for analysis of their cytotoxicity in HT-1080 cells according to the procedure described above. Table 1 shows compounds tested and the EC50 values determined from the study. FIG. 2 shows HT-1080 cell viability as a function of concentration of each compound tested.

TABLE 1

| Compound | Structure | Chemical Formula | MW | Solubility (clogP) | EC 50 (μM) |
| --- | --- | --- | --- | --- | --- |
| TKD1020 | 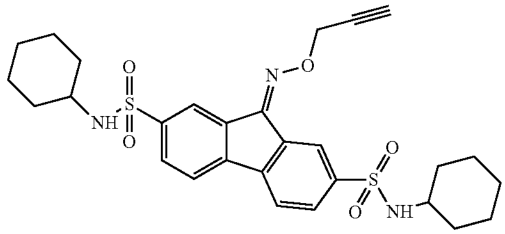 [SMILES: C#CCON=C1c2cc(S(=O)(=O)NC3CCCCC3)ccc2-c2ccc(S(=O)(=O)NC3CCCCC3)cc21] | C26H33N3O5S2 | 555.71 | 5.03 | 10.75 |
| MH1013 | 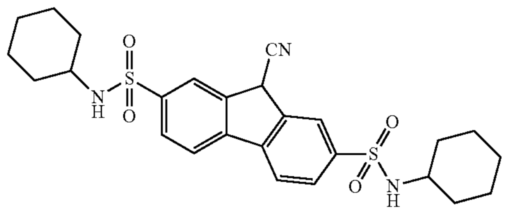 [SMILES: N#CC1c2cc(S(=O)(=O)NC3CCCCC3)ccc2-c2ccc(S(=O)(=O)NC3CCCCC3)cc21] | C26H31N3O4S2 | 513.16 | 5.26 | 13.36 |
| TKD1066 | 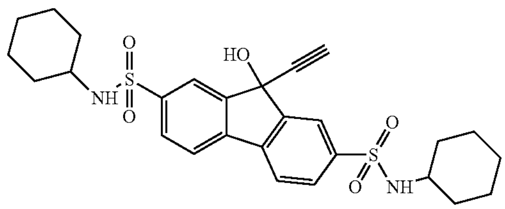 [SMILES: C#CC1(O)c2cc(S(=O)(=O)NC3CCCCC3)ccc2-c2ccc(S(=O)(=O)NC3CCCCC3)cc21] | C27H32N2O5S2 | 526.88 | 4.95 | 4.59 |
| TKD1100 | 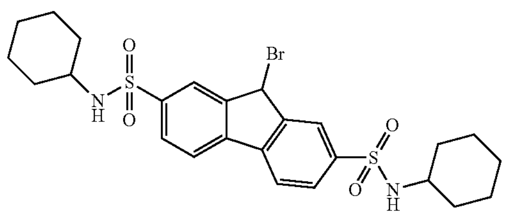 [SMILES: O=S(=O)(NC1CCCCC1)c1ccc2c(c1)C(Br)c1cc(S(=O)(=O)NC3CCCCC3)ccc1-2] | C25H31BrN2O4S2 | 567.58 | 6.45 | 3.56 |
| FIN56 | 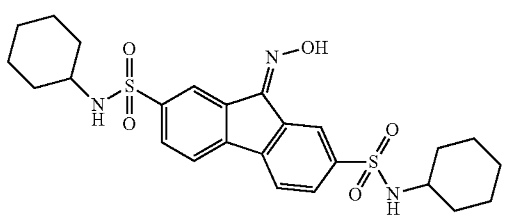 [SMILES: O=S(=O)(NC1CCCCC1)c1ccc2c(c1)C(=NO)c1cc(S(=O)(=O)NC3CCCCC3)ccc1-2] | C25H31N3O5S2 | 517.66 | 4.86 | 0.328 |
| TKD1079 | 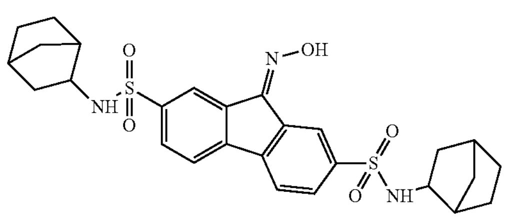 [SMILES: O=S(=O)(NC1CC2CCC1C2)c1ccc2c(c1)C(=NO)c1cc(S(=O)(=O)NC3CC4CCC3C4)ccc1-2] | C27H31N3O5S2 | 541.66 | 4.06 | 0.079 |

As shown in Table 1 and FIG. 2, the compound TKD1079 exhibited an $EC_{50}$ value of 0.079 μM, significantly lower than the $EC_{50}$ of comparative example FIN56 (see, e.g., U.S. Publication No. 2019/0315681).

Table 2 compares five additional compounds to both FIN56 and TKD1079. The cell viability as a function of concentration is provided in FIG. 3

TABLE 2

| Compound | Structure | Chemical Formula | MW | Solubility (clogP) | EC 50 (μM) |
|---|---|---|---|---|---|
| TKD1034A | 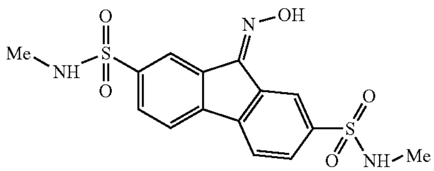 [SMILES: CNS(=O)(=O)c1ccc2c(c1)C(=NO)c1cc(S(=O)(=O)NC)ccc1-2] | C15H15N3O5S2 | 361.42 | 1.29 | 12.05 |
| TKD1034E | 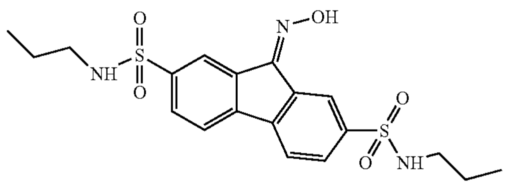 [SMILES: CCCNS(=O)(=O)c1ccc2c(c1)C(=NO)c1cc(S(=O)(=O)NCCC)ccc1-2] | C19H23N3O5S2 | 437.53 | 2.79 | 5.67 |
| TKD1027 | 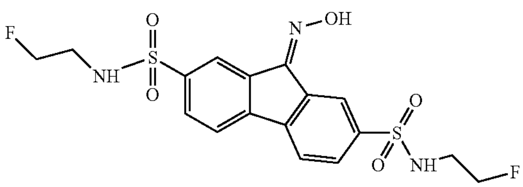 [SMILES: O=S(=O)(NCCF)c1ccc2c(c1)C(=NO)c1cc(S(=O)(=O)NCCF)ccc1-2] | C17H17F2N3O5S2 | 445.46 | 1.28 | >20 |
| TKD10416 | 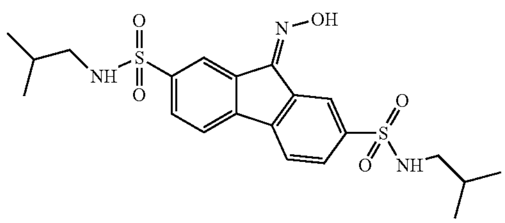 [SMILES: CC(C)CNS(=O)(=O)c1ccc2c(c1)C(=NO)c1cc(S(=O)(=O)NCC(C)C)ccc1-2] | C21H27N3O5S2 | 465.58 | 3.19 | 4.35 |
| TKD1034D | 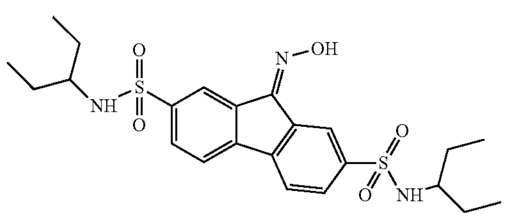 [SMILES: CCC(CC)NS(=O)(=O)c1ccc2c(c1)C(=NO)c1cc(S(=O)(=O)NC(CC)CC)ccc1-2] | C23H31N3O5S2 | 493.54 | 4.64 | 0.51 |
| FIN56 | 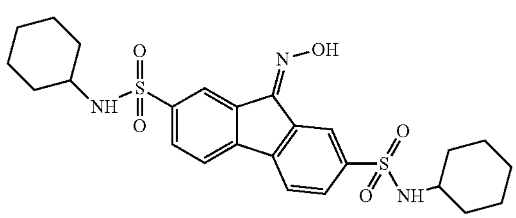 [SMILES: O=S(=O)(NC1CCCCC1)c1ccc2c(c1)C(=NO)c1cc(S(=O)(=O)NC3CCCCC3)ccc1-2] | C25H31N3O5S2 | 517.66 | 4.66 | 0.326 |
| TKD1079 | 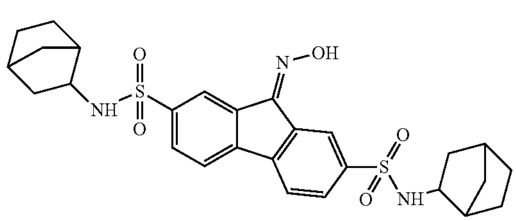 [SMILES: O=S(=O)(NC1CC2CCC1C2)c1ccc2c(c1)C(=NO)c1cc(S(=O)(=O)NC3CC4CCC3C4)ccc1-2] | C27H31N3O5S2 | 541.68 | 4.06 | 0.079 |

Figure 3:
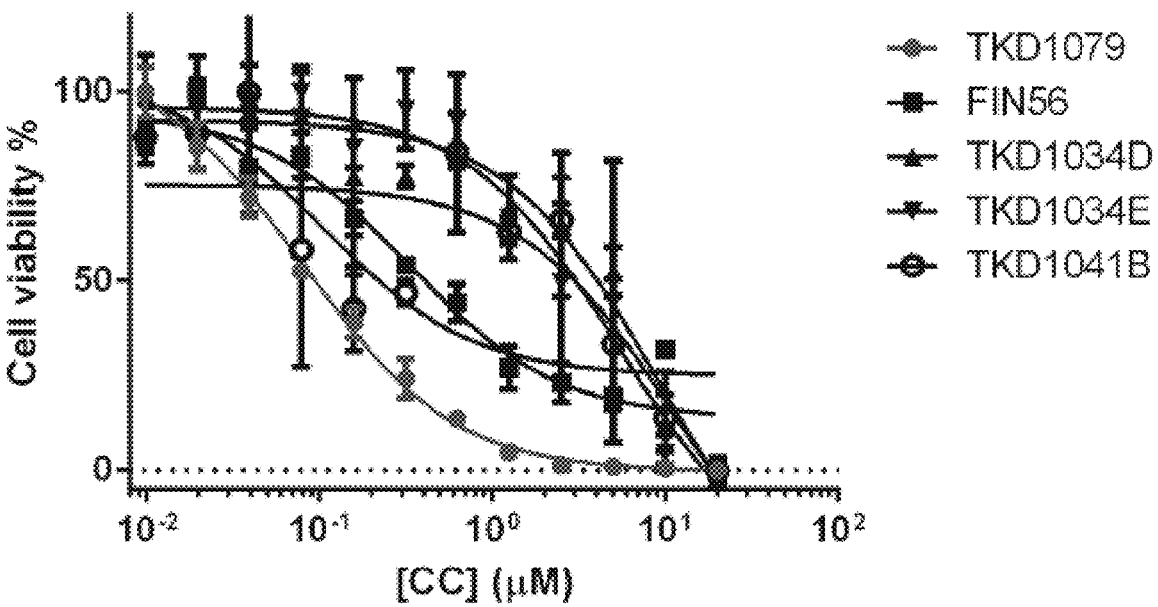
FIG. 3 shows the cell viability as a function of concentration for exemplary compounds.

As shown in Table 2 and FIG. 3, TKD1034D exhibited an $EC_{50}$ value of 0.51 μM, on par with that of FIN56.

Figure 4:
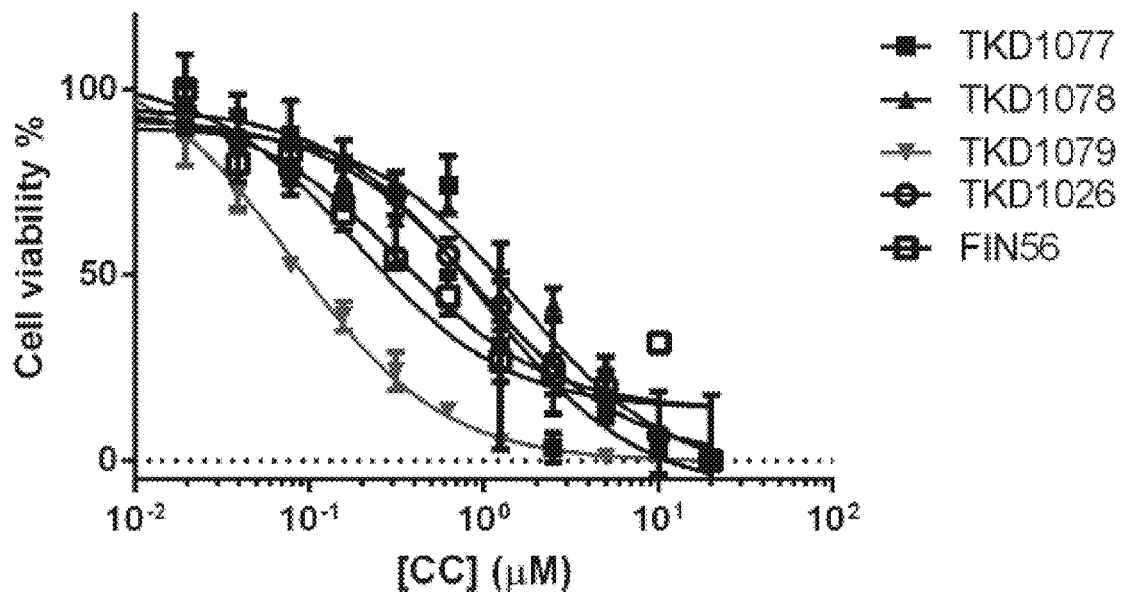
FIG. 4 shows the cell viability as a function of concentration for exemplary compounds.

Table 3 shows the structure activity relationship of three additional compounds as compared to FIN56 and TKD1079. FIG. 4 shows the cell viability as a function of concentration for these analogs.

TABLE 3

| Compound | Structure | Chemical Formula | MW | Solubility (clogP) | EC 50 (μM) |
|---|---|---|---|---|---|
| TKD1026 | 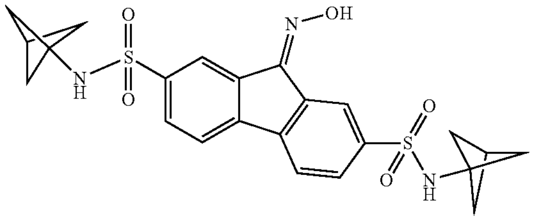 [SMILES: O=S(=O)(NC12CC(C1)C2)c1ccc2c(c1)C(=NO)c1cc(S(=O)(=O)NC34CC(C3)C4)ccc1-2] | C23H23N3O5S2 | 485.57 | 2.52 | 1.7 |
| TKD1077 | 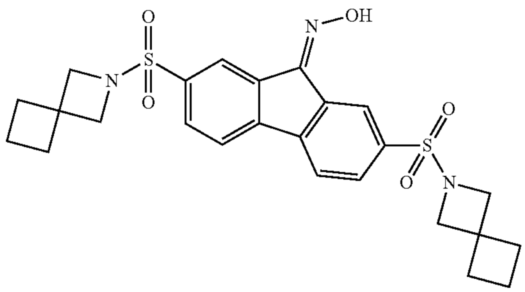 [SMILES: O=S(=O)(c1ccc2c(c1)C(=NO)c1cc(S(=O)(=O)N3CC4(CCC4)C3)ccc1-2)N1CC2(CCC2)C1] | C25H27N3O5S2 | 513.63 | 3.62 | 0.99 |
| TKD1078 | 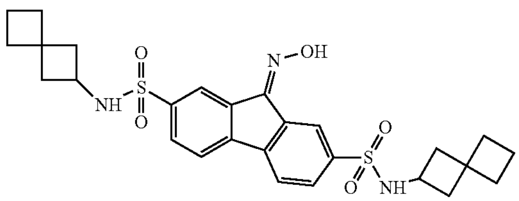 [SMILES: O=S(=O)(NC1CC2(CCC2)C1)c1ccc2c(c1)C(=NO)c1cc(S(=O)(=O)NC3CC4(CCC4)C3)ccc1-2] | C27H31N3O5S2 | 541.68 | 5.25 | 0.69 |
| FIN56 | 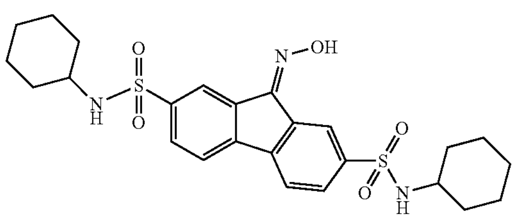 [SMILES: O=S(=O)(NC1CCCCC1)c1ccc2c(c1)C(=NO)c1cc(S(=O)(=O)NC3CCCCC3)ccc1-2] | C25H31N3O5S2 | 517.66 | 4.86 | 0.328 |
| TKD1079 | 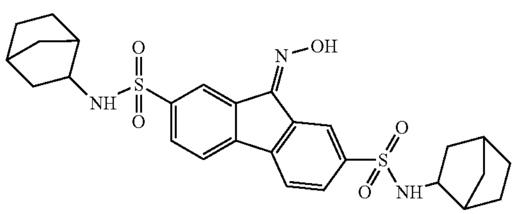 [SMILES: O=S(=O)(NC1CC2CCC1C2)c1ccc2c(c1)C(=NO)c1cc(S(=O)(=O)NC3CC4CCC3C4)ccc1-2] | C27H31N3O5S2 | 541.68 | 4.06 | 0.079 |

As shown in Table 3, each of TKD1026, TKD1077, and TKD1078 exhibited $EC_{50}$ values of less than 2 μM, with TKD1078 exhibiting an $EC_{50}$ value of 0.59 μM.

TKD1079 was selected as a lead compound for further analysis and comparison to FIN56. As shown in the Tables above, TKD1079 exhibited an $EC_{50}$ value of 0.079 μM, while FIN56 exhibited an $EC_{50}$ value of 0.328 μM.

Figure 5:
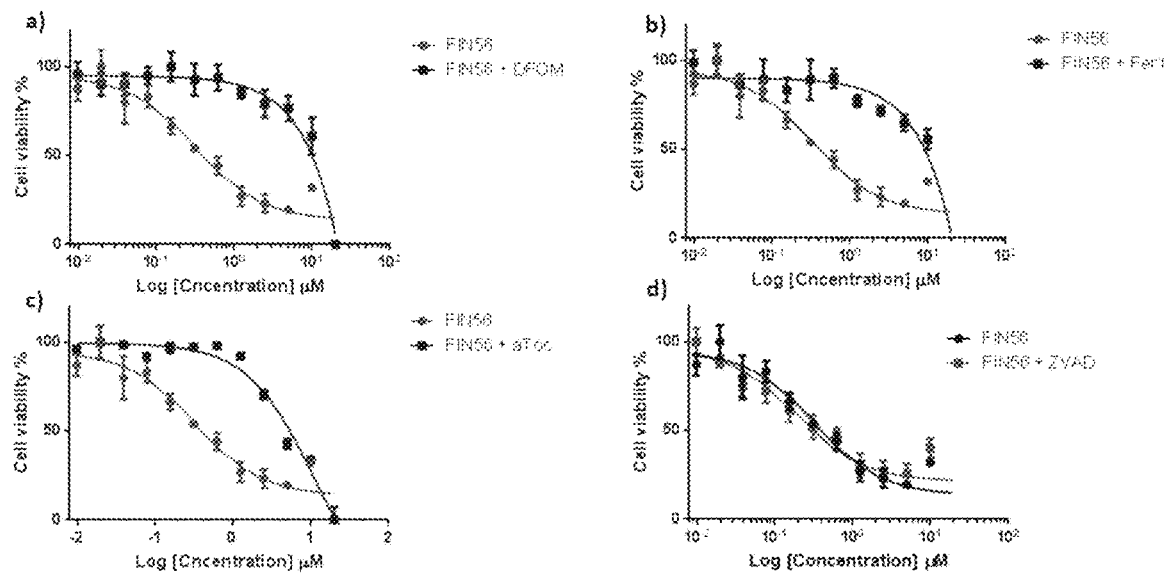
FIG. 5 shows the effects of FIN56 after 48 hour incubation with HT-1080 cells when cotreated with (a) deferoxamine (DFOM, 152 μM); (b) ferrostatin-1 (Fer-1, 500 nM); and (c) α-tocopherol (αToc, 100 μM). (d) The apoptosis inhibitor pathway (ZVAD, 45 μM) did not block FIN56.

FIG. 5 shows the effects of FIN56 after 48 hour incubation with HT-1080 cells when cotreated with (a) deferoxamine (DFOM, 152 μM); (b) ferrostatin-1 (Fer-1, 500 nM); and (c) α-tocopherol (αToc, 100 μM). FIG. 4(d) shows that the apoptosis inhibitor pathway (ZVAD, 45 μM) did not block FIN56. These results, including the $EC_{50}$ values, are summarized in Table 4.

TABLE 4

| Inhibitor | EC50 (μM) of FIN56 | EC50 (μM) of FIN56 + inhbitor | Slectivity in fold [EC50 (FIN56 + inhibitor)/ EC50 inhbitor] |
|---|---|---|---|
| DFOM (152 μM) | 0.3283 | >20 | >60 |
| Fer 1 (500 nM) | 0.3283 | >30 | >90 |
| aToc (100 μM) | 0.3283 | 11.47 | 34.8 |
| ZVAD (45 μM) | 0.3283 | 0.196 | 0.6 |

Figure 6:
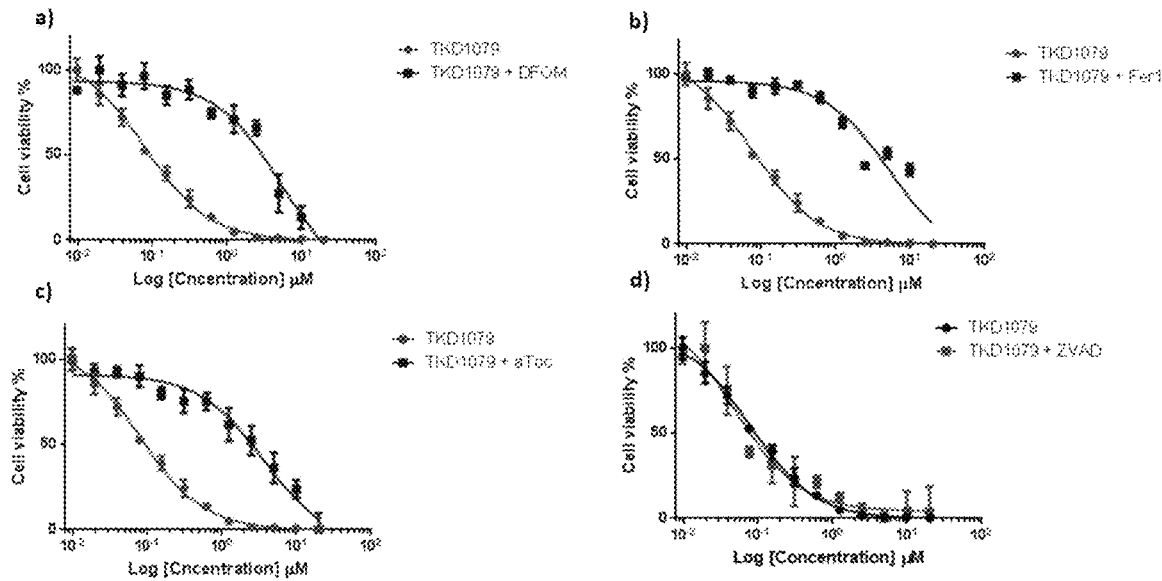
FIG. 6 shows the effects of the ferroptosis inducer TKD1079 for 48 hours on the viability of HT-1080 cells when co-treated with (a) deferoxamine (DFOM, 152 μM); (b) ferrostatin-1 (Fer-1, 500 nM); and (c) α-tocopherol (αToc, 100 μM). (d) The apoptosis inhibitor pathway (ZVAD, 45 μM) did not block TKD1079.

FIG. 6 shows the effects of the ferroptosis inducer TKD1079 for 48 hours on the viability of HT-1080 cells when co-treated with various inhibitors. FIG. 6(a) shows cotreating with deferoxamine (DFOM, 152 μM); (b) ferrostatin-1 (Fer-1, 500 nM); and (c) α-tocopherol (αToc, 100

µM). FIG. 6(d) shows that the apoptosis inhibitor pathway (ZVAD, 45 µM) did not block TKD1079. These results, including the $EC_{50}$ values, are summarized in Table 5.

TABLE 5

| Inhibitor | EC50 (µM) of TKD1079 | EC50 (µM) of TKD1079 + inhbitor | Slectivity in fold [EC50 (TKD1079 + inhibitor)/ EC50 inhbitor] |
|---|---|---|---|
| DFOM (152 µM) | 0.0797 | 2.7300 | 34.2 |
| Fer 1 (500 nM) | 0.0797 | 5.4820 | 68.8 |
| aToc (100 µM) | 0.0797 | 1.0790 | 13.5 |
| ZVAD (45 µM) | 0.0797 | 0.0510 | 0.6 |

Figure 7:
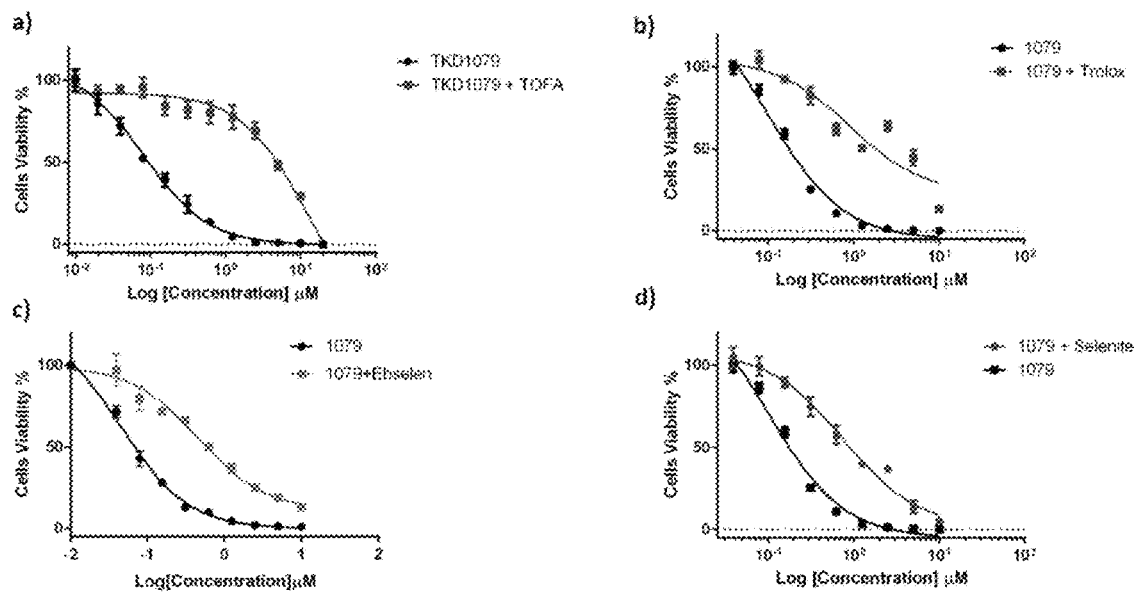
FIG. 7 shows the effects of TKD1079 after 48 hour incubation with HT-1080 cells when cotreated with (a) TOFA (5 μM); (b) Trolox (150 μM); (c) Ebselen (5 μM); and (d) selenite (100 nM).

FIG. 7 shows the effects of TKD1079 after 48 hour incubation with HT-1080 cells when cotreated with (a) TOFA (5 µM); (b) Trolox (150 µM); (c) Ebselen (5 µM); and (d) selenite (100 nM). The results, including the $EC_{50}$ values, are summarized in Table 6.

TABLE 6

| Inhibitor | EC50 (µM) of TKD1079 | EC50 (µM) of TKD1079 + inhbitor | Slectivity in fold [EC50 (TDK1079 + inhibitor)/ EC50 inhbitor] |
|---|---|---|---|
| TOFA (10 µM) | 0.0797 | 11.8500 | 148.7 |
| Trolox (100 µM) | 0.0797 | 0.9244 | 11.6 |
| Ebselen (5 µM) | 0.0797 | 0.4588 | 5.8 |
| Selenite (100 nM) | 0.0797 | 0.7575 | 9.5 |

Figure 8:
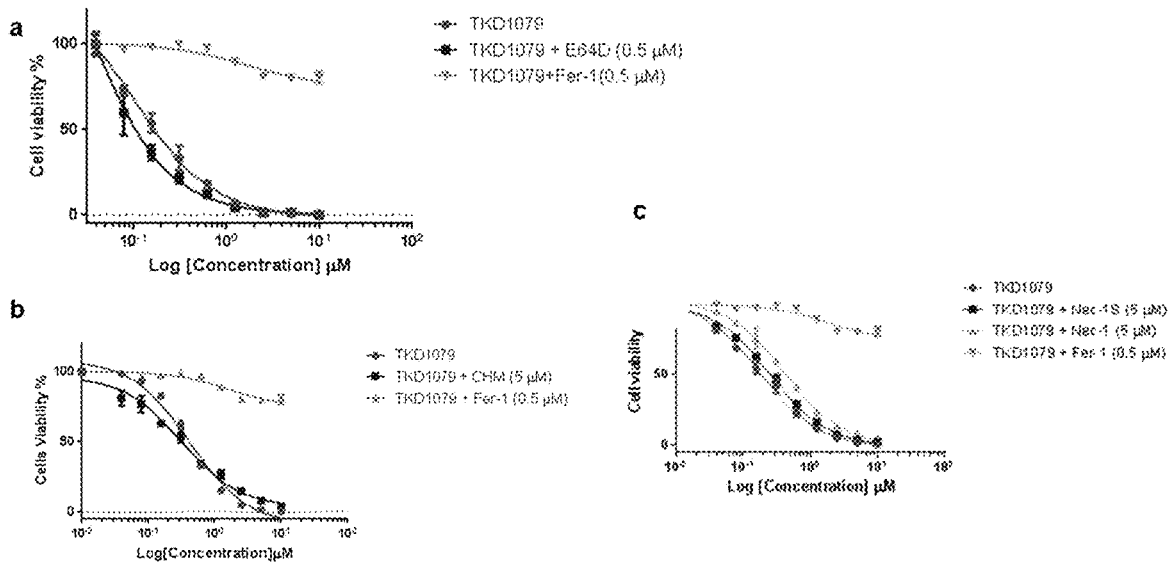
FIG. 8 shows the effects of TKD1079 after 48 hour incubation with HT-1080 cells when cotreated with E64D at 400 μM, cycloheximide (CHM) at 5 μM, ferrostatin-1 (Fer-1) at 0.5 μM, necrostatin1 (Nec-1) at 5 μM, and necrostatin-1S (Nec-1S) at 5 μM.

FIG. 8 shows the effects of the ferroptosis inducer TKD1079 for 48 hours on the viability of HT-1080 cells when co-treated with various inhibitors. FIG. 8(a) shows cotreating with E64D at 400 µM; (b) cycloheximide (CHM) at 5 µM; (c) Necrostatin1 (Nec-1) at 5 µM and Necrostatin-1S (Nec-1S) at 5 µM. Cotreating with Ferrostatin-1 (Fer-1) at 0.5 µM is also shown for comparison in each of FIG. 8(a)-(c).

Figure 9:
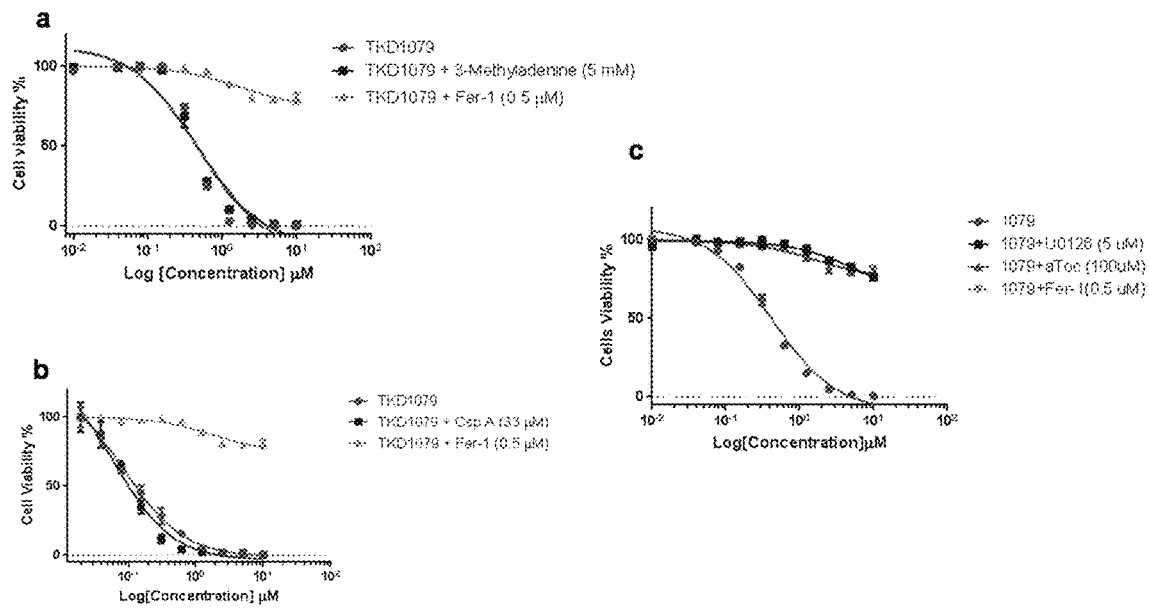
FIG. 9 shows the effects of the ferroptosis inducer TKD1079 for 48 hours on the viability of HT-1080 cells when co-treated with various inhibitors including (a) 3-Methyladenine (3MA) at 5 μM, (b) Cyclosporine A (CspA) at 33 μM (c) alpha tocopherol (a-Toc) at 100 μM, U0126 at 5 μM.

FIG. 9 shows the effects of the ferroptosis inducer TKD1079 for 48 hours on the viability of HT-1080 cells when co-treated with various inhibitors including (a) 3-Methyladenine (3MA) at 5 µM, (b) Cyclosporine A (CspA) at 33 µM (c) alpha tocopherol (α-Toc) at 100 µM, U0126 at 5 µM.

Figure 10:
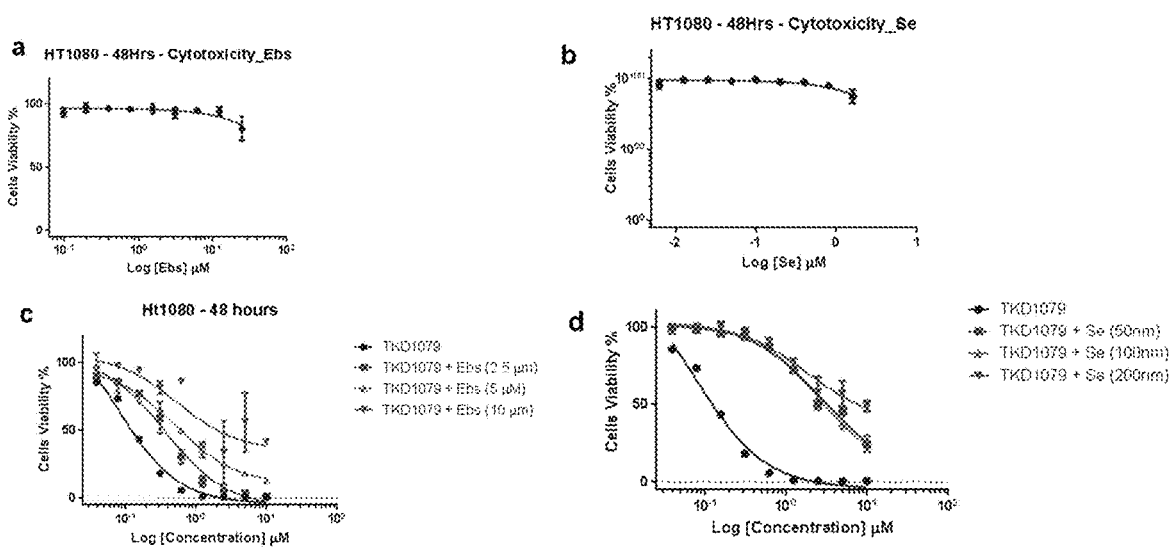
FIG. 10 shows the effects of the ferroptosis inducer TKD1079 for 48 hours on the viability of HT-1080 cells when co-treated with various inhibitors including (a) Ebselen (Ebs) and (b) Selenite (Se) alone, (c) Ebselen (5 μM), and (d) selenite (100 nM).

FIG. 10 shows the effects of the ferroptosis inducer TKD1079 for 48 hours on the viability of HT-1080 cells when co-treated with various inhibitors including (a) Ebselen (Ebs) and (b) Selenite (Se) alone, (c) Ebselen (5 µM), and (d) selenite (100 nM).

Figure 11:
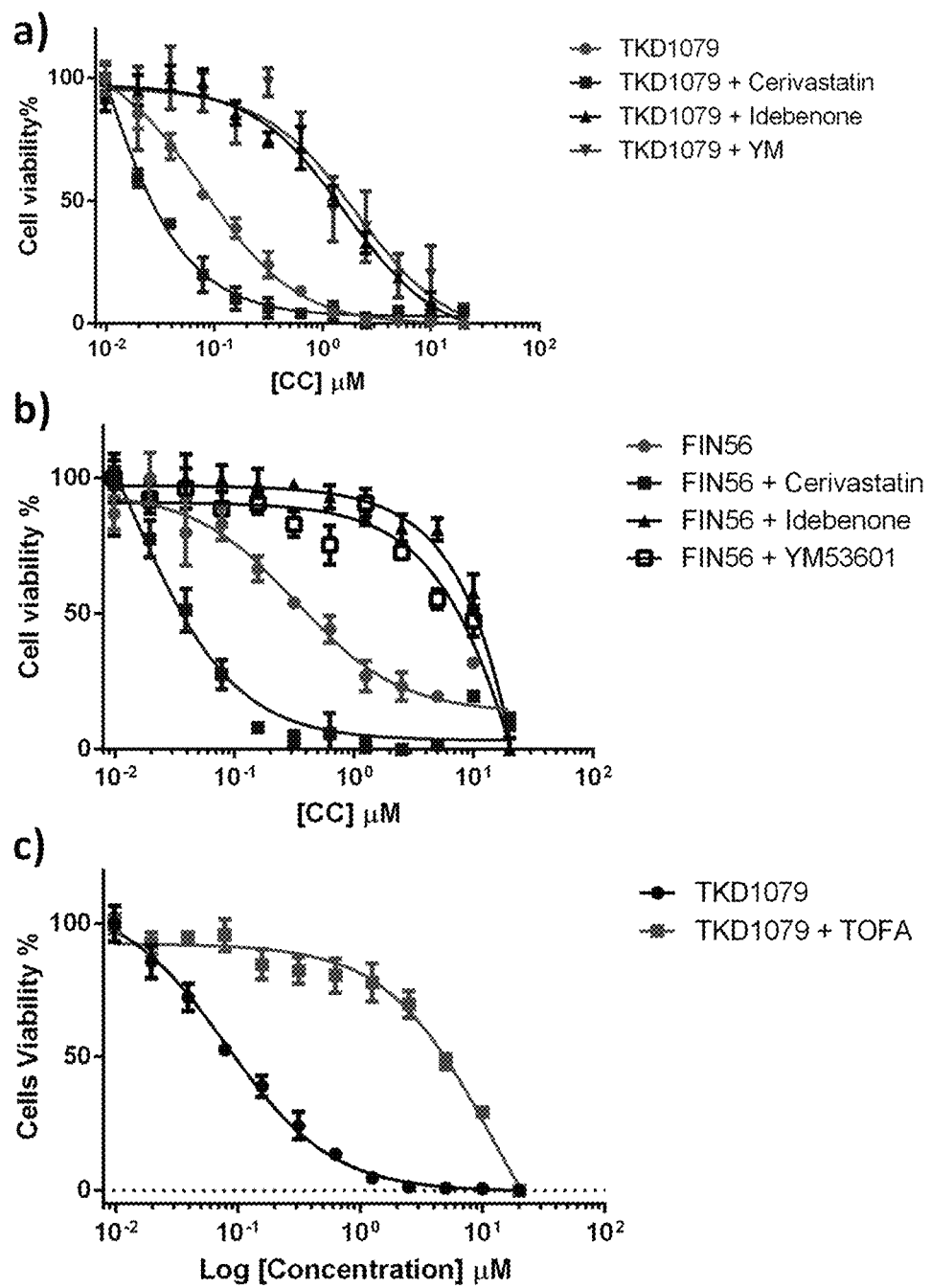
FIG. 11 shows the effects of ferroptosis inducer TKD1079 and FIN56 for 48 hon viability of HT-1080 cells co-treated with inhibitors. a) TKD1079. b) FIN56. C) TKD1079+/– acetyl-CoA carboxylase (ACC) inhibitor TOFA. Cerivastatin (5 μM), Idebenone (10 μM), the Squalene synthase inhibitor YM53601 (5 μM) and 5-(tetradecyloxy)-2-furoic acid (TOFA, 10 μM).

FIG. 11 shows the effects of ferroptosis inducer TKD1079 and FIN56 for 48 h on viability of HT-1080 cells co-treated with inhibitors. Cell viability of TKD1079 alone and in the presence of cerivastatin (5 µM), idebenone (10 µM), the squalene synthase inhibitor YM53601 (5 µM) are shown FIG. 11(a). Cell viability of FIN56 alone and in the presence of cerivastatin (5 µM), idebenone (10 µM), the squalene synthase inhibitor YM53601 (5 µM) are shown FIG. 11(b). Cell viability of TKD1079 alone and in the presence of acetyl-CoA carboxylase (ACC) inhibitor (TOFA) is shown in FIG. 11(c).

Figure 12:
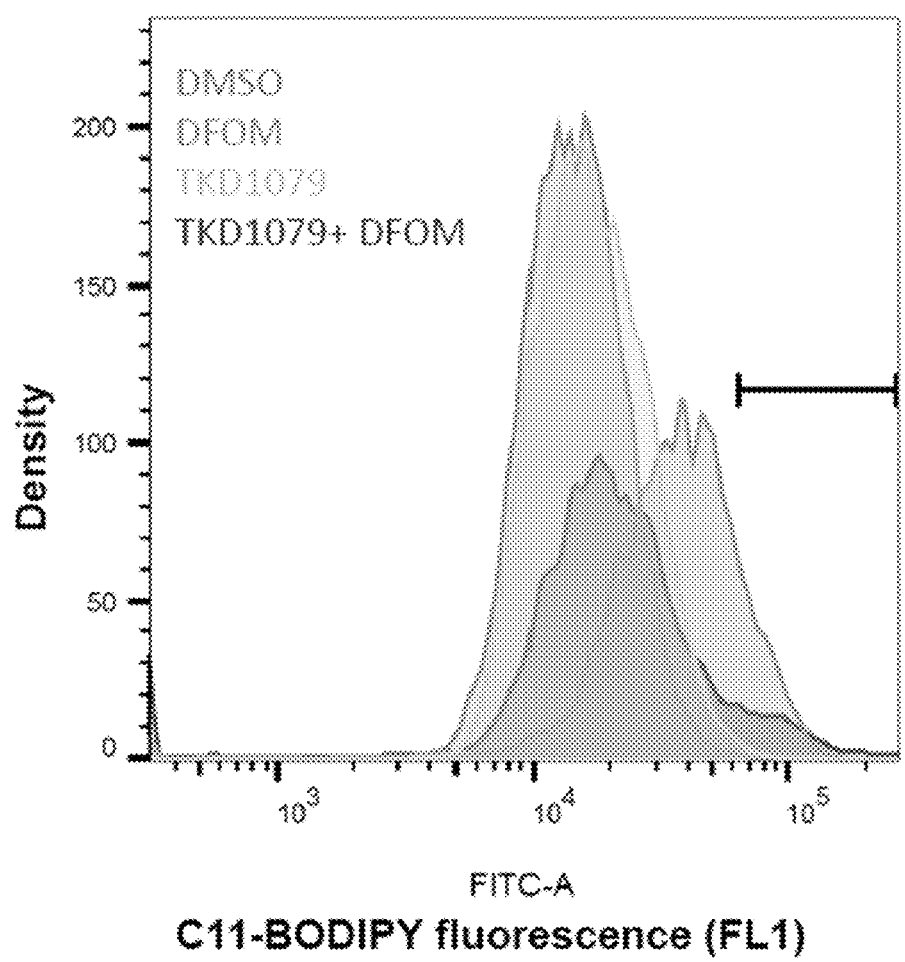
FIG. 12 shows the lipid ROS production assessed over time (4 hours) of TKD1079 treatment to HT-1080 cells analyzed by flow cytometry using C11-BODIPY (2 μM).

FIG. 12 shows the lipid ROS production assessed over time (4 hours) of TKD1079 treatment to HT-1080 cells analyzed by flow cytometry using C11-BODIPY (2 µM). The results show that the lipid ROS generation during cell death induced by the compound TKD1079 increased at 4 hours.

Figure 13:
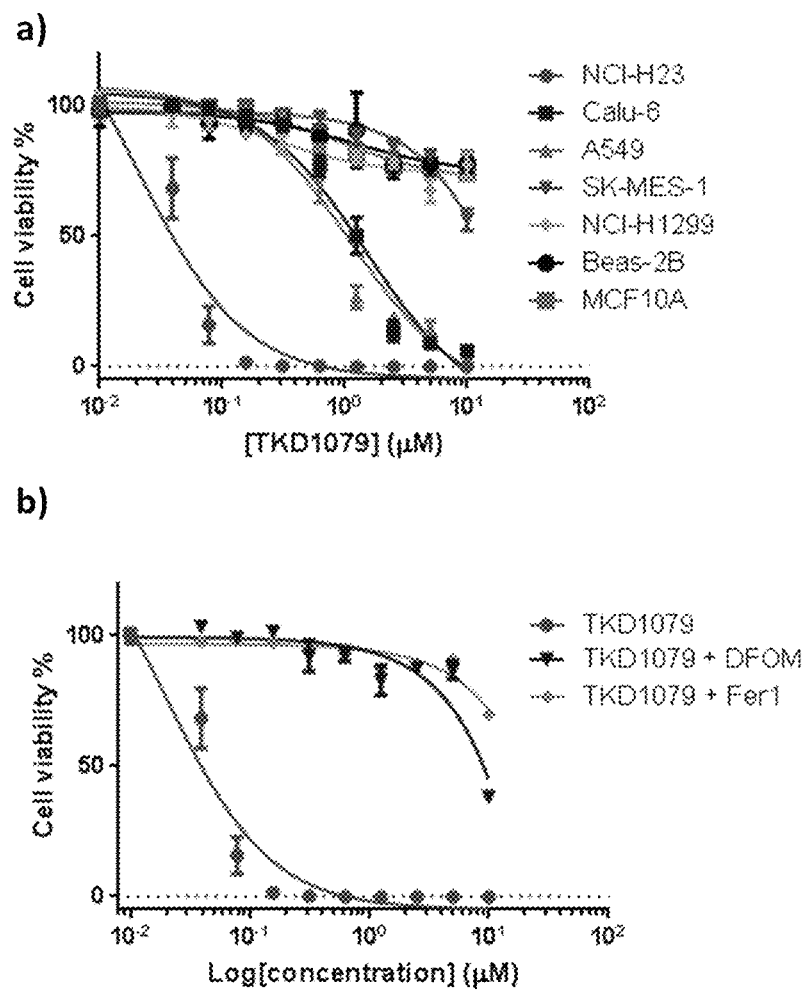
FIG. 13 shows the cell viability as a function of concentration for an exemplary compound against seven cell types.

In addition, the compound TKD1079 was also analyzed for cytotoxicity in four different lung cancer cell lines according to the procedure described above. NCI-H23 is human non-small cell lung carcinoma with KRAS mutation. SK-Mes-1 is human non-small cell lung carcinoma with KRAS wild type. Calu6 is human non-small cell lung carcinoma. A549 is human non-small cell lung carcinoma. Cytotoxicity was also determined against MCF10A non-malignant breast epithelial cell, NCI-H1299 human non-small cell lung carcinoma cell line, and Beas-2B epithelial cells isolated from normal human bronchial epithelium. FIG. 13 shows cell viability for each cell line as a function of concentration of TKD1079. As shown in FIG. 13, TKD1079 was observed to be highly potent against the NCI-H23 cells. TKD1079 also exhibited selective cytotoxicity in NSCLC cells without harming normal human lung Beas-2B and breast MCF10A cells. As shown in FIG. 13(b), TKD1079 induces ferroptosis in NCI-H23 using ferroptosis inhibitors (DFOM (152 µM) and Fer-1 (0.5 µM). The viability assay was conducted for 48 hours.

Figure 14:
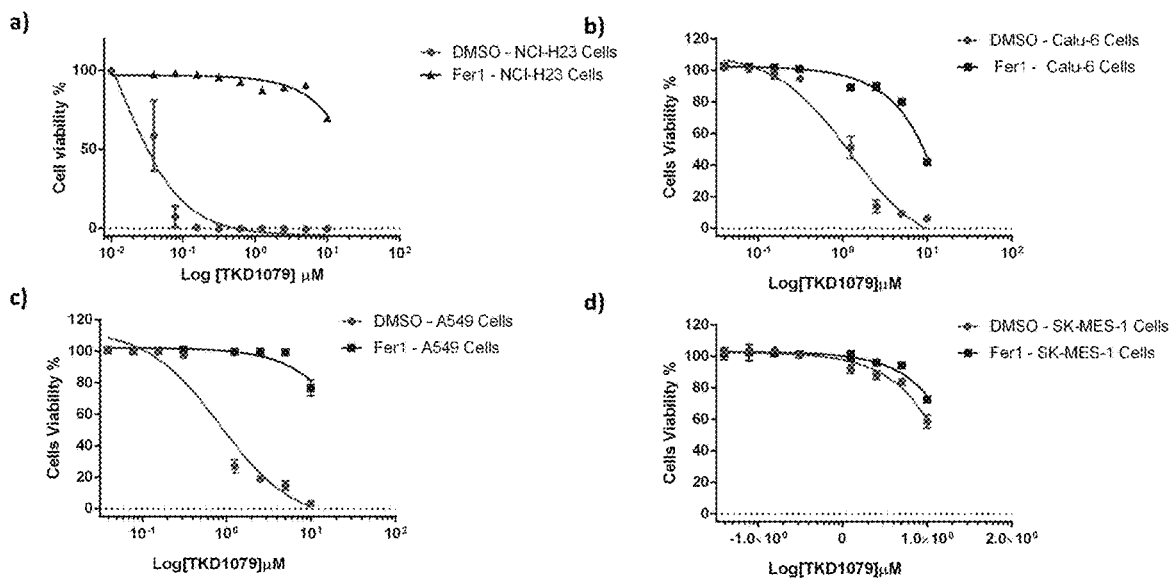
FIG. 14 shows the effects of a ferroptosis inducer for 48 h on viability of four types of lung cancer cells cotreated with ferrostatin-1 (Fer-1, 500 nM). (a) NCI-H23 (b) Calu6; (c) A549; d) SK-Mes-1.

FIG. 14 shows the effect of TKD1079 against four lung cancer cell lines when cotreated with ferrostatin-1 (Fer-1, 500 nM). FIG. 11 shows that the cytotoxicity of TKD1079 was blocked in the presence of Fer-1, confirming a ferroptosis cell death pathway was responsible for the observed cytotoxicity.

Figure 15:
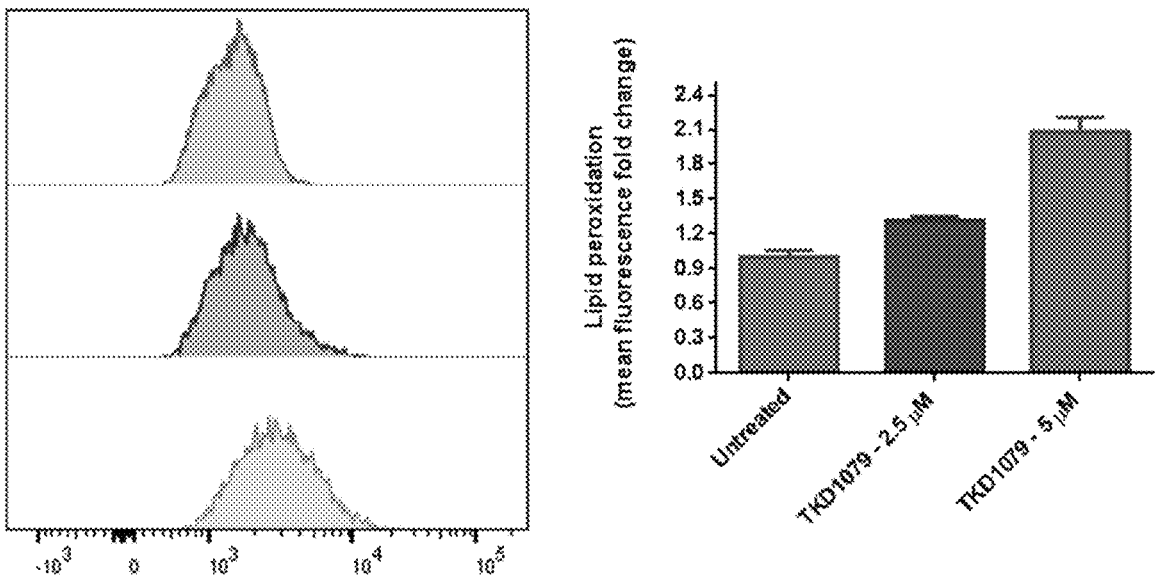
FIG. 15 shows histogram visualization of each treatment (left) and quantification of lipid peroxidation generated under TKD1079 treatment represented by mean C11-BODIPY fluorescence fold change measured by Flow cytometry.

The lipid peroxidation level of TK1079 at 2.5 µM and 5 µM respectively for 3 hours in a human fibrosarcoma HT1080 cell line was assessed using C11-Bodipy and flow cytometry. FIG. 15 shows a histogram visualization of each treatment (left). Also shown is quantification of lipid peroxidation generated under TKD1079 treatment represented by mean C11-BODIPY fluorescence fold change measured by Flow cytometry.

Figure 16:
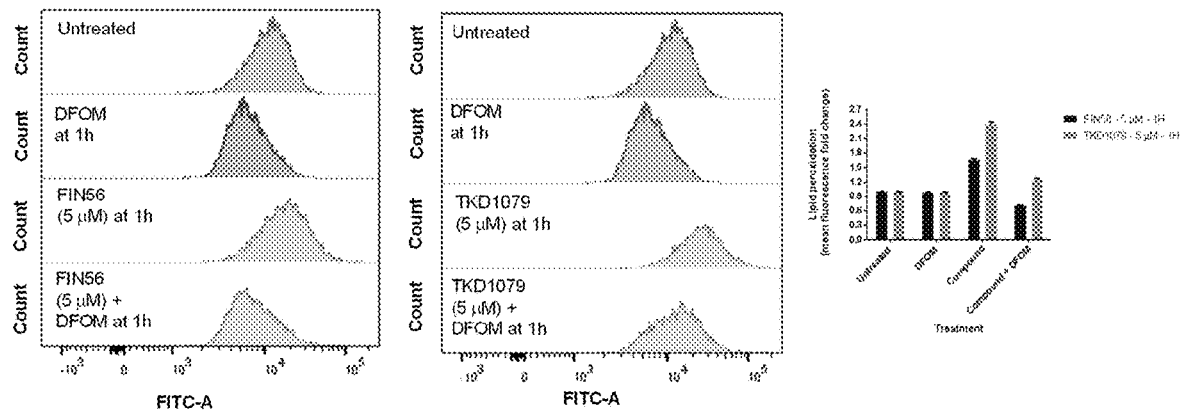
FIG. 16 shows histogram visualization of each treatment (left) and quantification of lipid peroxidation generated under drug represented by mean C11-BODIPY fluorescence fold change measured by Flow cytometry.

Lipid peroxidation of FIN56 and TKD1079 was assessed at 5 µM for 1 hour using a human fibrosarcoma HT1080 cell line and C11-Bodipy. FIG. 16 shows a histogram visualization of each treatment (left). The iron chelator deferoxamine (DFOM) treatment was at 150 µM. Also shown is quantification of lipid peroxidation generated under TKD1079 or FIN56 treatment represented by mean C11-BODIPY fluorescence fold change measured by Flow cytometry. Similar results were obtained after 2, 3, and 4 hour incubations.

Figure 17:
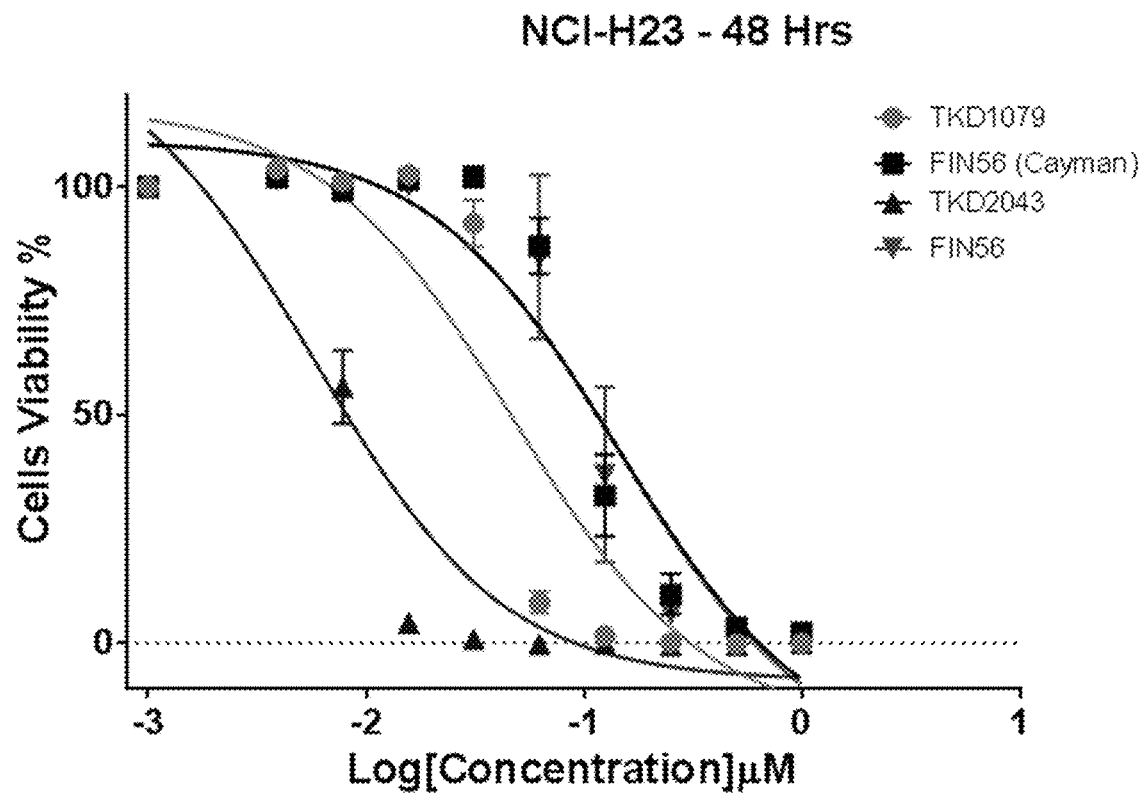
FIG. 17 shows the cell viability as a function of concentration for exemplary compounds.

The compound TKD2043 was also further analyzed for cytotoxicity relative to TKD1079 and FIN56 analogs in NCI-H23 cells after 48 hours. FIG. 17 shows the results of the cell viability study. As shown in FIG. 17, TKD2043 is significantly more potent than TKD1079 and FIN56.

Figure 18:
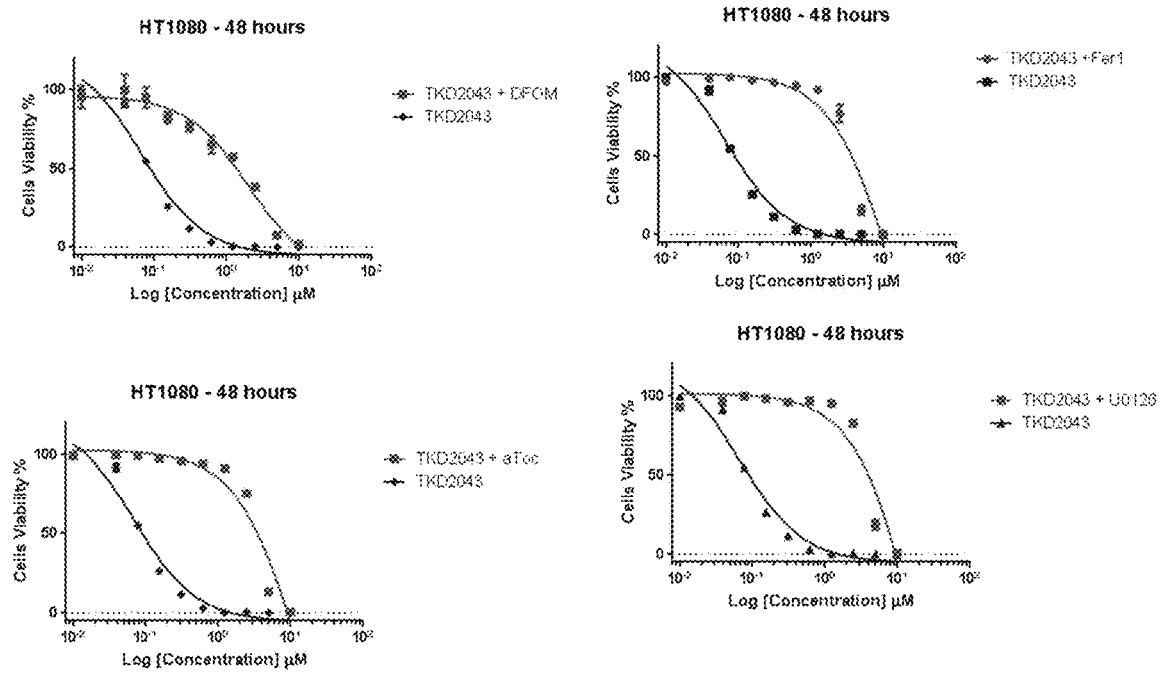
FIG. 18 shows the effects of TKD2043 after 48 hour incubation with HT-1080 cells when cotreated with deferoxamine (DFOM, 152 μM); ferrostatin-1 (Fer-1, 500 nM); α-tocopherol (αToc, 100 μM), and U0126 at 5 μM.

FIG. 18 shows the effects of TKD2043 after 48 hour incubation with HT-1080 cells when cotreated with deferoxamine (DFOM, 152 µM); ferrostatin-1 (Fer-1, 500 nM); and α-tocopherol (αToc, 100 µM), and U0126 at 5 µM.

Figure 19:
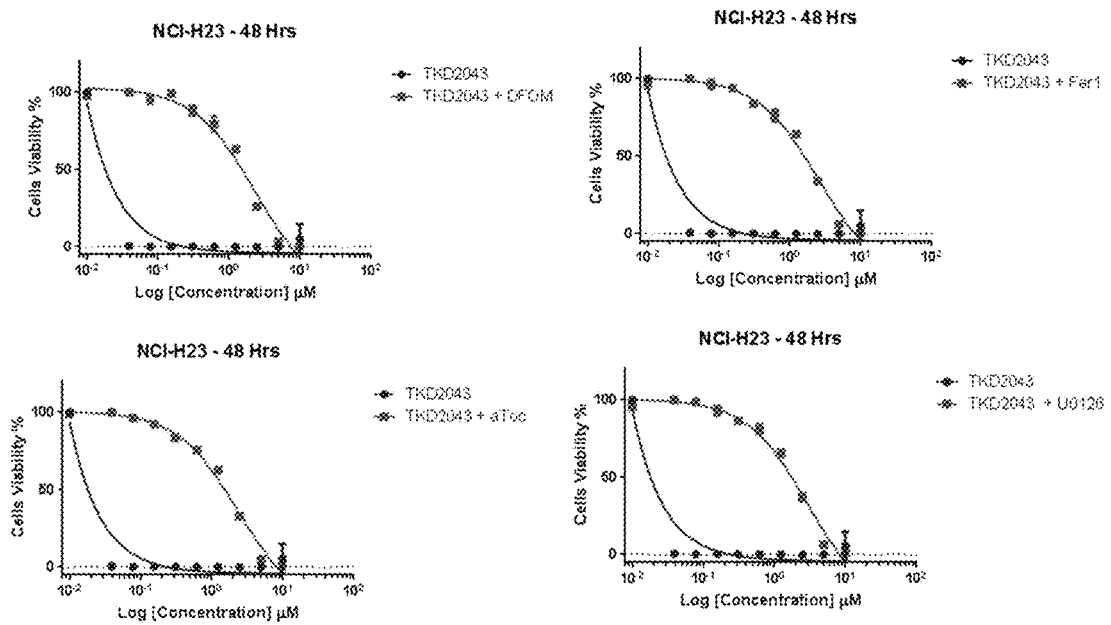
FIG. 19 shows the effects of TKD2043 after 48 hour incubation with NCI-H23 cells when cotreated with deferoxamine (DFOM, 152 μM); ferrostatin-1 (Fer-1, 500 nM); α-tocopherol (αToc, 100 μM), and U0126 at 5 μM

FIG. 19 shows the effects of TKD2043 after 48 hour incubation with NCI-H23 cells when cotreated with deferoxamine (DFOM, 152 µM); ferrostatin-1 (Fer-1, 500 nM); and α-tocopherol (αToc, 100 µM), and U0126 at 5 µM.

This disclosure further encompasses the following aspects, which are non-limiting.

Aspect 1: A compound according to Formula 1

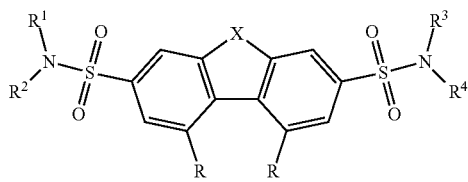

wherein X is —CH$_2$—, —(C=O)—, —(C=N—NH$_2$)—,

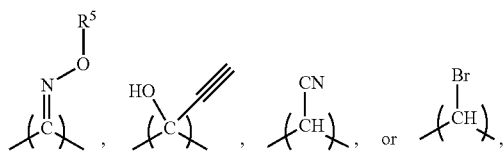

wherein R$^5$ is hydrogen, a C$_{1-6}$ alkyl group, a propargyl group, or a (meth)acrylate group; R is independently at each occurrence hydrogen, a C$_{1-6}$ alkyl group, —NO$_2$, —NH$_2$, —OH, a group of the formula

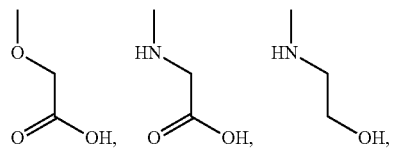

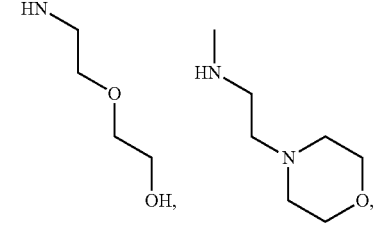

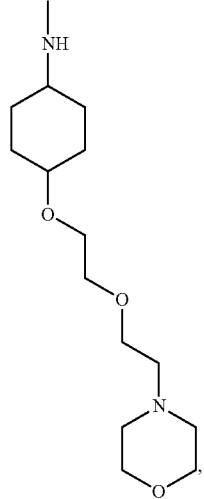

or a combination thereof; and R$^1$, R$^2$, R$^3$, and R$^4$ are independently at each occurrence hydrogen, C$_{1-12}$ alkyl, C$_{3-12}$ cycloalkyl, a C$_{3-12}$ cycloalkyl ether, C$_{5-12}$ bicycloalkyl, a C$_{6-12}$ tricycloalkyl, or a combination thereof, optionally wherein R$^1$ and R$^2$ can join together to form a C$_{3-12}$ azacycloalkyl group or R$^3$ and R$^4$ can join together to form a C$_{3-12}$ azacycloalkyl group, provided that at least one of R$^1$ and R$^2$ and at least one of R$^3$ and R$^4$ are not hydrogen; when any of R$^1$, R$^2$, R$^3$, or R$^4$ are C$_{3-12}$ cycloalkyl, X is not

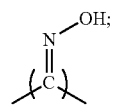

and when at least one of R$^1$ and R$^2$ is a C$_{3-12}$ cycloalkyl ether, R$^3$ and R$^4$ are not a C$_{3-12}$ cycloalkyl ether.

Aspect 2: The compound of aspect 1, wherein each occurrence of R is hydrogen

Aspect 3: The compound of aspect 1 or 2, wherein X is

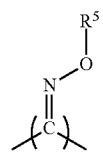

wherein R$^5$ is hydrogen or propargyl.

Aspect 4: The compound of any of aspects 1 to 3, wherein R$^1$ and R$^3$ are hydrogen and R$^2$ and R$^4$ are C$_{1-6}$ alkyl.

Aspect 5: The compound of any of aspects 1 to 3, wherein R$^1$ and R$^3$ are hydrogen and R$^2$ and R$^4$ are C$_{5-8}$ bicycloalkyl.

Aspect 6: The compound of aspect 1, wherein each occurrence of R is hydrogen, X is

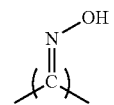

R$^1$ and R$^3$ are hydrogen, and R$^2$ and R$^4$ are bicyclo[3.1.2.]heptane, and the compound is of the formula

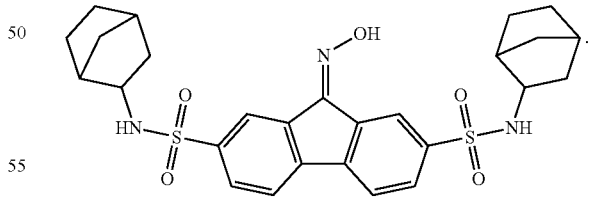

Aspect 7: The compound of aspect 1, wherein R is hydrogen, X is

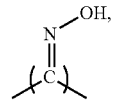

R¹ and R³ are hydrogen, and R² and R⁴ are bicyclo[1.1.1]pentane, and the compound is of the formula

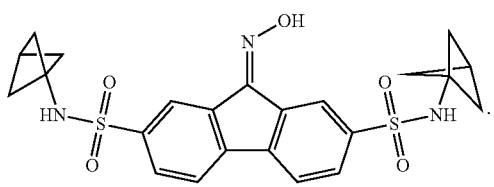 [SMILES: O=S(=O)(NC12CC(C1)C2)c1ccc2c(c1)C(=NO)c1cc(S(=O)(=O)NC34CC(C3)C4)ccc1-2]

Aspect 8: The compound of aspect 1, wherein R is hydrogen, X is

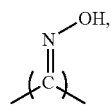

R¹ and R³ are hydrogen, and R² and R⁴ are 3-pentyl, and the compound is of the formula

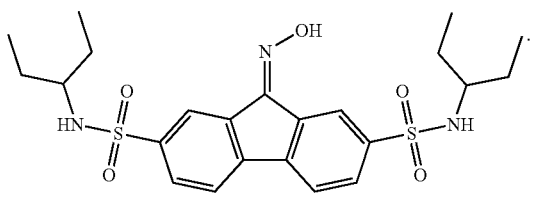 [SMILES: CCC(CC)NS(=O)(=O)c1ccc2c(c1)C(=NO)c1cc(S(=O)(=O)NC(CC)CC)ccc1-2]

Aspect 9: The compound of aspect 1, wherein R is hydrogen, X is

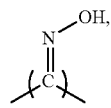

R¹ and R³ are hydrogen, and R² and R⁴ are spiro[3.3]heptane, and the compound is of the formula

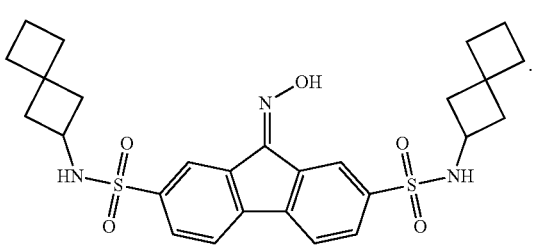 [SMILES: O=S(=O)(NC1CC2(CCC2)C1)c1ccc2c(c1)C(=NO)c1cc(S(=O)(=O)NC3CC4(CCC4)C3)ccc1-2]

Aspect 10: The compound of aspect 1, wherein R is hydrogen, X is

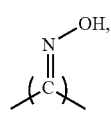

and R¹ and R² and R³ and R⁴ are joined together to form an azaspiro[3.3]heptane group, and the compound is of the formula

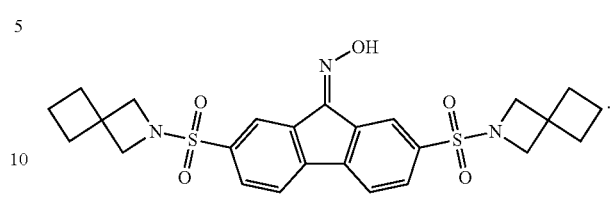

Aspect 11: The compound of any of aspects 1 to 10, wherein the compound has a half maximal effective concentration ($EC_{50}$) of less than 2 μM, preferably 0.01 to 2.0 μM, or 0.05 to 1.9 μM, or 0.05 to 0.25 μM in HT 1080 cells.

Aspect 12: A composition comprising a compound of any of aspects 1 to 11.

Aspect 13: The composition of aspect 12, further comprising a pharmaceutically acceptable carrier, adjuvant, or vehicle.

Aspect 14: A method of inducing ferroptosis in a cell, the method comprising contacting the cell with an effective amount of the compound of any of aspects 1 to 11, or the composition of aspects 12 or 13.

Aspect 15: The method of aspect 14, wherein the compound is selected from

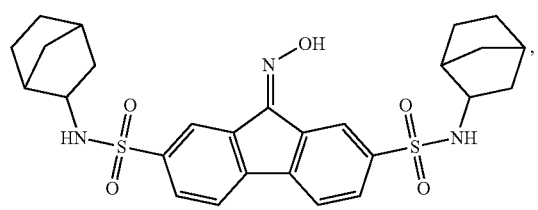

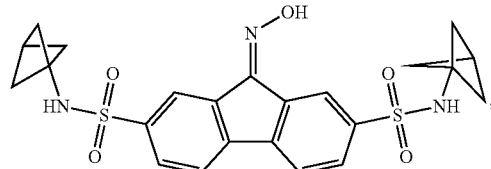

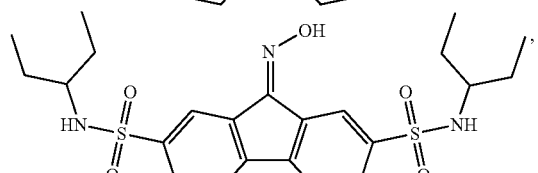

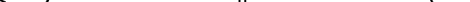

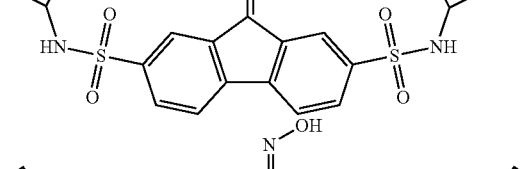

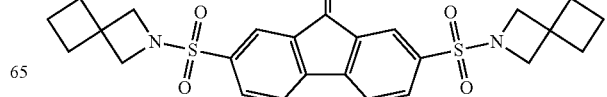

Aspect 16: The method of aspect 14, wherein the compound is of the formula

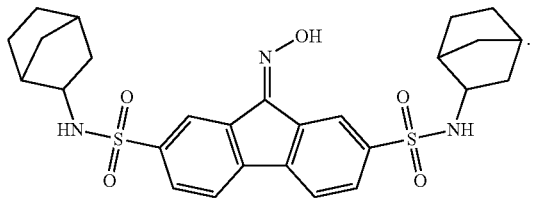 [SMILES: O=S(=O)(NC1CC2CCC1C2)c1ccc2c(c1)C(=NO)c1cc(S(=O)(=O)NC3CC4CCC3C4)ccc1-2]

Aspect 17: The method of any of aspects 14 to 16, wherein the cell is a mammalian cell.

Aspect 18: The method of any of aspects 14 to 17, wherein the method is carried out in vitro, in vivo, or ex vivo.

The compositions and methods can alternatively comprise, consist of, or consist essentially of, any appropriate materials, steps, or components herein disclosed. The compositions and methods can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "an aspect" means that a particular element described in connection with the aspect is included in at least one aspect described herein, and may or may not be present in other aspects. The term "combination thereof" as used herein includes one or more of the listed elements, and is open, allowing the presence of one or more like elements not named. In addition, it is to be understood that the described elements may be combined in any suitable manner in the various aspects.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, saturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo atoms (e.g., bromo and fluoro), or only chloro atoms can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl), a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A compound according to Formula 1

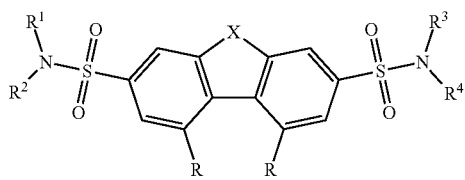

wherein
each occurrence of R is hydrogen, X is

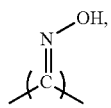

$R^1$ and $R^3$ are hydrogen, and $R^2$ and $R^4$ are bicyclo[3.1.2.] heptane, and the compound is of the formula

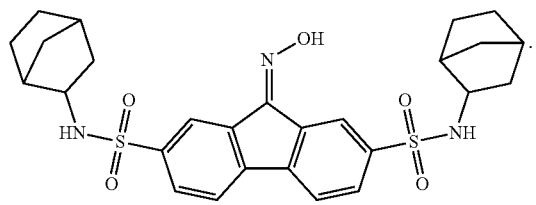 [SMILES: O=S(=O)(NC1CC2CCC1C2)c1ccc2c(c1)C(=NO)c1cc(S(=O)(=O)NC3CC4CCC3C4)ccc1-2]

or
R is hydrogen, X is

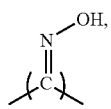

$R^1$ and $R^3$ are hydrogen, and $R^2$ and $R^4$ are bicylo[1.1.1] pentane, and the compound is of the formula

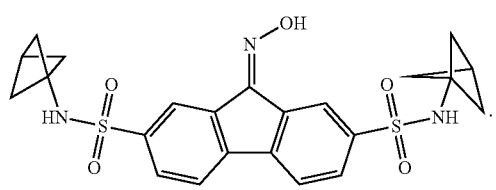 [SMILES: O=S(=O)(NC12CC(C1)C2)c1ccc2c(c1)C(=NO)c1cc(S(=O)(=O)NC34CC(C3)C4)ccc1-2]

or
R is hydrogen, X is

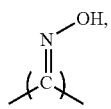

$R^1$ and $R^3$ are hydrogen, and $R^2$ and $R^4$ are 3-pentyl, and the compound is of the formula

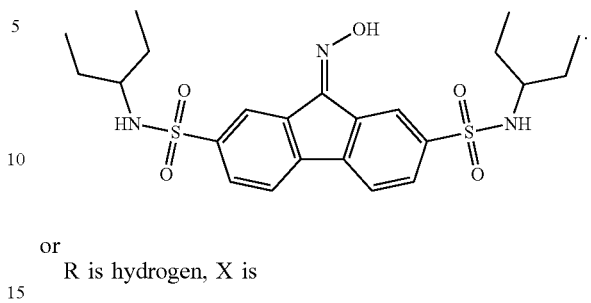

or
R is hydrogen, X is

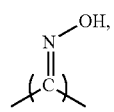

$R^1$ and $R^3$ are hydrogen, and $R^2$ and $R^4$ are spiro[3.3] heptane, and the compound is of the formula

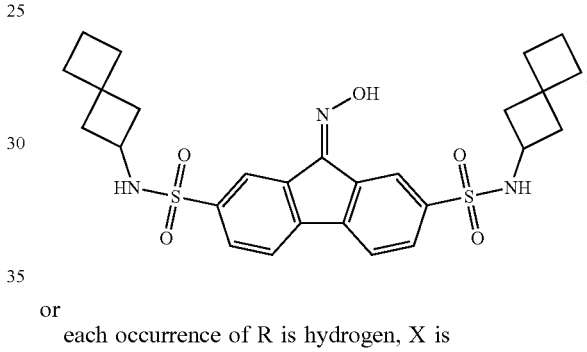

or
each occurrence of R is hydrogen, X is

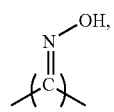

$R^1$ and $R^3$ are each hydrogen, and $R^2$ and $R^4$ are each adamantyl groups, and the compound is of the formula

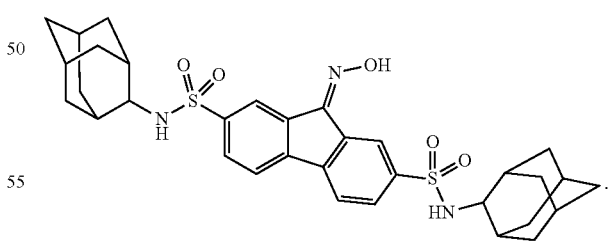

2. The compound of claim 1, wherein the compound has a half maximal effective concentration ($EC_{50}$) of less than 2 μM in HT 1080 cells.

3. A composition comprising a compound of claim 1.

4. The composition of claim 3, further comprising a pharmaceutically acceptable carrier, adjuvant, or vehicle.

5. A method of inducing ferroptosis in a cell, the method comprising contacting the cell with an effective amount of the compound of claim 1.

6. The method of claim 5, wherein the compound is of the formula
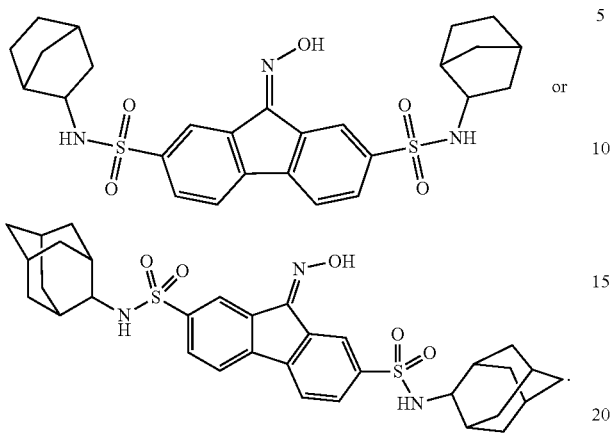 or
7. The method of claim 5, wherein the cell is a mammalian cell.
8. The method of claim 5, wherein the method is carried out in vitro, in vivo, or ex vivo.
* * * * *